US008241861B1

(12) United States Patent
Heinecke et al.

(10) Patent No.: US 8,241,861 B1
(45) Date of Patent: Aug. 14, 2012

(54) METHODS AND COMPOSITIONS FOR DIAGNOSIS OR PROGNOSIS OF CARDIOVASCULAR DISEASE

(75) Inventors: Jay W. Heinecke, Seattle, WA (US);
Tomas Vaisar, Bellevue, WA (US);
Bryan Prazen, Seattle, WA (US); Erik Nilsson, Seattle, WA (US)

(73) Assignees: Insilicos, LLC, Seattle, WA (US);
University of Washington, Seattle, WA (US)

( * ) Notice: Subject to any disclaimer, the term of this patent is extended or adjusted under 35 U.S.C. 154(b) by 497 days.

(21) Appl. No.: 12/499,711

(22) Filed: Jul. 8, 2009

Related U.S. Application Data

(60) Provisional application No. 61/079,088, filed on Jul. 8, 2008.

(51) Int. Cl.
*G01N 31/00* (2006.01)
*G01N 33/53* (2006.01)

(52) U.S. Cl. ........ 435/7.21; 435/7.1; 436/501; 436/518; 424/9.1; 424/520; 422/50; 530/300; 530/350

(58) Field of Classification Search .................. None
See application file for complete search history.

(56) References Cited

U.S. PATENT DOCUMENTS 6,225,047 B1    5/2001    Hutchens

FOREIGN PATENT DOCUMENTS

| WO | 2006/014628 A1 | 2/2006 |
| WO | 2006/083852 A2 | 8/2006 |
| WO | 2006/083853 A2 | 8/2006 |

OTHER PUBLICATIONS

Asztalos, B.F., and E.J. Schaefer, "High-Density Lipoprotein Subpopulations in Pathologic Conditions," American Journal of Cardiology 91(7, Suppl. 1):12E-17E, Apr. 2003.
Barter, P.J., et al., "Antiinflammatory Properties of HDL," Circulation Research 95(8):764-772, Oct. 2004.
Davidson, W.S, and T.B. Thompson, "The Structure of Apolipoprotein A-I in High Density Lipoproteins," Journal of Biological Chemistry. 282(31):22249-22253, Aug. 2007.
De Beer, M.C., et al., "Apolipoprotein A-I Conformation Markedly Influences HDL Interaction With Scavenger Receptor BI," Journal of Lipid Research 42(2):309-313, Feb. 2001.
Di Natale, C., et al., "Lung cancer identification by the analysis of breath by means of an array of non-selective gas sensors," Biosensors and Bioelectronics 18(10):1209-1218, 2003.
Ghazalpour, A., et al., "Thematic review series: The Pathogenesis of Atherosclerosis. Toward a biological network for atherosclerosis," Journal of Lipid Research 45(10):1793-1805, Oct. 2004.
Gygi, S.P., et al., "Quantitative Analysis of Complex Protein Mixtures Using Isotope-Coded Affinity Tags," Nature Biotechnology 17(10):994-999, Oct. 1999.
Hazell, L.J., et al., "Presence of hypochlorite-modified proteins in human atherosclerotic lesions," Journal of Clinical Investigation 97(6):1535-1544, Mar. 1996.
Kersey, P.J., et al., "The International Protein Index: An Integrated Database for Proteomics Experiments," Proteomics 4(7):1985-1988, Jul. 2004.
Marcel, Y.L., et al, "Monoclonal antibodies and the characterization of apolipoprotein structure and function," Progress in Lipid Research 23(4):169-95, 1984.
Marcel, Y.L., et al., "Lipid Peroxidation Changes the Expression of Specific Epitopes of Apolipoprotein A I," Journal of Biological Chemistry 264(33):19942-19950, Nov. 1989.
Marcel, Y.L., et al., "The epitopes of apolipoprotein A-I define distinct structural domains including a mobile middle region," Journal of Biological Chemistry 266(6):3644-53, Feb. 1991.
Mendez, A.J., et al., "Protein Kinase C as a Mediator of High Density Lipoprotein Receptor-Dependent Efflux of Intracellular Cholesterol," Journal of Biological Chemstry 266(16):10104-10111, Jun. 1991.
Milthorp, P., et al., "Immunochemical characterization of apolipoprotein A-I from normal human plasma. In vitro modification of apo A-I antigens," Arteriosclerosis 6(3):285-96, May-Jun. 1986.
Nesvizhskii, A.I., et al., "A Statistical Model for Identifying Proteins by Tandem Mass Spectrometry," Analytical Chemistry 75(17):4646-4658, Sep. 2003.
O'Brien, K.D., et al., "Comparison of Apolipoprotein and Proteoglycan Deposits in Human Coronary Atherosclerotic Plaques: Colocalization of Biglycan With Apolipoproteins," Circulation 98(6):519-527, Aug. 1998.
Ooi, E.M.M., et al., "Apolipoprotein C-III: Understanding an Emerging Cardiovascular Risk Factor," Clinical Science (London) 114(10):611-624, May 2008.
Oram, J.F., "HDL Apolipoproteins and ABCA1: Partners in the Removal of Excess Cellular Cholesterol," Arteriosclerosis, Thrombosis, and Vascular Biology 23(5):720-727, May 2003.
Parthasarathy, S., et al., "High-Density Lipoprotein Inhibits the Oxidative Modification of Low-Density Lipoprotein," Biochimica et Biophysica Acta 1044(2):275-283, May 1990.
Qian, W.-J., et al., "Comparative proteome analyses of human plasma following in vivo lipopolysaccharide administration using multidimensional separations coupled with tandem mass spectrometry," Proteomics 5(2):572-584, Feb. 2005.
Rocke, D.M, "Design and analysis of experiments with high throughput biological assay data," Seminars in Cell and Developmental Biology 15(6):703-13, Dec. 2004.

(Continued)

*Primary Examiner* — Lisa Cook
(74) *Attorney, Agent, or Firm* — Christensen O'Connor Johnson Kindness PLLC

(57) ABSTRACT

The invention provides methods of screening a mammalian subject to determine if the subject is at risk to develop or is suffering from, cardiovascular disease. In one embodiment, the method comprises detecting a measurable feature of at least two biomarkers in an HDL subfraction, or in a complex containing apoA-I or apoA-II isolated from a biological sample obtained from the subject, wherein the at least two biomarkers are selected from the group consisting of apoA-I, apoA-II, apoB-100, Lp(a), apoC-I, and apoC-III, combinations or portions and/or derivatives thereof, and comparing the measurable features of the at least two biomarkers from the biological sample to a reference standard, wherein a difference in the measurable features of the at least two biomarkers from the biological sample and the reference standard is indicative of the presence or risk of cardiovascular disease in the subject.

18 Claims, 13 Drawing Sheets

OTHER PUBLICATIONS

Shachter, N.S., "Apolipoproteins C-I and C-III as Important Modulators of Lipoprotein Metabolism," Current Opinion in Lipidology 12(3):297-304, Jun. 2001.

Shao, B., et al., "Myeloperoxidase impairs ABCA1-dependent cholesterol efflux through methionine oxidation and site-specific tyrosine chlorination of apolipoprotein A-I," Journal of Biological Chemistry 281(14):9001-9004, Apr. 2006.

Sparks, D.L., and P.H. Pritchard, "Transfer of Cholesteryl Ester Into High Density Lipoprotein by Cholesteryl Ester Transfer Protein: Effect of HDL Lipid and Apoprotein Content," Journal of Lipid Research 30(10):1491-1498, Oct. 1989.

Stanley, B.A., et al., "Heart Disease, Clinical Proteomics and Mass Spectrometry," Disease Markers 20(3):167-178, 2004.

Stemmann, O., et al., "Dual Inhibition of Sister Chromatid Separation at Metaphase," Cell 107(6):715-726, Dec. 2001.

Strader, M.B., et al., "Efficient and Specific Trypsin Digestion of Microgram to Nanogram Quantities of Proteins in Organic-Aqueous Solvent Systems," Analytical Chemistry 78(1):125-134, Jan. 2006.

Tall, A.R., et al., "Regulation and Mechanisms of Macrophage Cholesterol Efflux," Journal of Clinical Investigation 110(7):899-904, Oct. 2002.

Vaisar, T., et al., "Shotgun Proteomics Implicates Protease Inhibition and Complement Activation in the Antiinflammatory Properties of HDL," Journal of Clinical Investigation 117(3):746-756, Mar. 2007.

Walldius, G., and I. Jungner, "Apolipoprotein A-I Versus HDL Cholesterol in the Prediction of Risk for Myocardial Infarction and Stroke," Current Opinion in Cardiology 22(4):359-367, Jul. 2007.

Walldius, G., and I. Jungner, "The apoB/apoA-I Ratio: A Strong, New Risk Factor for Cardiovascular Disease and a Target for Lipid-Lowering Therapy—A Review of the Evidence," Journal of Internal Medicine 259(5):493-519, May 2006.

Weech, P.K., et al., "Apolipoprotein A-I From Normal Human Plasma: Definition of Three Distinct Antigenic Determinants," Biochimica et Biophysica Acta 835(2):390-401, Jul. 1985.

Wilson, P.W.F., et al., "High Density Lipoprotein Cholesterol and Mortality. The Framingham Heart Study," Arteriosclerosis, Thrombosis and Vascular Biology 8(6):737-741, Nov. 1988.

Wilson, P.W.F., et al., "Prediction of Coronary Heart Disease Using Risk Factor Categories," Circulation 97 (18):1837-1847, May 1998.

Yan, W., et al., "A Dataset of Human Liver Proteins Identified by Protein Profiling Via Isotope-coded Affinity Tag (ICAT) and Tandem Mass Spectrometry," Molecular and Cellular Proteomics 3(10):1039-1041, Oct. 2004.

Yusuf, S., et al., "Effect of Potentially Modifiable Risk Factors Associated With Myocardial Infarction in 52 Countries (the Interheart Study): Case-Control Study," Lancet 364(9438):937-952, Sep. 2004.

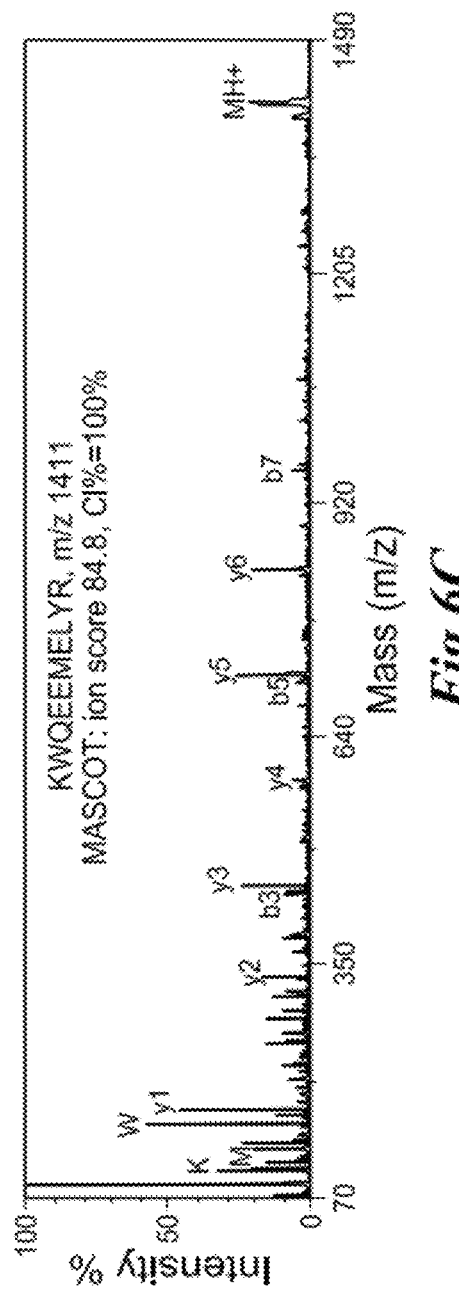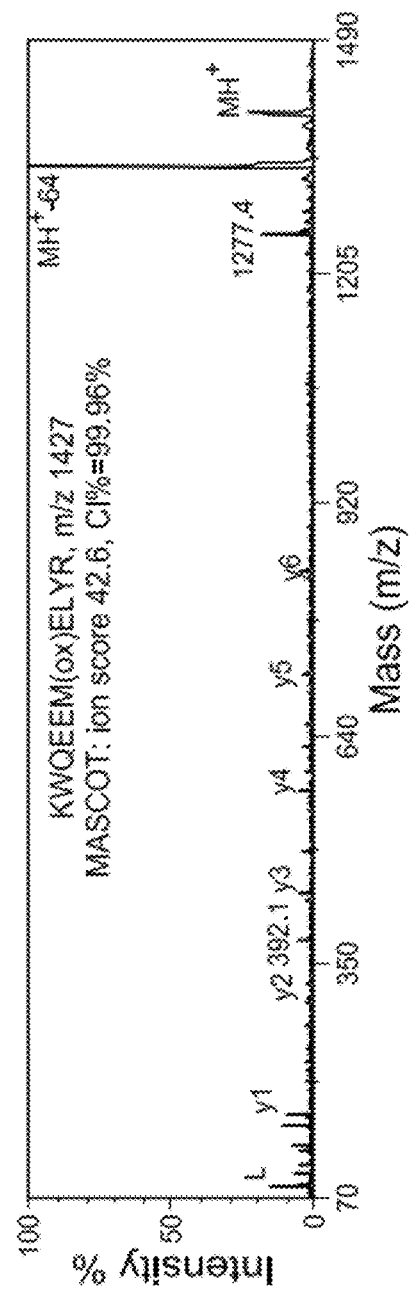

METHODS AND COMPOSITIONS FOR DIAGNOSIS OR PROGNOSIS OF CARDIOVASCULAR DISEASE

CROSS-REFERENCE TO RELATED APPLICATION

This application claims the benefit of Application No. 61/079,088, filed Jul. 8, 2008,

STATEMENT OF GOVERNMENT LICENSE RIGHTS

This invention was made with U.S. Government support under NIH grant number HL086798, awarded by the National Institutes of Health. The U.S. Government has certain rights in this invention.

FIELD OF THE INVENTION

The present invention generally relates to methods, reagents, and kits for diagnosing cardiovascular disease in a subject, and particularly relates to the use of lipoprotein-associated markers to diagnose cardiovascular disease in a subject.

BACKGROUND

Cardiovascular disease is a leading cause of morbidity and mortality, particularly in developed areas such as the United States and Western European countries. The incidence of mortality from cardiovascular disease has significantly decreased in the United States over the past 30 years (see Braunwald, E., N. *Engl. J. Med.* 337:1360-1369, 1997; Hoyert, D. L., et al., "Deaths: Preliminary Data for 2003" in *National Vital Statistics Reports*. Hyattsville: National Center for Health Statistics, 2005). Many factors have contributed to this improvement in patient outcome, including the identification of cardiovascular risk factors, the application of medical technologies to treat acute coronary syndrome, and the development of interventions that reduce cardiovascular risk factors. Despite these advances, however, cardiovascular disease remains a leading cause of morbidity and mortality in developed countries (see Hoyert D. L., et al., *National Vital Statistics Reports*, 2005).

Thus, there is a pressing need to identify markers that may be used for the rapid, accurate and non-invasive diagnosis and/or assessment of the risk of cardiovascular disease, and also to assess the efficacy of interventions designed to slow the initiation and progress of this disorder.

SUMMARY

In accordance with the foregoing, in one aspect, the present invention provides a method of screening a mammalian subject to determine if the subject is at risk to develop, or is suffering from, cardiovascular disease, the method comprising detecting a measurable feature of at least two biomarkers in an HDL subfraction, or in a complex containing apoA-I or apoA-II isolated from a biological sample obtained from the subject, wherein the at least two biomarkers are selected from the group consisting of apoA-I, apoA-II, apoB-100, Lp(a), apoC-I, and apoC-III, combinations or portions and/or derivatives thereof, and comparing the measurable features of the at least two biomarkers from the biological sample to a reference standard, wherein a difference in the measurable features of the at least two biomarkers from the biological sample and the reference standard is indicative of the presence or risk of cardiovascular disease in the subject.

In another aspect, the present invention provides a method for diagnosing and/or assessing the risk of CAD in a subject, comprising determining changes in a biomarker profile comprising the relative abundance of at least one, two, three, four, five, ten or more biomarkers in an HDL subfraction or in a complex containing apoA-I or apoA-II isolated from a biological sample obtained from a test subject as compared to the predetermined abundance of the at least one, two, three, four, five, ten or more biomarkers from a reference population of apparently healthy subjects, wherein the biomarkers are selected from the biomarkers set forth in TABLE 3, TABLE 4, and TABLE 5.

In another aspect, the present invention provides a method of screening a mammalian subject to determine if a test subject is at risk to develop, is suffering from, or recovering from, cardiovascular disease, the method comprising detecting an alteration in the conformational structure of apoA-I present in the HDL subfraction or in a complex containing apoA-I or apoA-II isolated from a biological sample obtained from the test subject in comparison to a reference standard, wherein a difference in the conformation of the apoA-I between the biological sample from the test subject and the reference standard is indicative of the presence or risk of cardiovascular disease in the subject.

In another aspect, the present invention provides a method for determining the efficacy of a treatment regimen for treating and/or preventing cardiovascular disease in a subject by monitoring a measurable feature of at least two biomarkers selected from the group consisting of apoA-I, apoA-II, apoB-100, Lp(a), apoC-I, and apoC-III, combinations or portions and/or derivatives thereof in an HDL subfraction or in a complex containing apoA-I or apoA-II isolated from a biological sample obtained from the subject during treatment for cardiovascular disease.

In yet another aspect, the present invention provides a kit for determining susceptibility or presence of cardiovascular disease in a mammalian subject based on the detection of at least one measurable feature of at least one biomarker in a biological sample, an HDL subfraction thereof, or a complex containing apoA-I or apoA-II isolated from the biological sample, the kit comprising (i) one or more detection reagents for detecting the at least one measurable feature of the at least one biomarker selected from the group consisting of apoA-I, apoA-II, apoB-100, Lp(a), apoC-I, and apoC-III, and (ii) written indicia indicating a positive correlation between the presence of the detected feature of the biomarker and the diagnosis or risk of developing cardiovascular disease.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 6A to FIG. 6D graphically illustrate the PLS-DA regression vector features corresponding to apoA-I peptides containing Met112, with pairs of specific informative features at m/z 1411 and 1427 and m/z 2645 and 2661 corresponding to signals detected for M and M+16 respectively, wherein the positive features signify an increase of oxidized form of Met112 peptide, and negative features at m/z 1411 and m/z 2645 indicate a decreased level of the peptide containing unoxidized Met112 in the CAD samples, as described in Example 4;

DETAILED DESCRIPTION

Figure 1:
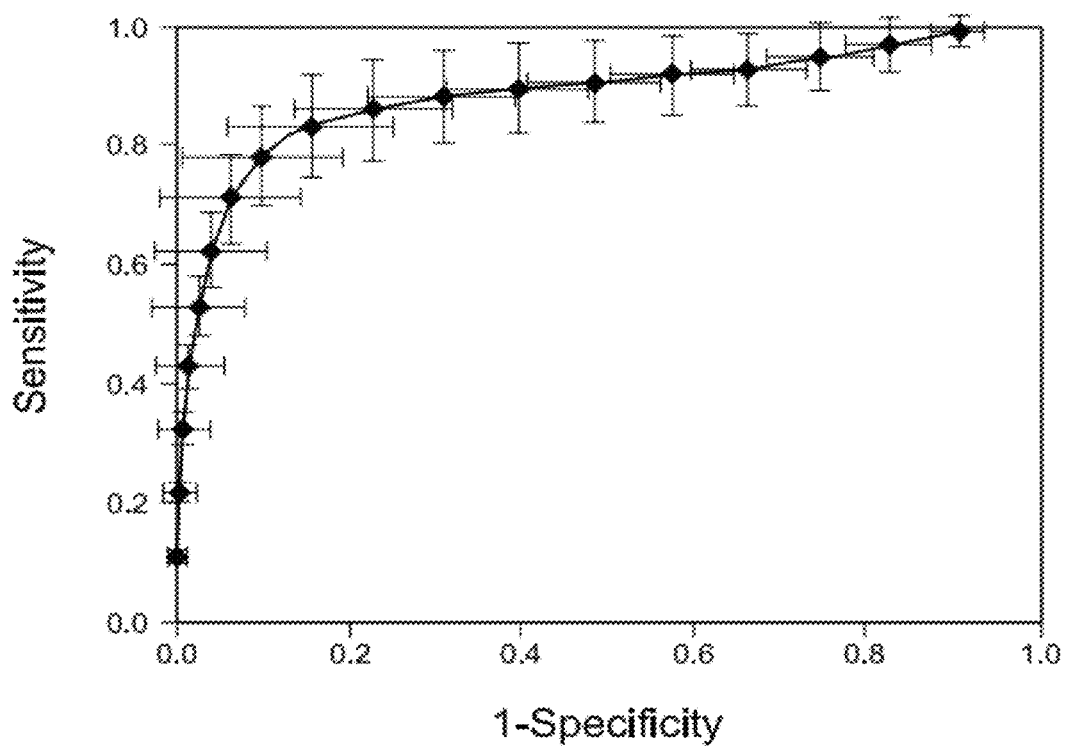
FIG. 1 presents graphical results demonstrating the receiver operating characteristic (ROC) curve of the prediction of cardiovascular disease (CAD) status based on random permutation analysis, as described in Example 2.

As used herein, the term "cardiovascular disease" or "CAD," generally refers to heart and blood vessel diseases, including atherosclerosis, coronary heart disease, cerebrovascular disease, and peripheral vascular disease. Cardiovascular disorders are acute manifestations of CAD and include myocardial infarction, stroke, angina pectoris, transient ischemic attacks, and congestive heart failure. Cardiovascular disease, including atherosclerosis, usually results from the build up of fatty material, inflammatory cells, extracellular matrix, and plaque. Clinical symptoms and signs indicating the presence of CAD include one or more of the following: chest pain and other forms of angina, shortness of breath, sweatiness, Q waves or inverted T waves on an EKG, a high calcium score by CT scan, at least one stenotic lesion on coronary angiography, or heart attack documented by changes in myocardial enzyme levels (e.g., troponin, CK levels).

As used herein, the term "biomarker" is a biological compound, such as a protein or a peptide fragment thereof, including a polypeptide or peptide that may be isolated from or measured in the biological sample, wherein the biomarker is differentially present or absent, or present in a different structure (i.e., post-translationally modified, or in an altered structural conformation) in a sample taken from a subject having established or potentially clinically significant CAD as compared to a comparable sample taken from an apparently normal subject that does not have CAD. A biomarker can be an intact molecule, or it can be a portion thereof or an altered structure thereof, that may be partially functional and recognized, for example, by a specific binding protein or other detection method. A biomarker is considered to be informative for CAD if a measurable feature of the biomarker is associated with the presence of CAD in a subject in comparison to a predetermined value or a reference profile from a control population. Such a measurable feature may include, for example, the presence, absence, or concentration of the biomarker, or a portion thereof, in the biological sample, an altered structure, such as, for example, the presence or amount of a post-translational modification, such as oxidation at one or more positions on the amino acid sequence of the biomarker or, for example, the presence of an altered conformation in comparison to the conformation of the biomarker in normal control subjects, and/or the presence, amount, or altered structure of the biomarker as a part of a profile of more than one biomarker. A measurable aspect of a biomarker is also referred to as a feature. A feature may be a ratio of two or more measurable aspects of biomarkers. A biomarker profile comprises at least two measurable informative features, and may comprise at least three, four, five, 10, 20, 30 or more informative features. The biomarker profile may also comprise at least one measurable aspect of at least one feature relative to at least one internal standard.

As used herein, the term "predetermined value" refers to the amount and/or structure of one or more biomarkers in biological samples obtained from the general population or from a select population of subjects. For example, the select population may be comprised of apparently healthy subjects, such as individuals who have not previously had any sign or symptoms indicating the presence of CAD. In another example, the predetermined value may be comprised of subjects having established CAD. The predetermined value can be a cut-off value or a range. The predetermined value can be established based upon comparative measurements between apparently healthy subjects and subjects with established CAD, as described herein.

As used herein, the term "high density lipoprotein" or "HDL, or a subfraction thereof" includes protein or lipoprotein complexes with a density from about 1.06 to about 1.21 g/mL, or from about 1.06 to 1.10 g/mL, or from about 1.10 to about 1.21 g/mL, or a complex containing apoA-I or apoA-II. HDL may be prepared by density ultracentrifugation, as described in Mendez, A. J., et al., *J. Biol. Chem.* 266:10104-10111, 1991, from plasma, serum, bodily fluids, or tissue. The $HDL_3$ subfraction in the density range of about 1.110 to about 1.210 g/mL, and the $HDL_2$ subfraction in the density range of about 1.06 to about 1.125 g/mL may be isolated from plasma, serum, bodily fluids, tissue or total HDL by sequential density ultracentrifugation, as described in Mendez, supra. HDL is known to contain two major proteins, apolipoprotein A-I (apoA-I) and apolipoprotein A-II (apoA-II); therefore, in some embodiments, the term "HDL, or a subfraction thereof" also includes an apoA-I and/or an apoA-II containing protein or lipoprotein complex which may be isolated, for example, by immunoaffinity with anti-apoA-I or anti-apoA-II antibodies.

As used herein, the term "HDL-associated" refers to any biological compounds that float in the density range of HDL (d=about 1.06 to about 1.21 g/mL) and/or molecules present in a complex containing apoA-I and/or apoA-II, including full-length proteins and fragments thereof, including peptides or lipid-protein complexes, such as microparticles, in HDL isolated from any sample, including lesions, blood, urine, cerebral spinal fluid, bronchoalveolar fluid, joint fluid, or tissue or fluid samples.

As used herein, the term "$HDL_2$-associated" refers to any biological compounds that float in the density range of $HDL_2$ (d=about 1.06 to about 1.125 g/mL) and/or molecules present in a complex containing apoA-I and/or apoA-II, including full-length proteins, and fragments thereof, including peptides, or lipid-protein complexes such as microparticles, in HDL isolated from any sample, including lesions, blood, urine, cerebral spinal fluid, bronchoalveolar fluid, joint fluid, or tissue or fluid samples.

As used herein, the term "mass spectrometer" refers to a device able to volatilize/ionize analytes to form gas-phase ions and determine their absolute or relative molecular masses. Suitable forms of volatilization/ionization are matrix-assisted laser desorption ionization (MALDI), electrospray, laser/light, thermal, electrical, atomized/sprayed and the like, or combinations thereof. Suitable forms of mass spectrometry include, but are not limited to, ion trap instruments, quadrupole instruments, electrostatic and magnetic sector instruments, time of flight instruments, time of flight tandem mass spectrometer (TOF MS/MS), Fourier-transform mass spectrometers, and hybrid instruments composed of various combinations of these types of mass analyzers. These instruments may, in turn, be interfaced with a variety of sources that fractionate the samples (for example, liquid chromatography or solid-phase adsorption techniques based on chemical, or biological properties) and that ionize the samples for introduction into the mass spectrometer, including matrix-assisted laser desorption (MALDI), electrospray, or nanospray ionization (ESI) or combinations thereof.

As used herein, the term "affinity detection" or "affinity purified" refers to any method that selectively detects and/or enriches the protein or analyte of interest. This includes methods based on physical properties like charge, amino acid sequence, and hydrophobicity, and can involve many different compounds that have an affinity for the analyte of interest, including, but not limited to, antibodies, resins, RNA, DNA, proteins, hydrophobic materials, charged materials, and dyes.

As used herein, the term "antibody" encompasses antibodies and antibody fragments thereof derived from any antibody-producing mammal (e.g., mouse, rat, rabbit, and primate including human) that specifically bind to the biomarkers or portions thereof. Exemplary antibodies include polyclonal, monoclonal, and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

As used herein, the term "antibody fragment" refers to a portion derived from or related to a full length anti-biomarker antibody, generally including the antigen binding or variable region thereof. Illustrative examples of antibody fragments include Fab, Fab', $F(ab)_2$, $F(ab')_2$ and Fv fragments, scFv fragments, diabodies, linear antibodies, single-chain antibody molecules and multispecific antibodies formed from antibody fragments. Antibody and antibody fragments as used here may be incorporated into other proteins that can be produced by a variety of systems, including, but not limited to, bacteria, viruses, yeast, and mammalian cells.

As used herein, "a subject" includes all mammals, including without limitation humans, non-human primates, dogs, cats, horses, sheep, goats, cows, rabbits, pigs and rodents.

As used herein, the term "percent identity" or "percent identical," when used in connection with a biomarker used in the practice of the present invention, is defined as the percentage of amino acid residues in a biomarker sequence that are identical with the amino acid sequence of a specified biomarker after aligning the sequences to achieve the maximum percent identity. When making the comparison, no gaps are introduced into the biomarker sequences in order to achieve the best alignment.

Amino acid sequence identity can be determined, for example, in the following manner. The amino acid sequence of a biomarker is used to search a protein sequence database, such as the GenBank database, using the BLASTP program. The program is used in the ungapped mode. Default filtering is used to remove sequence homologies due to regions of low complexity. The default parameters of BLASTP are utilized.

As used herein, the term "derivatives" of a biomarker, including proteins and peptide fragments thereof, include an insertion, deletion, or substitution mutant. Preferably, any substitution mutation is conservative in that it minimally disrupts the biochemical properties of the biomarker. Thus, where mutations are introduced to substitute amino acid residues, positively-charged residues (H, K, and R) preferably are substituted with positively-charged residues; negatively-charged residues (D and E) are preferably substituted with negatively-charged residues; neutral polar residues (C, G, N, Q, S, T, and Y) are preferably substituted with neutral polar residues; and neutral non-polar residues (A, F, I, L, M, P, V, and W) are preferably substituted with neutral non-polar residues.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His; H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys, or Pro. By "hydrophilic" amino acid is meant either Gly, Asn, Gln, Ser, Thr, Asp, Glu, Lys, Arg, or His. This grouping of amino acids can be further subclassed as follows. By "uncharged hydrophilic" amino acid is meant either Ser, Thr, Asn, or Gln. By "acidic" amino acid is meant either Glu or Asp. By "basic" amino acid is meant either Lys, Arg, or His.

In the past, studies have been done to identify proteins in the blood of a subject that could be used as markers for cardiovascular disease (see, e.g., Stanley et al., *Dis. Markers* 20:167-178, 2004). However, this approach has been hampered by the vast number of candidate proteins in blood plasma in concentrations that vary over six orders of magnitude, which complicate the discovery and validation processes (Qian, W. J., et al., *Proteomics* 5:572-584, 2005). Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). HDL particles vary in size and density due to the differences in the number of apolipoproteins on the surface of the particles and the amount of cholesterol esters in the core of HDL (see Asztaloe et al., *Am. J. Cardiol.* 91:12 E-17E, 2003). HDL is composed of two principal subfractions based on density: $HDL_2$ and the denser $HDL_3$.

Elevated LDL cholesterol and total cholesterol are directly related to an increased risk of cardiovascular disease. See Anderson et al., "Cholesterol and Mortality: 30 years of Follow Up from the Framingham Study," *JAMA* 257:2176-90, 1987. In contrast, it has been established that the risk of cardiovascular disease is inversely proportional to plasma levels of HDL and the major HDL apolipoprotein, apoA-I (Gordon, D. J., et al., *N. Engl. J. Med.* 321:1311-1316, 1989). Studies have shown that high HDL levels are associated with longevity (Barzilai, N., et al., *JAMA* 290:2030-2040, 2003). Consistent with these findings, an abnormally low HDL level is a well-accepted risk factor for the development of clinically significant atherosclerosis (particularly common in men with premature atherosclerosis (Gordon, D. J., et al., *N. Engl. J. Med.* 321:1311-1316, 1989; Wilson, P. W., et al., *Arteriosclerosis* 8:737-741, 1988)). The mechanism by which HDL renders its protective effect against atherosclerosis is the subject of continued debate. Some studies have implicated that HDL may directly protect against atherosclerosis by removing cholesterol from artery wall macrophages (see Tall, A. R., et al., *J. Clin. Invest.* 110:899-904, 2002; Oram, J. F., et al., *Arterioscler. Thromb. Vasc. Biol.* 23:720-727, 2003). Other studies have reported that HDL protects against LDL oxidative modification, which is believed to be central to the initiation and progression of atherosclerosis (see, e.g., Parthasarathy, S., et al., *Biochim. Biophys. Acta* 1044:275-283, 1990; Barter, P. J., et al., *Circ Res* 95:764-772, 2004). However, while HDL/LDL ratios have been correlated with risk for cardiovascular disease on an overall population, HDL and/or LDL measurements have not been reliable indicators of risk at an individual level.

Animal studies indicate that one important mechanism by which HDL protects against development of atherosclerosis involves reverse cholesterol transport in which HDL accepts cholesterol from macrophage foam cells in the artery wall and transports it back to the liver for excretion. HDL's cardioprotective effects may also depend on its anti-inflammatory properties. Indeed, HDL contains multiple acute phase response proteins, protease inhibitors and complement regulatory proteins (Vaisar, T., et al., *J Clin Invest* 117(3):746-756 (2007). Although HDL-cholesterol (HDL-C) levels are widely used to assess the risk for CAD, studies with genetically engineered animals convincingly demonstrate that changes in HDL metabolism can promote atherosclerosis by pathways that are independent of plasma levels of HDL-C. Also, the failure of recent clinical trials of a therapy that elevates HDL-C levels suggests that HDL can become dysfunctional in humans.

In accordance with the foregoing, in one aspect, a method of screening a mammalian test subject to determine if the subject is at risk to develop, or is suffering from, cardiovascular disease. The method comprises detecting a measurable feature of at least two biomarkers present in an HDL subfraction, or in a complex containing apoA-I or apoA-II isolated from a biological sample obtained from the subject. The measurable features of the at least two biomarkers selected from the group consisting of apoA-I, apoA-II, apoB-100, Lp(a), apoC-I, and apoC-III, combinations or portions and/or derivatives thereof, are then compared to a reference standard that is derived from measurements of the corresponding biomarkers present in comparable HDL subfractions or complexes isolated from biological samples obtained from a control population, such as a population of apparently healthy subjects. A difference in the measurable features of the at least two biomarkers between the test subject's sample and the reference standard, such as an average value from the control population, is indicative of the presence or risk of developing CAD in the subject. In some embodiments, the method further comprises determining whether the subject is exhibiting symptoms related to CAD.

The methods of this aspect of the invention are useful to screen any mammalian subject, including humans, non-human primates, canines, felines, murines, bovines, equines, and porcines. A human subject may be apparently healthy or may be diagnosed as having a low HDL:LDL ratio and/or as being at risk for CAD based on certain known risk factors such as high blood pressure, high cholesterol, obesity, or genetic predisposition for CAD. The methods described herein are especially useful to identify subjects that are at high risk of developing CAD in order to determine what type of therapy is most suitable and to avoid potential side effects due to the use of medications in low risk subjects. For example, prophylactic therapy is useful for subjects at some risk for CAD, including a low fat diet and exercise. For those at higher risk, a number of drugs may be prescribed by physicians, such as lipid-lowering medications as well as medications to lower blood pressure in hypertensive patients. For subjects at high risk, more aggressive therapy may be indicated, such as administration of multiple medications.

In order to conduct sample analysis, a biological sample containing HDL is provided to be screened, including, but not limited to, whole blood or blood fractions (e.g., serum), bodily fluid, urine, cultured cells, tissue biopsies, or other tissue preparations. In some embodiments of the method of the invention, the biological samples include total HDL (density=about 1.06 to about 1.21 g/mL) or protein complexes that are isolated in this density range. In some embodiments of the method, a complex containing apoA-I and/or apoA-II is isolated from the biological sample. In other embodiments of the method of the invention, an $HDL_2$ subfraction (density=about 1.06 to about 1.125 g/mL) is isolated from the biological sample prior to analysis. The $HDL_2$ fraction may be isolated using any suitable method, such as, for example, through the use of ultracentrifugation, as described in Example 1.

In some embodiments, one or more of the biomarkers apoA-I, apoA-II, apoB-100, Lp(a), apoC-I, and apoC-III, including apoA-I oxidized at methionine residues and/or other HDL-associated peptides and/or proteins are isolated by liquid chromatography, affinity chromatography, or antibody-based methods from biological samples such as, but not limited to, blood, plasma, serum, urine, tissue, or atherosclerotic lesions.

As described in Examples 1-5, the present inventors have used matrix-assisted laser desorption mass spectrometry (MALDI-MS) to investigate the HDL proteome through the use of tryptic digestion. It was determined that the use of pattern recognition with two powerful linear algebraic techniques principal component analysis (PCA) and partial least squares discriminate analysis (PLS-DA) could distinguish between tryptic digested $HDL_2$ subfractions generated from control and CAD subjects at a high level of specificity and selectivity, as described in Example 2. Tandem mass spectrometry of informative mass features used to distinguish between normal and CAD subjects revealed a set of biomarkers for CAD as shown in TABLE 2 which include apoA-I (SEQ ID NO:1), apoA-II (SEQ ID NO:2), apoB-100 (SEQ ID NO:3), Lp(a) (SEQ ID NO:4), apoC-I (SEQ ID NO:5), apoC-III (SEQ ID NO:6), SAA4 (SEQ ID NO:7) and ApoE (SEQ ID NO:8), and peptide fragments and measurable features thereof.

Figure 7:
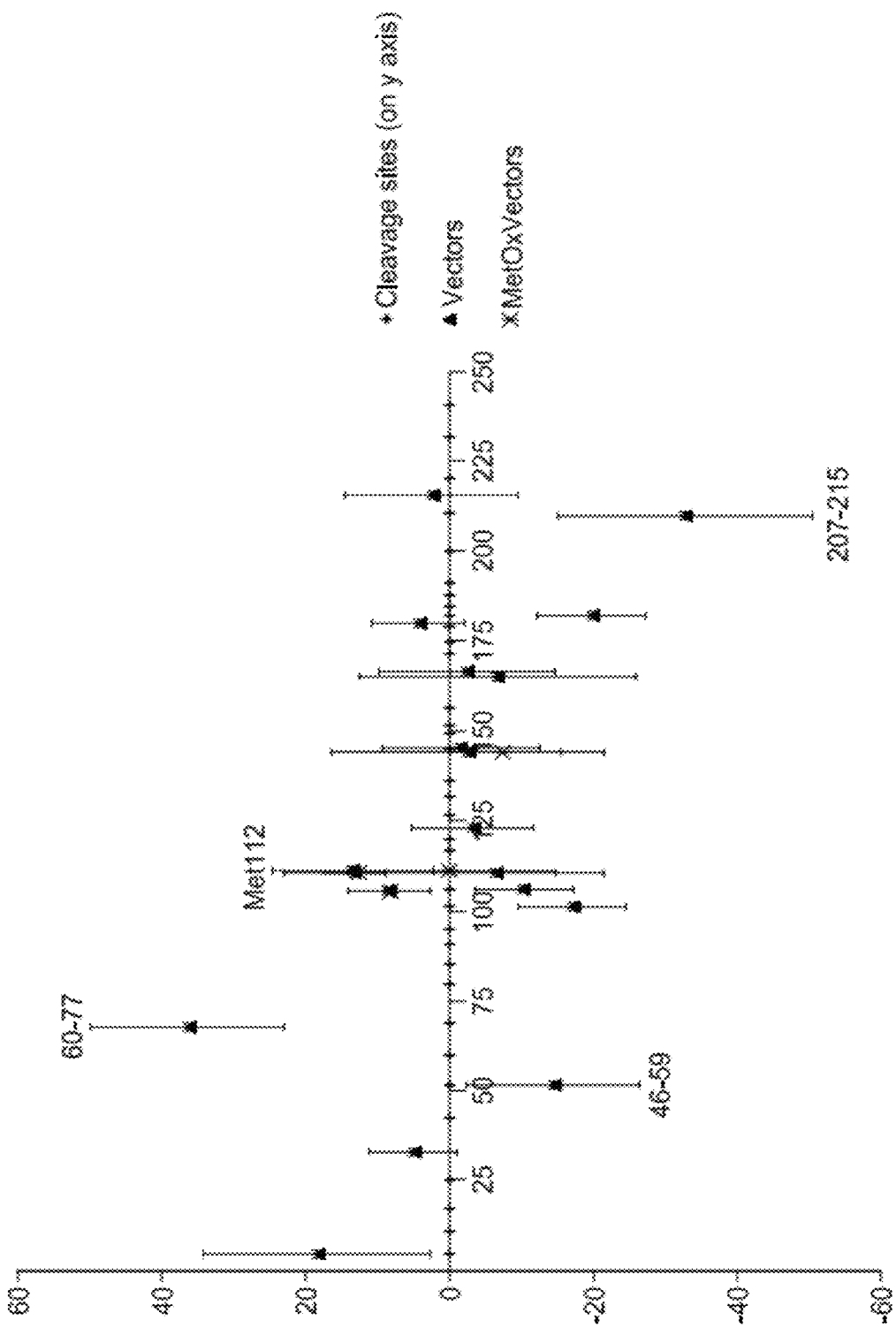
FIG. 7 graphically illustrates the differential digestion efficiency in CAD HDL as compared to normal HDL, in which multiple features in the regression vector (y-axis) correspond to peptides derived from apoA-I (x-axis) with differential features at the N-terminal (residues 46-59, 60-77) and the C-terminal (residues 207-215) domains, indicating a conformational change in apoA-I in the HDL of CAD subjects, as described in Example 5.

The informative features that were identified that are useful to distinguish between normal and CAD subjects fall into the following classes: (1) increased levels of particular peptides/proteins in CAD subjects as compared to normal controls, for example, peptides derived from Lp(a) and/or apoC-III as shown in TABLE 3 and TABLE 4; (2) decreased levels of particular peptides/proteins in CAD subjects as compared to normal controls, for example, peptides derived from apoC-I as shown in TABLE 3 and TABLE 5; (3) post-translational modifications of particular peptides/proteins in CAD subjects as compared to normal controls, for example oxidation of M112 in apoA-I as shown in TABLE 3 and TABLE 6; and (4) altered conformational structure of particular peptides/proteins in CAD subjects as compared to normal controls, for example, apoA-I as shown in FIG. 7 and described in Example 5.

These results demonstrate that HDL isolated from subjects with CAD is selectively enriched in oxidized amino acids and certain proteins, and that the distinct cargo carried by the lipoprotein in subjects with clinically significant CAD may be assessed in a mammalian subject to determine his or her risk for developing CAD, the presence of CAD, and/or the efficacy of treatment of the subject for CAD. Therefore, the identification of peptides/proteins that are present in HDL of subjects suffering from CAD in amounts or structures that differ from normal subjects provide new biomarkers which are useful in assays that are prognostic and/or diagnostic for the presence of CAD and related disorders. The biomarkers may also be used in various assays to assess the effects of exogenous compounds for the treatment of CAD.

In one embodiment of this aspect of the invention, at least one of the measurable features indicative of the presence or risk of cardiovascular disease comprises an increased amount of at least one of the biomarkers in the HDL subfraction of the biological sample selected from the group consisting of apoA-I, apoB-100, apoC-III, and Lp(a), or portions and/or derivatives thereof, in comparison to the reference standard. For example, as demonstrated in Example 3, TABLE 3, and TABLE 4, tryptic peptides have been identified from apoA-I, apoB-100, apoC-III, and Lp(a) that were increased in $HDL_2$ of CAD subjects as compared to normal control subjects. As shown in Examples 1 and 2, these peptides with increased frequency in CAD subjects are informative features for the prognosis and/or diagnosis of CAD.

In another embodiment of this aspect of the invention, at least one of the measurable features indicative of the presence or risk of cardiovascular disease comprises a decreased amount of at least one of the biomarkers in the HDL subfraction of the biological sample selected from the group consisting of apoA-I and apoC-I, or portions and/or derivatives thereof, in comparison to the reference standard. For example, as demonstrated in Example 3, TABLE 3, and TABLE 5, tryptic peptides have been identified from apoA-I and apoC-I that were decreased in $HDL_2$ of CAD subjects as compared to normal control subjects. As shown in Examples 1 and 2, these peptides with decreased frequency in CAD subjects are informative features for the prognosis and/or diagnosis of CAD.

In another embodiment of the invention, at least one of the measurable features indicative of the presence or risk of cardiovascular disease comprises a post-translational modification of a peptide derived from apoA-I in the HDL subfraction of the biological sample, in comparison to the reference standard. For example, as demonstrated in Example 4 and TABLE 6, it has been determined that the oxidation state of apoA-I at M112 is indicative of the presence of CAD.

In the practice of the methods of the methods of this aspect of the invention, a measurable feature of at least two biomarkers (such as at least 3, at least 4, at least 5, or at least 6) selected from the group consisting of apoA-I, apoA-II, apoB-100, Lp(a), apoC-I, and apoC-III is detected. In accordance with this aspect of the invention, proteins having at least 90% identity (such as at least 95% identical, or at least 98% identical) with apoA-I (SEQ ID NO:1), apoA-II (SEQ ID NO:2), apoB-100 (SEQ ID NO:3), Lp(a) (SEQ ID NO:4), apoC-I (SEQ ID NO:5), and apoC-III (SEQ ID NO:6), and peptides derived therefrom, may be used as biomarkers for CAD, which are present at a differential level in CAD subjects as compared to normal control subjects. Peptide fragments derived from SEQ ID NOS: 1, 2, 3, 4, 5, and 6 may also be used as biomarkers, such as peptides from about 4 amino acids to at least about 20 amino acids or more. Representative peptide fragments that may be used as biomarkers in which an increased amount of the biomarker in $HDL_2$ is indicative of the presence or risk of CAD include the peptides with positive regression vector values shown in TABLE 3 and TABLE 4. Representative peptide fragments that may be used as biomarkers in which a decreased amount of the biomarker in $HDL_2$ is indicative of the presence or risk of CAD include the peptides with negative regression vector values shown in TABLE 3 and TABLE 5.

The presence and/or amount of the two or more HDL-associated biomarkers in a biological sample comprising total HDL, or a subfraction thereof, may be determined using any suitable assay capable of detecting the amount of the one or more biomarkers. Such assay methods include, but are not limited to, mass spectrometry, liquid chromatography, thin layer chromatography, fluorometry, radioisotope detection, affinity detection, and antibody detection. Other detection paradigms may optionally be used, such as optical methods, electrochemical methods, atomic force microscopy, and radio frequency methods (e.g., multipolar resonance spectroscopy). Optical methods include, for example, microscopy, detection of fluorescence, luminescence, chemiluminescence, absorbance, reflectance, and transmittance.

In one embodiment, the presence and amount of one or more HDL-associated biomarkers is determined by mass spectrometry. In accordance with this embodiment, biological samples may be obtained and used directly, or may be separated into total HDL or an $HDL_2$ subfraction. The HDL-associated proteins are digested into peptides with any suitable enzyme such as trypsin, which cleaves adjacent to lysine (K) or arginine (R) residues in proteins. The peptides are then analyzed by a mass spectrometry method such as MALDI-TOF-MS or M/MS (solid phase), liquid chromatography (LC)-MS or MS/MS, μLC-ESI-MS/MS, and iTRAQ™ ICAT, or other forms of isotope tagging. Any suitable method may be used for differential isotope labeling of proteins and/or peptide, such as the use of a compound or isotope-labeled compound that reacts with an amino acid functional group. Label-specific fragment ions allow one to quantify the differences in relative abundance between samples. For example, one useful approach to achieve quantitative results is the use of MALDI TOF/TOF or QTOF mass spectrometers and iTRAQ™, a commercially available stable isotope labeling system (Applied Biosystems, Foster City, Calif.). The iTRAQ™ labeling system allows selective labeling of up to four different samples which are distinguished from one another in the mixture by MS/MS analysis.

By way of representative example, the method of MALDI-TOF-MS/MS involves the following steps. The samples are prepared and separated with fluidic devices, such as microfluidic devices, and spotted on a MALDI plate for laser-desorption ionization. Mass spectra are taken every few seconds, followed by isolation of the most intense peptide ions, or the peptide ions of interest (e.g., one derived from specific peptides), fragmentation by collisions with an inert gas, and recording of a mass spectrum of the fragments. This fragment mass spectrum, known as MS/MS spectrum, tandem mass spectrum, or $MS^2$ spectrum, consists mainly of N- and C-terminal fragments of the peptide ions at the amide bonds, called b ions and y ions, respectively. The spectra are then matched to sequence databases, as further described in Example 3.

In a typical application of MS analysis, proteins in a biological sample are reduced, alkylated, digested into peptides with trypsin, and analyzed using multidimensional liquid chromatography and tandem mass spectrometry (MS/MS). Tryptic peptides are then subjected to multidimensional chromatography in concert with MS/MS analysis. In multidimensional chromatography, the first chromatographic dimension typically involves separation of digested peptides on a strong cation exchange column. The peptides are then typically separated through a reverse-phase column with increasing concentrations of acetonitrile and then introduced into the source of the mass spectrometer or fractionated directly onto a MALDI sample plate. Tandem mass spectra may be acquired in the data-dependent mode on an ion-trap, QTOF or MALDI-TOF/TOF instrument. The most abundant peaks from a survey scan are submitted to tandem MS analysis. In other applications, peaks that differ in intensity between samples of interest (e.g., a control population of apparently healthy subjects and subjects with established CVD) are selected from the MS or MS/MS spectra by a suitable method such as pattern recognition, cluster analysis, or relative abundance (see Rocke, D. M, Semin Cell Dev Biol 15:703-13, 2004; Ghazalpour, A., et al., Lipid Res 45:1793-805, 2004). The collection of tandem mass spectra may be submitted for a database search against a database (e.g., the Human International Protein Index (IPI) database, using the SEQUEST search engine (see Kersey, P. J., et al., "The International Protein Index: An Integrated Database for Proteomics Experiments," Proteomics 4:1985-1988, 2004)), using software programs such as PeptideProphet, (Nesvizhskii, A. I., et al., Anal. Chem. 75:4646-4658, 2003) and ProteinProphet (Yan, W., et al., Mol. Cell. Proteomics 3:1039-1041, 2004) in order to refine peptide and protein identification.

To achieve semiquantitative results, protein abundance is estimated by the number of MS/MS spectra, the number of peptides detected, or by the percent of the protein sequence covered in the analysis. Quantitative results can be obtained with ICAT isotope tagging, iTRAQ™ isotope labeling, or other modifications or peptides involving stable isotopes. Label-specific ions or fragment ions allow quantification of differences between samples based on their relative abundance.

Mass spectrometry detection methods may include the use of isotope-labeled peptides or proteins. In accordance with one example of this detection method, as described by Zou, H., et al., Cell 107:715-726, 2001, a tryptic peptide is chosen from a protein of interest. The tryptic peptide is then synthesized to incorporate one or more stable isotope-labeled amino acids. The native peptide and the synthetic-labeled peptide share physical properties including size, charge, hydrophobicity, ionic character, and amenability to ionization. When mixed, they elute together chromatographically, migrate together electrophoretically, and ionize with the same intensity. However, they differ in molecular weight from as little as 1 to over 10 Daltons, depending on which stable isotope amino acid is chosen for incorporation. The native peptide and the synthetic peptide are easily distinguishable by mass spectrometry. The synthetic peptide is used in an assay by adding a known amount of the synthetic peptide to a biological sample. In another example of this detection method, an isotope-labeled protein is prepared by a suitable method, such as by using a bacterial expression system and growing the bacteria on medium enriched with 15N-Nitrate or other isotope-labeled nutrients. The isotope-labeled peptide or protein is added to the sample containing native proteins and the mixture is then digested and analyzed by mass spectrometry as described herein. Extracted ion chromatograms or selected ion chromatograms or peak ratios in a full scan mass spectrum are then generated for the native peptide and the synthetic peptide. The quantity of the native peptide is then calculated using ratios of ion current or peak ratios.

Another detection method that utilizes labeled peptide fragments is isotope-coded affinity tagging (ICAT). This technique, as described in Gygi, S. P., et al., Nature Biotech. 17:994-999, 1999, involves the use of isotope tags that covalently bind to specific amino acids (cysteines) within a protein of interest. For example, the tag may contain three functional elements including a biotin tag (used during affinity capture), an isotopically encoded linker chain (such as an ether linkage with either eight hydrogens or eight deuteriums), and the reactive group, which binds to and modifies the cysteine residues of the protein. The isotope tag is used in an assay by labeling a control sample with the light version of the tag and labeling a test sample with the heavy version of the tag. The two samples are then combined, enzymatically digested, and the labeled cysteinyl residues may be captured using avidin affinity chromatography. The captured peptides are then analyzed by mass spectrometry, which can determine the relative abundance for each peptide-pair.

In another embodiment, antibodies are used in an immunoassay to detect one or more biomarkers in accordance with the method of this aspect of the invention. Such immunoassays may comprise an antibody to one or more of the biomarkers. The antibody is mixed with a sample suspected of containing the biomarker and monitored for biomarker-antibody binding. For example, the biomarker can be detected in an enzyme-linked immunosorbent assay (ELISA), in which a biomarker antibody is bound to a solid phase, such as a chip, and an enzyme-antibody conjugate is used to detect and/or quantify the biomarker(s) present in a sample.

In another aspect, the present invention provides a method of screening a mammalian subject to determine if the subject is at risk to develop, or is suffering from, or is recovering from a cardiovascular disease, the method comprising detecting an alteration in the conformational structure of apoA-I present in the HDL subfraction of a biological sample obtained from the test subject in comparison to a reference standard, wherein a difference in the conformation of the apoA-I between the biological sample from the subject and the reference standard is indicative of the presence or risk of cardiovascular disease in the subject.

In order to conduct sample analysis, a biological sample containing HDL is provided to be screened. Any HDL containing sample may be utilized with the methods described herein, including but not limited to whole blood or blood fractions (e.g., serum), bodily fluid, urine, cultured cells, biopsies or other tissue preparations. In some embodiments, the biological samples include total HDL (density=about 1.06 to about 1.21 g/mL) or protein complexes that are isolated in this density range. In some embodiments, an $HDL_2$ subfraction (density=about 1.06 to about 1.125 g/mL) is isolated from the biological sample prior to analysis. In some embodiments, the HDL subfraction may be isolated by affinity isolation with polyclonal antibodies against apoA-I, the major protein in HDL or with polyclonal antibodies raised against other HDL associated proteins.

As described in Example 5, and shown in FIG. 7, it was determined that two tryptic peptides originating from N-terminal regions of apoA-I were significantly increased in the HDL subfraction of CAD subjects as compared to normal controls, while one tryptic peptide originating from the C-terminal region of apoA-I was significantly decreased. Although these N-terminal and C-terminal peptides are distant in the apoA-I sequence, when mapped to the double-belt model of the lipid-associated HDL particle apoA-I (Davidson, W. S, et al., *J. Biol. Chem.* 282(31):22249-22253, 2007, or the spherical HDL particle apoA-I model, the peptides displaying significant changes in CAD subjects were found to be in close proximity, as discussed in Example 5.

The conformation of apoA-I may be determined using any suitable method, such as by digesting the HDL subfraction of the biological sample with trypsin, followed by mass spectrometry analysis to measure the presence and/or amount of the tryptic fragments of apoA-I as compared to a reference standard, such as apoA-I isolated from normal control subjects. For example, the reference standard could be an exogenous isotopically labeled apoA-I which serves as an internal reference to which the intensity of individual peptides derived from apoA-I from the HDL subfraction of the biological sample would be related by a first ratio (i.e., apoA-I peptide from biological test sample/apoA-I peptide from reference standard). This first ratio would then be compared to a second ratio (i.e., apoA-I peptide from healthy control sample/apoA-I peptide from reference standard) to detect a difference in the amount of apoA-I peptides in the tested sample relative to the expected ratio in a healthy control sample, thereby indicating an altered apoA-I conformation.

In another example, the conformation of apoA-I may be determined by circular dichroism (CD), or with a monoclonal antibody that specifically detects the altered conformation of apoA-I. Methods of generating an antibody specific to an altered conformation of apoA-I are well known in the art, for example see Marcel, Y. L., et al., "Lipid Peroxidation Changes the Expression of Specific Epitopes of Apolipoprotein A-I," *J. Biol. Chem.* 264(33):19942-50, Nov. 25, 1989; Milthorp P, et al., "Immunochemical characterization of apolipoprotein A-I from normal human plasma. In vitro modification of apo A-I antigens," *Arteriosclerosis* 6(3):285-96, May-June 1986; Marcel, Y. L., et al, "Monoclonal antibodies and the characterization of apolipoprotein structure and function," *Prog Lipid Res* 23(4):169-95, 1984; and Weech, P. K., et al., "Apolipoprotein A-I from normal human plasma: definition of three distinct antigenic determinants," *Biochim Biophys Acta* 835(2):390-401, Jul. 9, 1985., and Marcel Y. L. et al., "The epitopes of apolipoprotein A-I define distinct structural domains including a mobile middle region," *J. Biol. Chem.* 266(6):3644-53, 1991.

In another aspect, the invention provides a method for diagnosing and/or assessing the risk of CAD in a subject, comprising determining changes in a biomarker profile comprising the relative abundance of at least one, two, three, four, five, ten or more biomarkers present in the HDL fraction of a biological sample from a test subject as compared to the predetermined abundance of the at least one, two, three, four, five, ten or more biomarkers from a reference population of apparently healthy subjects. The biomarkers are selected from biomarkers set forth in TABLE 3, TABLE 4, and TABLE 5. The biomarker profile may optionally include an internal reference standard that is expected to be equally abundant in subjects with CAD and apparently healthy subjects.

In another aspect, the present invention provides a method for determining the efficacy of a treatment regimen for treating and/or preventing CAD by monitoring a measurable feature of at least two biomarkers selected from the group consisting of apoA-I, apoA-II, apoB-100, Lp(a), apoC-I, and apoC-III, combinations or portions and/or derivatives thereof in a subject during treatment for CAD. The treatment for CAD varies depending on the symptoms and disease progression. The general treatments include lifestyle changes, medications, and may include surgery. Lifestyle changes include, for example, weight loss, a low saturated fat, low cholesterol diet, reduction of sodium, regular exercise, and a prohibition on smoking. Medications useful to treat CAD include, for example, cholesterol-lowering medications, antiplatelet agents (e.g., aspirin, ticlopidine, clopidogrel), glycoprotein IIb-IIIa inhibitors (such as abciximab, eptifibatide or tirofiban), or antithrombin drugs (blood-thinners such as heparin) to reduce the risk of blood clots. Beta-blockers may be used to decrease the heart rate and lower oxygen use by the heart. Nitrates, such as nitroglycerin, are used to dilate the coronary arteries and improve blood supply to the heart. Calcium-channel blockers are used to relax the coronary arteries and systemic arteries and thus reduce the workload for the heart. Medications suitable for reducing blood pressure are also useful to treat CAD, including ACE inhibitors, diuretics, and other medications.

The treatment for cardiovascular disease may include surgical interventions such as coronary angioplasty, coronary atherectomy, ablative laser-assisted angioplasty, catheter-based thrombolysis, mechanical thrombectomy, coronary stenting, coronary radiation implant, coronary brachytherapy (delivery of beta or gamma radiation into the coronary arteries), and coronary artery bypass surgery.

In another aspect, the present invention provides assays and kits comprising one or more detection reagents for determining susceptibility or presence of cardiovascular disease in a mammalian subject based on the detection of at least one measurable feature of at least one biomarker in a biological sample, an HDL subfraction thereof, or a complex containing apoA-I or apoA-II isolated from the biological sample. The biomarker is detected by mixing a detection reagent that detects at least one biomarker associated with CAD with a sample containing HDL-associated proteins (either an HDL subfraction or a complex containing apoA-I or apoA-II) and monitoring the mixture for detection of the biomarker with a suitable detection method such as spectrometry, immunoassay, or other method. In one embodiment, the assays are provided as a kit. In some embodiments, the kit comprises detection reagents for detecting at least two, three, four, five, ten or more HDL-associated biomarkers in biological samples from a test subject.

The kit also includes written indicia, such as instructions or other printed material for characterizing the risk of CAD based upon the outcome of the assay. The written indicia may include reference information or a link to information regarding the predetermined abundance of the at least one, two, three, four, five, ten or more HDL-associated biomarkers from a reference population of apparently healthy subjects and an indication of a correlation between the abundance of one or more HDL-associated biomarkers and the risk level and/or diagnosis of CAD.

The detection reagents may be any reagent for use in an assay or analytical method, such as mass spectrometry, capable of detecting at least one measurable feature of at least one biomarker selected from the group consisting of apoA-I, apoA-II, apoB-100, Lp(a), apoC-I, and apoC-III. In another embodiment, the detection reagents include proteins with peptides identical to those of apoA-I, apoA-II, apoB-100, Lp(a), apoC-I, and apoC-III, such as peptides provided in TABLE 3. A variety of protocols for measuring the relative abundance of the biomarkers may be used, including mass spectrometry, ELISAs, RIAs, and FACs, which are well known in the art.

In one embodiment, the detection reagent comprises one or more antibodies which specifically bind one or more of the biomarkers provided in TABLE 3, TABLE 4, or TABLE 5 that may be used for the diagnosis and/or prognosis of CAD characterized by the relative abundance of the biomarker in the serum, or an HDL subfraction thereof. Standard values for protein levels of the biomarkers are established by combining biological samples taken from healthy subjects. Deviation in the amount of the biomarker between control subjects and CAD subjects establishes the parameters for diagnosing and/or assessing risk levels, or monitoring disease progression. The biomarkers and fragments thereof can be used as antigens to generate antibodies specific for the CAD biomarkers for use in immunodiagnostic assays. Purified samples of the biomarkers comprising the amino acid sequences shown in TABLE 3, TABLE 4, and TABLE 5 may be recovered and used to generate antibodies using techniques known to one of skill in the art.

In another embodiment, the detection reagent comprises isotope-labeled peptides, such as one or more of the peptides described in TABLE 3, TABLE 4, and TABLE 5 that correspond to the biomarker to be detected. In accordance with this embodiment, the kit includes an enzyme, such as trypsin, and the amount of the biomarker in the tryptic digest of the sample is then quantified by isotope dilution mass spectrometry. The labeled peptides may be provided in association with a substrate, and the assay may be carried out in a multiplexed format. In one embodiment, a multiplexed format includes isotope-labeled peptides for at least two or more of the HDL-associated biomarkers described herein that are enriched in HDL of subjects with established CAD. The peptides are quantified of all the HDL-associated peptides in a biological sample obtained from a test subject using a technique such as isotope dilution mass spectrometry. The detection and quantification of multiple HDL-associated biomarker proteins may be used to increase the sensitivity and specificity of the assay to provide an accurate risk assessment and/or diagnosis of the presence of CAD in the test subject.

In one embodiment of the kit, the detection reagent is provided in association with or attached to a substrate. For example, a sample of blood, or HDL subfraction thereof, may be contacted with the substrate, having the detection reagent thereon, under conditions that allow binding between the biomarker and the detection reagent. The biomarker and/or the detection reagent are then detected with a suitable detection method. The substrate may be any suitable rigid or semi-rigid support including membranes, filters, chips, slides, wafers, fibers, magnetic or nonmagnetic beads, gels, tubing, plates, polymers, microparticles, and capillaries. The substrate can have a variety of surface forms, such as wells, trenches, pins, channels, and pores to which the polypeptides are bound. For example, a chip, such as a biochip, may be a solid substrate having a generally planar surface to which a detection reagent is attached. For example, a variety of chips are available for the capture and detection of biomarkers, in accordance with the present invention, from commercial sources such as Ciphergen Biosystems (Fremont, Calif.), Packard BioScience Company (Meriden, Conn.), Zyomyx (Hayward, Calif.), and Phylos (Lexington, Mass.). An example of a method for producing such a biochip is described in U.S. Pat. No. 6,225,047. The biomarkers bound to the substrates may be detected in a gas phase ion spectrometer. The detector translates information regarding the detected ions into mass-to-charge ratios. Detection of a biomarker also provides signal intensity, thereby allowing the determination of quantity and mass of the biomarker.

The following examples merely illustrate the best mode now contemplated for practicing the invention, but should not be construed to limit the invention.

Example 1

This example demonstrates that subjects may be successfully classified as normal control or coronary artery disease (CAD) subjects by analyzing the proteomic profile of $HDL_2$ tryptic peptides using matrix-assisted laser desorption ionization (MALDI) time-of-flight (TOF) tandem mass spectrometry (MALDI-TOF-MS) and subjecting the results to principal component analysis (PCA), a well-established pattern recognition method.

Rationale:

The overall approach in this study was to isolate HDL2 from control and CAD subjects, analyze a tryptic digest of HDL proteins by MALDI-TOF-MS, and use pattern recognition of the full scan mass spectra to classify subjects as either CAD subjects or control subjects.

Methods:

Sample isolation and preparation: All protocols involving human subjects were approved by the Human Studies Committees at the University of Washington. Blood samples were collected from 20 apparently healthy adult males and from 18 male patients with established CAD after an overnight fast. Blood samples were anticoagulated with EDTA. All subjects were male and matched for age and HDL cholesterol (HDL-C) levels. The CAD subjects had documented vascular disease, with symptoms consistent with angina and abnormal Q waves on their EKG or at least one stenotic lesion (>50% occlusion on coronary angiography). These CAD subjects were clinically stable, at least three months had elapsed since their acute coronary syndrome, and they had not taken lipid-lowering drugs for the six weeks prior to blood collection. The control subjects were apparently healthy and had no known history of CAD, were not hyperlipidemic, had no family history of premature CAD, and were not receiving any lipid-lowering therapy. None of the control subjects smoked cigarettes, had liver or renal disease, were diabetic, or had received lipid-lowering medications for at least six weeks before blood was collected.

The clinical characteristics of the two subject populations are summarized below in Table 1.

TABLE 1

CLINICAL CHARACTERISTICS OF STUDY SUBJECTS

| Number | Status | Age (yr) | % Male | Cholesterol (mg/dl) | Triglycerides (mg/dl) | HDL-C (mg/dl) | LDL-C (mg/dl) |
|---|---|---|---|---|---|---|---|
| 20 | Control | 57 (6) | 100 | 197 (13) | 104 (29) | 42 (8) | 134 (14) |
| 18 | CAD | 57 (6) | 100 | 223 (27) | 146 (67) | 41 (8) | 160 (25) |

It is noted that although levels of plasma LDL and triglycerides were higher in the CAD subjects than in the control subjects, the two groups were otherwise well-matched for known risk factors for vascular disease.

HDL isolation: $HDL_2$ (d=1.063 to 1.125 g/mL) was isolated from plasma obtained from the blood samples by sequential density ultracentrifugation, according to the methods described in Mendez, A. J., et. al., *J. Biol. Chem.* 266: 10104-10111, 1991. Protein concentration of HDL was determined using the Bradford assay (BioRad, Hercules, Calif.) with albumin as the standard.

Tryptic Digestion: $HDL_2$ was digested for 60 minutes with trypsin (1:50 w/w trypsin/HDL, sequencing grade trypsin, Promega WI) in 100 mM ammonium bicarbonate buffer in 80% aqueous acetonitrile (Strader, M. B., et al., *Anal Chem* 78(1):125-134, 2006). Digestion was terminated by addition of trifluoroacetic acid (TFA) to 1% final concentration.

The protein concentration of the $HDL_2$ digest was adjusted to 100 ng/µL with matrix solvent (70% acetonitrile, 0.1% TFA), and 0.5 µl of the digest was deposited on a MALDI target plate. Dried spots were overlaid with 0.5 µL of MALDI matrix (5 mg/mL alpha-cyano-4-hydroxy-cinnamic acid (CHCA) in matrix solvent.

Mass spectrometric analysis. Mass spectra were acquired on a matrix-assisted laser desorption ionization (MALDI) time-of-flight (TOF) tandem mass spectrometer (Applied Biosystems 4700 Proteomics Analyzer), operated in the reflection mode. Raw spectra were: (i) baseline-corrected and centroided using algorithms supplied by the manufacturer (ABI 4700 Explorer software, version 3.5); and (ii) internally mass calibrated using 5 tryptic fragments of apolipoprotein AI (apoA-I). The centroided spectra were then exported, using T2Extractor 5 (http://www.proteomecommons.org/archive/1114637208624/) for further analysis. It was determined that internal calibration afforded mass accuracy better than 5 ppm across the acquisition mass range.

For pattern recognition analysis, a single mass spectrum was generated from at least 80 sub-spectra generated randomly from different sites across the sample spot, each sampled with 25 laser shots, for a total of 2,000 shots. To exclude low intensity and saturated sub-spectra, only those with an ion current ranging from 30 to $80 \times 10^4$ cps were used to produce the mass spectrum.

Figure 9A:
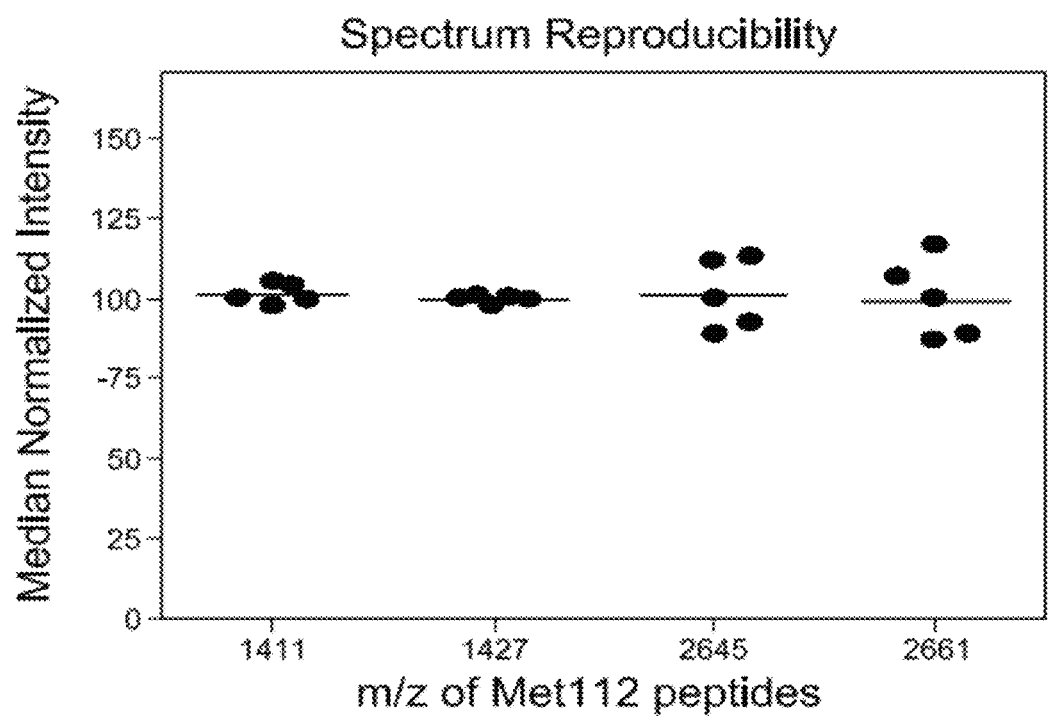
FIG. 9A graphically illustrates the reproducibility of the MALDI-TOF spectra with selected mass channels of Met112 peptides represented on the plot as median normalized intensities, as described in Example 1.
Figure 9B:
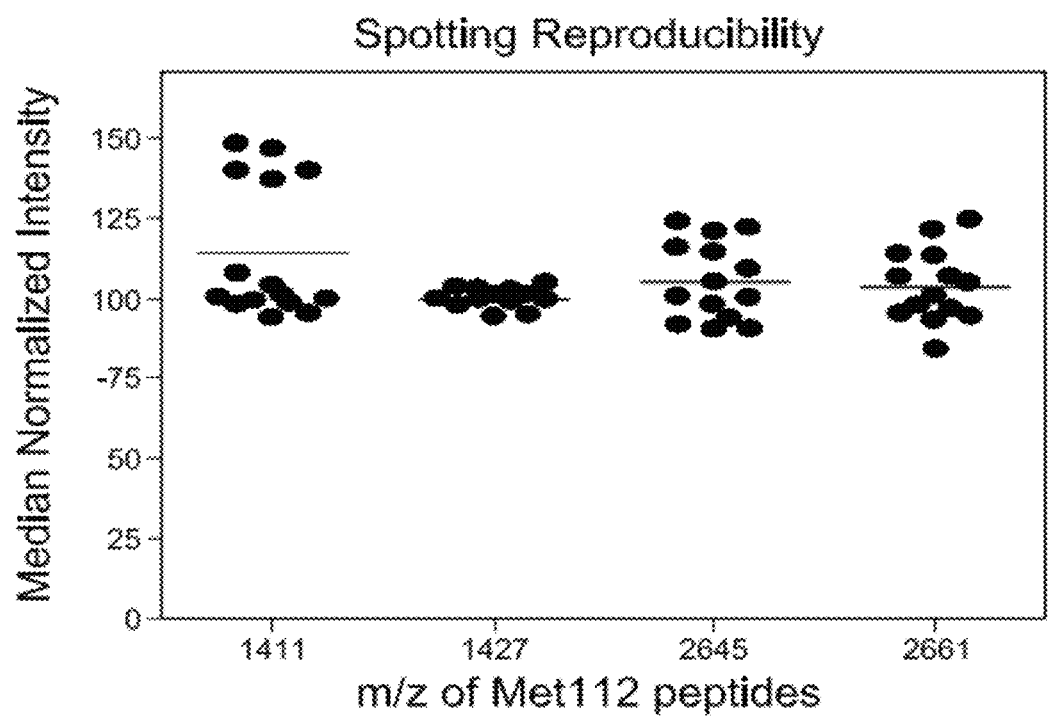
FIG. 9B graphically illustrates the reproducibility of the MALDI-TOF spectra of multiple spots of samples with selected mass channels of Met112 peptides represented on the plot as median normalized intensities, as described in Example 1.
Figure 9C:
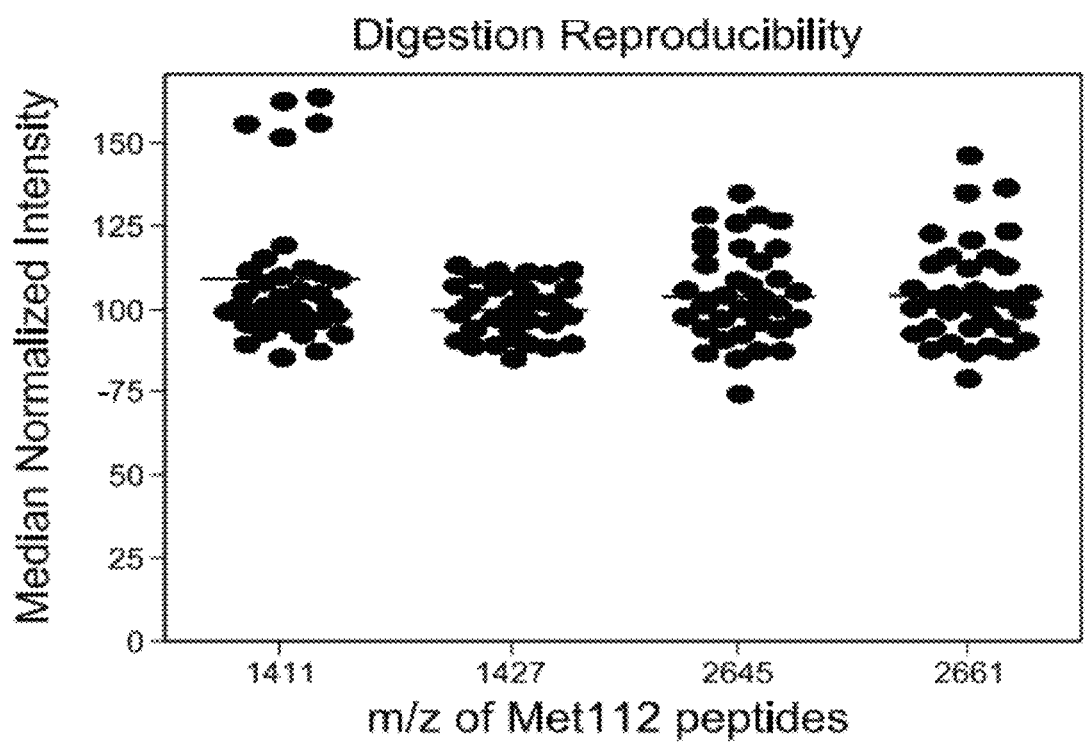
FIG. 9C graphically illustrates the reproducibility of a series of trypsin digestions carried out on the same day followed by MALDI-TOF spectra with selected mass channels of Met112 peptides represented on the plot as median normalized intensities, as described in Example 1.
Figure 9D:
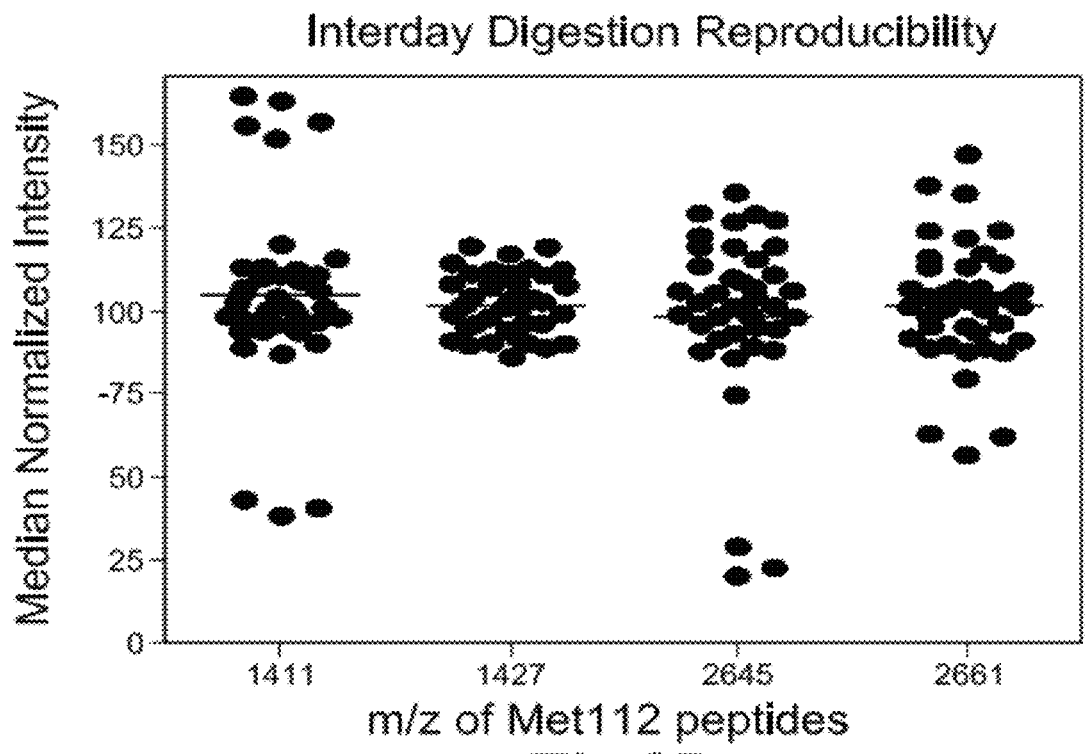
FIG. 9D graphically illustrates the reproducibility of a series of trypsin digestions carried out on different days followed by MALDI-TOF spectra with selected mass channels of Met112 peptides represented on the plot as median normalized intensities, as described in Example 1.

The analytical precision of the different steps was evaluated by acquiring multiple spectra from: (1) the same MALDI spot; (2) multiple MALDI spots of the same tryptic digest; (3) multiple tryptic digests of the same sample; and (4) tryptic digestion of the same sample carried out on different days. As shown in FIGS. 9A-D, precision analysis of individual mass channels showed excellent reproducibility of the spectra from the same spot (FIG. 9A), multiple spots (FIG. 9B), parallel digestions (FIG. 9C), and interday digestion (FIG. 9D). The data indicated that precision was improved by averaging several spectra from the same spot. Thus, for the PLS-DA analysis, four spectra from the same spot were averaged to generate a master spectrum used for subsequent analyses.

Processing of MS Spectra: MATLAB (version 7.0, Math-Works Inc.) was used for pattern recognition analysis. The full scan mass spectrum of each sample was transformed into a vector format suitable for pattern recognition based on linear algebra by placing the signals in bins that ranged from m/z 800 to m/z 5,000. To ensure that every spectrum had the same mass channels, bin sizes were increased linearly over this range to yield 45,920 bins or channels per spectrum. After binning, data vectors were aligned to remove single bin shifts that occurred when signals were near the bin boarder. A threshold of 1/10,000 of the spectrum's total signal was used to remove baseline noise, and the spectra were aligned. For PLS-DA the data were separated into calibration and test sets prior to preprocessing to avoid overfitting. After alignment and filtering, 2,338 channels contained signals.

Figure 8:
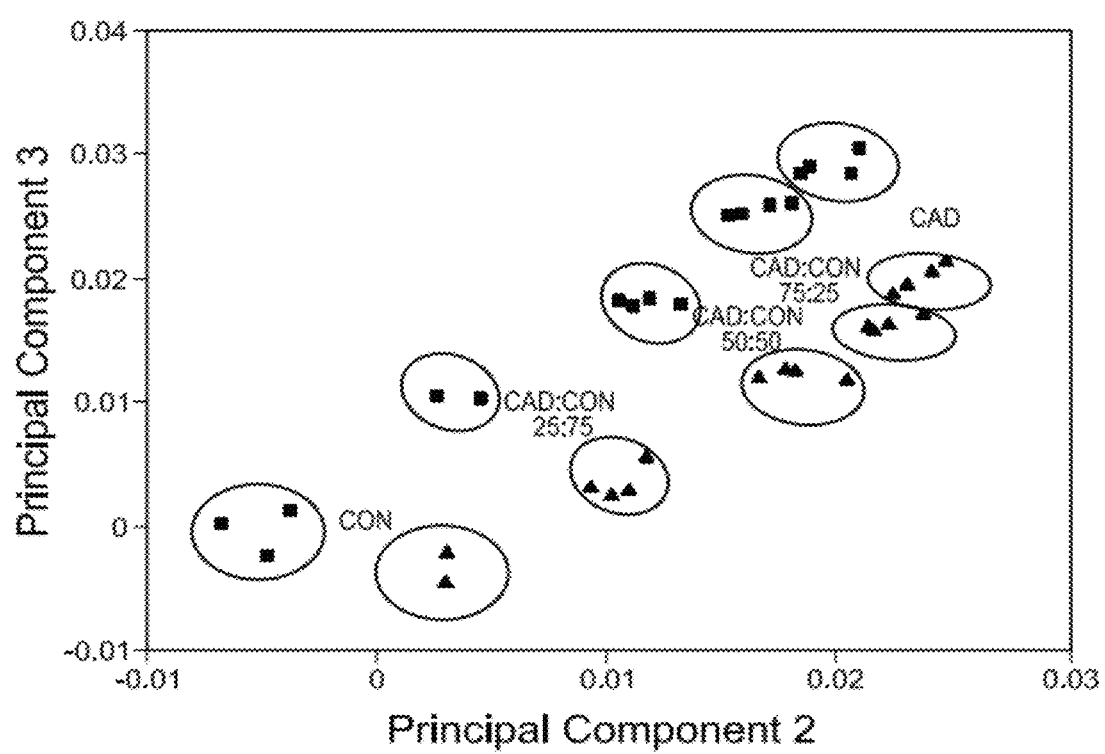
FIG. 8 graphically illustrates the results of principle component analysis (PCA) of the average mass spectra from $HDL_2$ isolated from 3 control and 3 CAD subjects mixed in protein ratios (w/w) of 1:0, 1:3, 1:1, 3:1, and 0:1, digested with trypsin, and subjected to MALDI-TOF-MS (for simplicity only two pairs are shown in FIG. 8), as described in Example 1.

PCA Analysis: Processed MS spectra were then subjected to principal component analysis (PCA) and PLS-DA (Beebe, K. R., et al., *Chemometrics: A practical guide*. New York: Wiley—Interscience; 1998; and International Publication No. WO2006/083852 incorporated by reference herein in its entirety). PCA was used to assess the reproducibility of MALDI plate spotting and digestion and the sensitivity of MALDI-TOF-MS to changes in HDL protein composition. The latter was tested by mixing variable amounts of $HDL_2$ isolated from CAD and control subjects, as shown in FIG. 8.

Validation of the Pattern Recognition Model: In order to test the ability of pattern recognition to distinguish between CAD and control HDL, PCA analysis was performed after mixing variable proportions of $HDL_2$ isolated from control and CAD subjects. Mass spectra of 6 pairs of randomly chosen CAD and control samples were mixed in ratios of 1:0, 1:3, 1:1, 3:1, and 0:1. In separate experiments, blinded test samples from CAD or control subjects mixed at the same ratios were also included for the study.

Results:

PCA is a powerful linear algebraic technique for identifying factors that differentiate populations in a complex data set (Martens, H., et al., *Multivariate Calibration*. New York: John Wiley & Sons, 1989; Marengo, E., et al., *Proteomics* 5(3):654-666 (2005); Lee, K. R., et al., *Proteomics* 3(9): 1680-1686 (2003); Natale, C. D., et al., *Biosensors and Bioelectronics* 18(10):1209-1218 (2003)). Importantly, this unsupervised data reduction method creates pattern recognition models without a priori assumptions regarding relationships between individual samples, (Beebe, K. R., et al., *Chemometrics: A practical Guide*. New York: Wiley-Interscience 1998).

PCA was initially used to test the ability of pattern recognition to distinguish between CAD and control HDL after mixing variable proportions of $HDL_2$ isolated from control and CAD subjects. The results of this analysis are shown in FIG. 8, where the square symbols and triangle symbols represent different pairs of CAD and control samples mixed at different ratios. As shown in FIG. 8, the bottom left corner of the graph shows control samples and the upper right corner of the graph shows CAD samples. Circles around the symbols represent a group of spectra from different mixed ratios. As shown in FIG. 8, the control and CAD subjects were well separated by PCA analysis. When the relative proportion of $HDL_2$ protein derived from control and CAD subjects in each sample was varied, there was a clear shift in the location of each sample on the PCA plot, as shown in FIG. 8, indicating that the method is sensitive to differences in the protein composition of HDL. Furthermore, the tight clustering of replicate spectra of the sample demonstrates the precision of this method.

These results demonstrate that subjects can be classified as CAD subjects based on the protein composition of their $HDL_2$ which differs substantially as compared to the protein composition of $HDL_2$ isolated from control subjects. These results further demonstrate that $HDL_2$ from subjects may be successfully classified into CAD or control subjects based on the MALDI-TOF-MS and PCA-based pattern profiling described. Use of tryptic peptides significantly enhances the precision and probability of identifying proteins and post-translational modifications and allows rapid analysis. Furthermore, as shown in FIG. 9, the tight clustering of replicate spectra demonstrates the precision of the analytical method. Thus, PCA provides a fast, simple, exploratory, and qualitative measure of differences in the protein cargo of $HDL_2$.

Example 2

This example demonstrates that subjects may be successfully classified into CAD or normal control subjects by analyzing tryptic digests of $HDL_2$-associated proteins by MALDI-TOF-MS using a highly precise pattern recognition linear algebraic algorithm, partial least squares determination analysis (PLS-DA).

Rationale:

Although PCA is a powerful technique for detecting and visualizing differences in patterns, it does not provide quantitative measures for predicting the disease status of individual samples. Therefore, another powerful linear algebraic technique, partial least squares discriminate analysis (PLS-DA) was used to develop a quantitative approach to classifying subjects with regard to CAD disease status. PLS-DA was selected rather than other pattern recognition techniques (such as K-nearest neighbor and Support Vector Machine) because it is well suited to analyzing the quantitative information in a mass spectrum which contains multiple independent signals as well as signals with significant redundancy and signals with incomplete selectivity.

Methods:

Sample isolation and preparation. $HDL_2$ fractions were isolated from the blood plasma of CAD and control subjects and digested with trypsin for 60 minutes, as described in Example 1. A sample from each subject was individually analyzed using MALDI-TOF MS as described in Example 1.

Processing of MS Spectra using Partial Least Squares Discriminate Analysis (PLS-DA) analysis. Matlab (version 7.0, Mathworks Inc.) was used for pattern recognition analysis. The full scan mass spectrum of each sample was transformed to a vector format suitable for pattern recognition based on linear algebra by placing the signals in bins that ranged from m/z 800 to m/z 5,000. To ensure that every spectrum had the same mass channels, bin sizes were increased linearly over this range to yield 45,920 bins or channels per spectrum. After binning, data vectors were aligned to remove single bin shifts that occurred when signals were near the bin boarder. A threshold of 1/10,000 of the spectrum's total signal was used to remove baseline noise, and the spectra were aligned. For PLS-DA, the data were separated into calibration and test sets prior to preprocessing to avoid overfitting. After alignment and filtering, 2,338 channels contained signals.

Preprocessed MS spectra were then subjected to PLS-DA. PLS-DA is a supervised pattern recognition technique. It uses two sets of data, such as training sets with defined groups (such as cases vs. controls) to "supervise" the creation of a pattern recognition model (Barker, M., et al., *Journal of Chemometrics* 16:166-173 (2003)), which is subsequently applied to a second test set of samples of unknown status. Thus, PLS-DA can be used to determine if a new proteomics sample belongs to previously defined sample classes. Furthermore, it can reveal relationships among sample classes and identify features distinguishing the classes, and ultimately the corresponding proteins. Most importantly, PLS-DA yields a single discriminant score that quantifies similarity of the tested spectrum with the model and can be used to predict the disease status of individual samples (CAD or control).

PLS-DA models were built with a dummy response matrix containing discrete numerical values (1 or −1) for each class as described in International Publication No. WO2006/083853. In the present analysis, "1" represented the CAD class and "−1" represented the control class. For each sample being classified, the PLS-DA model then produced a discriminant value, which was termed the "proteomics CAD risk score" or "ProtCAD" score. The ProtCAD risk scores thus generated were used to predict disease status of the remaining control and CAD subjects (validation group) as described in International Publication No. WO2006/083853, hereby incorporated by reference. To provide a quantitative estimate of the performance of the PLS-DA model, two approaches were used to provide a quantitative estimate of the performance: (1) Random permutation analysis; and (2) Leave-one-out analysis.

Random Permutation Analysis: When data from only a small number of subjects are used to build a complex pattern recognition model, predictions are often affected by the selection of the calibration subjects. Therefore, a permutation analysis was used to test the ProtCAD score's ability to predict disease status. In each step of this analysis, the subjects were assigned to two groups: a calibration group and a validation group, each composed of ten randomly selected control subjects and nine CAD subjects. The calibration group was used to build a PLS-DA model, which was then used to predict the ProtCAD score for each subject in the validation group. This process was repeated 7,777 times to determine the precision of the PLS-DA predictions, as described in International Publication No. WO2006/083853.

Receiver operating characteristics (ROC) curves: Non-parametric empirical receiver operating characteristic (ROC) curves were constructed from the ProtCAD risk score (Pepe, M. S., *The Statistical Evaluation of Medical Tests for Classification and Prediction*, New York, Oxford University Press, 2003). Sensitivity and specificity were calculated from the known class identity of each subject in the validation group. Area under the curve (AUC) calculations was determined using the trapezoidal rule (Fawcett, T., "An Introductory ROC Analysis," *Pattern Recognition Letters* 27:861-874, 2006). For each permutation, one ROC curve was generated, and by plotting the sensitivity (fraction of positive results) against specificity (the fraction of negative results), ROC quantitatively assessed the accuracy of the predictive test. A quantitative PLS-DA model based on full scan mass spectra of $HLD_2$ from a calibration group randomly selected subjects predicted CAD status in the validation group, with an average $ROC_{AUC}$ of 0.9. $ROC_{AUC}$ of 0.5 represents chance discrimination, whereas $ROC_{AUC}$ 1.0 represents perfect discrimination. For a CAD diagnostic test, an $ROC_{AUC}$ of 0.7-0.8 is generally considered acceptable, and values over 0.8 are considered excellent.

Leave-one-out ProtCAD prediction: In order to use the maximum number of available subjects, a leave-one-out approach was utilized to build a more powerful PLS-DA model, as described in International Publication No. WO2006/083853. The ProtCAD score for each subject was determined using a model built from the remaining subjects (e.g., 17 CAD and 19 controls). To predict the disease status of a subject, a ROC curve was first constructed and then the value of the ProtCAD score was compared to a threshold value corresponding to a selected sensitivity and selectivity on the ROC curve.

In preliminary experiments, it was determined that CAD predictions based on the entire mass spectrum outperformed predictions based on the ten most selective signals (as determined by PLS-DA, data not shown). Full spectrum PLS-DA can identify signals in regions normally associated with low selectivity and help identify outlier samples (e.g., problems with data acquisition from MS analysis, sample handling) or marked variations in sample protein composition (e.g., genetic variations in apoA-I, post-translational modifications). Such outliers would be overlooked by techniques that use only selected features of the spectrum. Therefore, all of the information in the full scan mass spectra was used to build models.

Results:

Two approaches were used to assess the ability of PLS-DA to distinguish the proteomic fingerprints of HDL isolated from control and CAD subjects. First, a PLS-DA model was built using data from randomly selected control and CAD subjects. Then the model was tested for its ability to predict disease status in a second set of subjects. The PLS-DA models were built with a dummy response matrix containing discrete numerical values for each class using ten control and nine CAD subjects (the calibration set) that were randomly selected from the 20 control and 18 CAD subjects. The PLS-DA model was then used to predict the disease status of the remaining ten control and nine CAD subjects (the validation set). For each sample in the validation set the approach produced a discriminant score, which was termed the "Proteomics CAD risk score" (ProtCAD risk score).

Random permutation analysis was used to provide a quantitative estimate of the performance of the PLS-DA model that was used to build the discriminant termed the Proteomics CAD risk score (ProtCAD risk score). The ProtCAD score was then used to predict the CAD status of the validation group (the remaining nine CAD and ten control subjects). A total of 7,777 random permutations were used to construct the ROC curve. FIG. 1 presents graphical results demonstrating the receiver operating characteristic (ROC) curve of the prediction of cardiovascular disease (CAD) status based on random permutation analysis. By plotting sensitivity (the fraction of true positive results, shown in the y-axis) against specificity (the fraction of true negative results, shown in the x-axis), the ROC curve quantitatively assesses the accuracy of a predictive test. As shown in FIG. 1, the average ROC curve shows an area-under-the-curve of 0.880±0.097 (mean, SD. N=7,777 iterations), indicating that PLS-DA analysis can predict disease status with high sensitivity and specificity.

Figure 2:
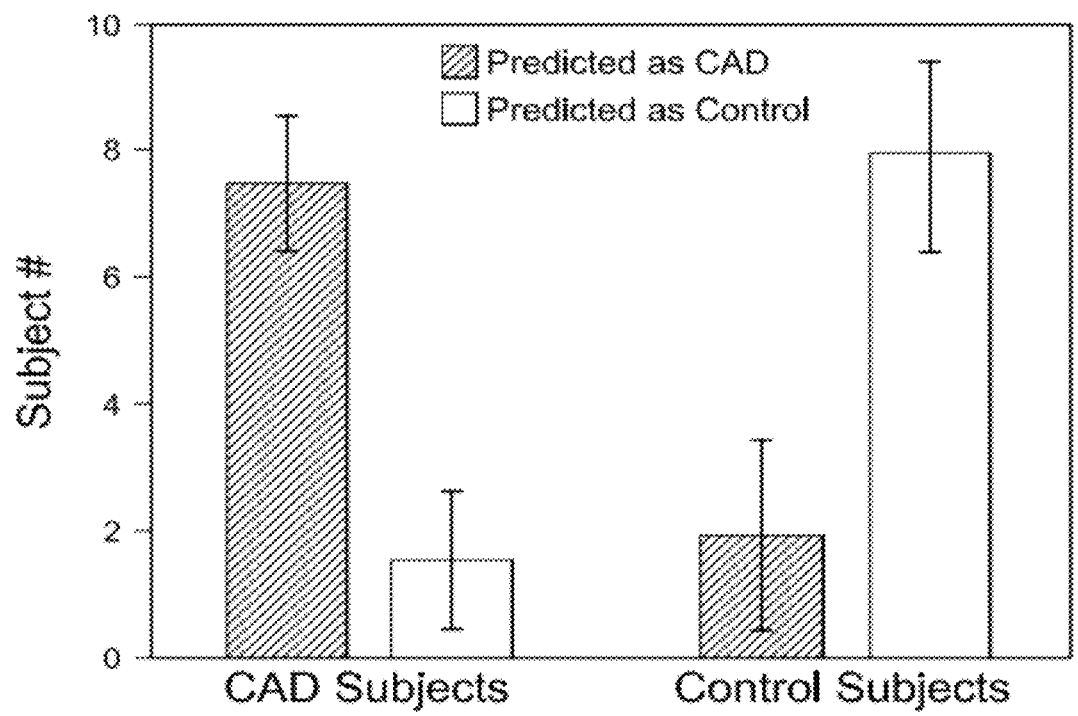
FIG. 2 graphically illustrates the prediction of CAD status by the proteomics CAD risk score "ProtCAD risk score" using a partial least squares discriminate analysis (PLS-DA) model built using a calibration group (as described in Example 2). Using a sensitivity of 80%, the ProtCAD risk score of each subject in the validation group at each permutation was used to predict their CAD status, as described in Example 2.

FIG. 2 graphically illustrates the prediction of CAD status by the proteomics CAD risk score "ProtCAD risk score" using a partial least squares discriminate analysis (PLS-DA) model built using a calibration group. Using a sensitivity of 80%, the ProtCAD risk score of each subject in the validation group at each permutation was used to predict their CAD status. The results in FIG. 2 demonstrate that the ProtCAD score generated using the PLS-DA model is able to distinguish CAD and control subjects with high selectivity (p-value of 0.0001%). Using a clinically acceptable sensitivity of 80%, (see Pepe, M. S., *The Statistical Evaluation of Medical Tests for Classification and Prediction*, New York: Oxford University Press, 2003), the average PLS-DA model predicted CAD status with 76% specificity, as shown in FIG. 2.

The level of specificity shown in FIG. 2 corresponds to an odds ratio of 12.7, i.e., the odds ratio of the PLS-DA model for predicting CAD status here was 12.7 at 80% sensitivity and 76% specificity. These results demonstrate the power of this analytical approach for identifying subjects at risk for CAD.

In the second approach, disease status was predicted by using PLS-DA models built with the leave-one-out method as described in International Publication No. WO2006/083853. This strategy allowed the use of all available subjects for the analysis, which would be expected to yield the strongest predictive model. After systematically leaving out one subject at a time from the calibration set, the subject's ProtCAD score was predicted using a model built from the remaining samples.

Figure 3:
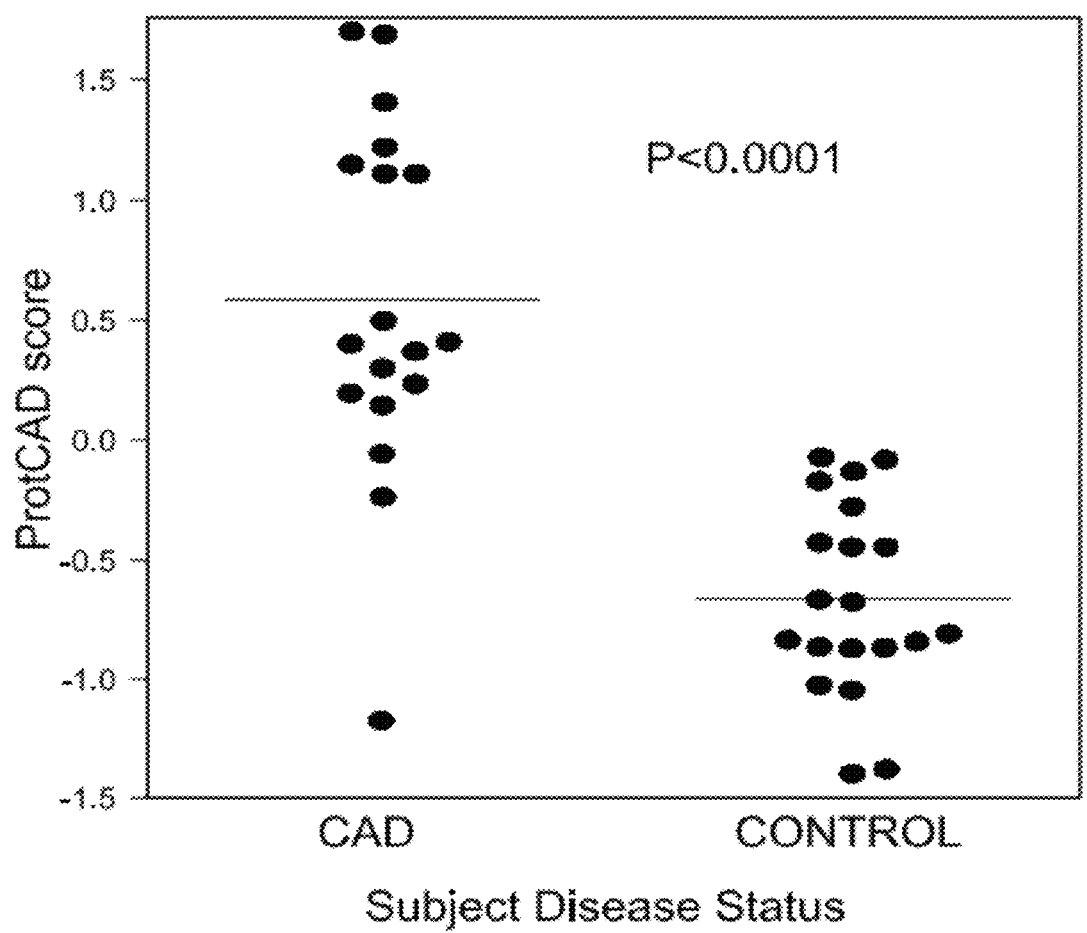
FIG. 3 graphically illustrates the power of the ProtCAD risk score to discriminate between the CAD samples and healthy control samples based on leave-one-out analysis. The ProtCAD risk score was derived from PLS-DA analysis of MALDI-TOF-MS mass spectra of HDL tryptic digests, using a leave-one-out experiment for all 18 CAD and 20 control subjects, as described in Example 2.
Figure 10A:
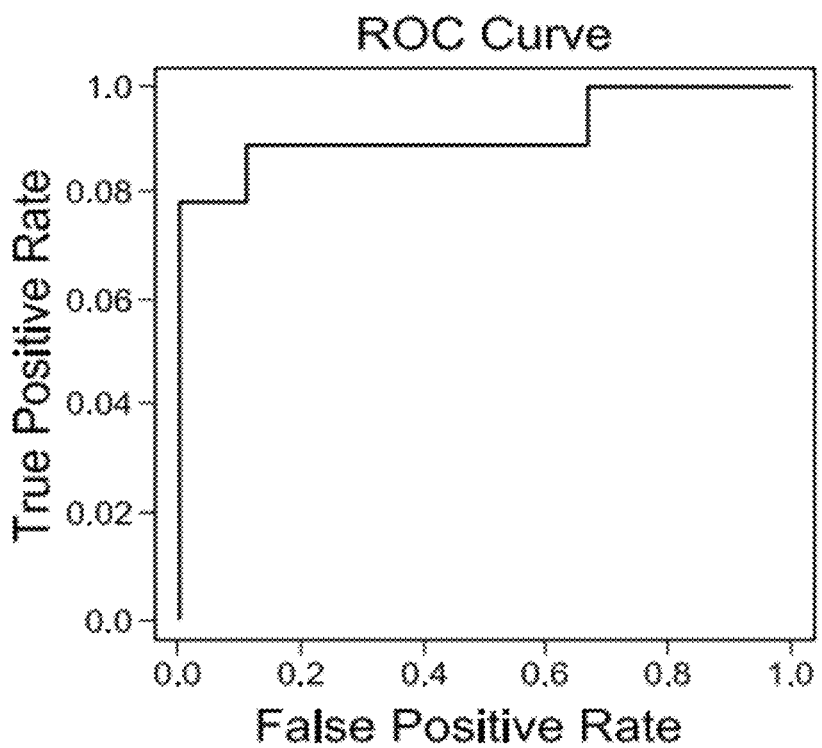
FIG. 10A graphically illustrates a receiver operating characteristic (ROC) curve constructed using a ProtCAD score based on a PLS-DA model built from a leave-one-out approach, demonstrating high selectivity (true positive rate=y axis) and high specificity (false positive rate=x axis), as described in Example 2.
Figure 10B:
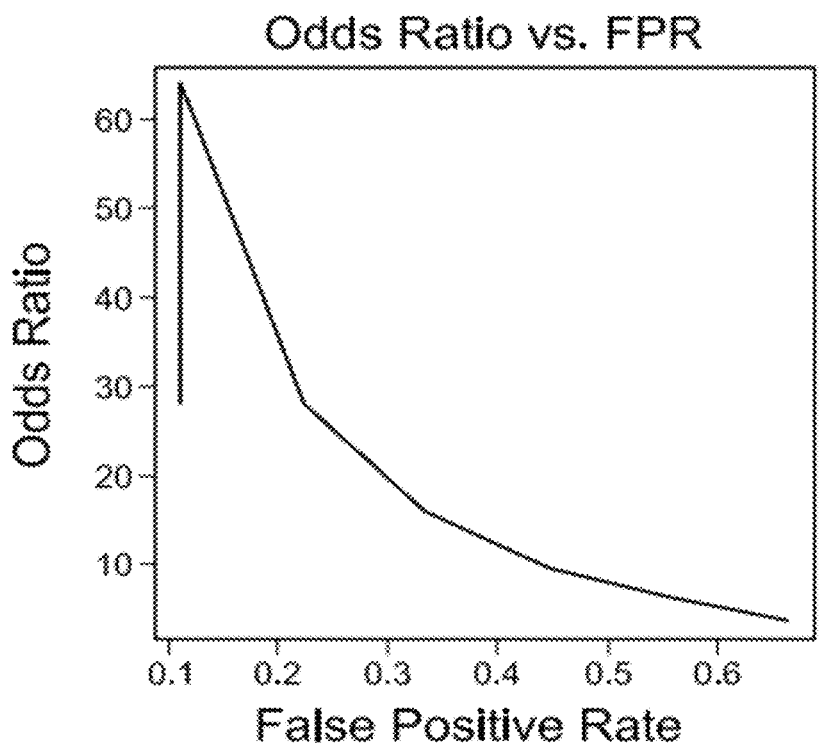
FIG. 10B graphically illustrates the odds ratio of the ProCAD score as a function of the false positive rate, demonstrating that at an 80% level of specificity (corresponding to a 90% sensitivity level as shown in FIG. 10A), the odds ratio was approximately 35, as described in Example 2.

FIG. 3 graphically illustrates the power of the ProtCAD risk score to discriminate between the CAD samples and healthy control samples based on leave-one-out analysis. The ProtCAD risk score was derived from PLS-DA analysis of MALDI-TOF-MS mass spectra of HDL tryptic digests, using a leave-one-out experiment for all 18 CAD and 20 control subjects. These ProtCAD scores distinguished the CAD and control subjects with high selectivity (p<0.0001), as shown in FIG. 3. Furthermore, the larger number of subjects in the calibration set improved diagnostic power. As shown in FIG. 10A, the ROC curve constructed for ProtCAD scores from the leave-one-out approach showed an area-under-the-curve of 0.94 and a maximum odds ratio of 68. From the leave-one-out ProtCAD risk score ROC curve, we determined a threshold corresponding to 90% sensitivity (ProtCAD threshold=− 0.06). Using this threshold, the model correctly classified 16 of 18 CAD subjects and 19 of 20 control subjects.

Therefore, these results demonstrate that pattern recognition analysis, when applied to MALDI-TOF-MS spectra of tryptic digests of $HDL_2$, clearly demonstrate differences in the HDL proteomic signature of apparently healthy subjects and CAD subjects. Moreover, a quantitative PLS-DA model based on full scan mass spectra of $HDL_2$ from a calibration group of randomly selected subjects predicted CAD status in the validation group, with an average $ROC_{AUC}$ of 0.9 ($ROC_{AUC}$ 0.5 represents chance discrimination, whereas $ROC_{AUC}$ 1.0 represents perfect discrimination).

For a CAD diagnostic test, an ROCAUC of 0.7 to 0.8 is generally considered acceptable, and values over 0.8 are considered excellent (see Pepe, M. S., *The Statistical Evaluation of Medical Tests for Classification and Prediction*, New York, Oxford University Press, 2003). Furthermore, the odds ratio of the PLS-DA model for predicting CAD status was 12.7 at 80% sensitivity and 76% specificity. When the model was built with data from a larger number of subjects using the leave-one-out method, the ProtCAD risk score distinguished subjects with an even higher odds ratio of 68. These results compare favorably with other single lipoprotein-associated risk factors identified in previous studies (Yusuf, S., et al., *Lancet*, 364(9438):937-952, 2004; Walldius, G., and I. Jungner, *J. Intern. Med.* 259(5):493-519, 2006; Walldius, G., and I. Jungner, *Curr. Opin. Cardiol.* 22(4):359-367, 2007).

The standard method for predicting CAD, the Framingham risk score, combines seven demographic, biochemical and medical factors to predict CAD risk (Wilson, P. W., et al., *Circulation* 97(18):1837-1847 (1998)). The Framingham risk scores $ROC_{AUC}$ ranges from 0.6-0.8 for predicting CAD risk over a ten year period. Its strongest predictors are age and sex, which are not modifiable risk factors. Moreover, LDL-C and HDL-C contribute little to the risk score in some models (Yusuf, S., et al., *Lancet* 364(9438):937-952, 2004; Walldius, G., et al., *Curr Opin Cardiol* 22(4):359-367, 2007; Walldius, G., et al., *J Intern Med* 259(5):493-519, 2006).

On the other hand, this example indicates that the $HDL_2$ isolated from CAD subjects with its characteristic proteome profile is faster and more accurate at predicting risk with a $ROC_{AUC}$ of 0.9.

Conclusion:

As demonstrated herein, the protein composition of the $HDL_2$ in subjects with CAD as well as the protein composition of $HDL_2$ isolated from control subjects are different. Differences in the protein profiles can be accurately and quantitatively measured using the two different approaches together with the PLS-DA algorithm. These observations also show that PLS-DA analysis can correctly and with high sensitivity predict the status of a subject as a CAD subject or a control subject.

The methods of proteomic fingerprinting of HDL by MALDI-TOF-MS offer a number of important advantages for building classification models. First, it has been demonstrated that HDL is causally linked to CAD pathogenesis. Second, the HDL proteome is much simpler than the plasma proteome (which has been estimated to contain >$10^4$ different proteins and peptides with relative concentrations ranging over 12 orders of magnitude), which greatly facilitates MS analysis. Third, the interrogation of tryptic digests significantly enhances the precision of the mass spectrometric measurements, and thereby increases the probability of identifying proteins and post-translational modifications. In contrast to the methods described herein, surface-enhanced laser desorption ionization (SELDI) MS analysis, which has been widely used for pattern recognition, typically samples intact proteins, which makes it difficult to identify the proteins responsible for informative signals in quantitative models. SELDI MS also has a limited mass range and low mass resolution, which bias detection of informative features toward degraded and low MW proteins. Finally, the high mass accuracy of MALDI-TOF-MS facilitates the subsequent identification of proteins and posttranslational modifications by tandem MS. MALDI-TOF-MS of tryptic digests also greatly improves the precision of signals, which is important for pattern recognition analysis.

Previous studies using shotgun proteomics to investigate the protein composition of $HDL_3$ using liquid chromatography in concert with electrospray ionization (ESI) to introduce peptides into the mass spectrometer (Vaisar, T., et al., *J. Clin. Invest.* 117(3):746-756 (2007)). In contrast, in the present study the peptides were ionized with MALDI. It is well established that ESI and MALDI ionize different classes of peptides with different efficiencies. For example, hydrophobic peptides are much more readily introduced into the gas phase by MALDI.

Example 3

This example describes the identification of proteins differentially present in $HDL_2$ subfractions isolated from normal control and CAD subjects by tryptic peptide analyses of $HDL_2$ fractions by tandem mass spectrometric (tandem MS) following PLS-DA based pattern recognition profiling.

Methods:

Sample isolation and preparation: $HDL_2$ fractions were isolated from normal control and CAD subjects as described earlier in Example 1. Tryptic digests of $HDL_2$ fractions were subjected to liquid chromatographic separation with direct application of the sample effluent from the liquid chromatograph onto a MALDI sample plate and subjected to MALDI-TOF/TOF tandem mass spectrometric analysis (LC-MALDI-TOF/TOF). Subjects were confirmed as either CAD or normal subjects by pattern recognition proteomic profiling of $HDL_2$ proteins using PLS-DA, as described in Example 2.

The PLS-DA models are characterized by regression vectors which indicate channels on the m/z axis of a mass spectrum that differentiate the two sample classes.

Figure 4:
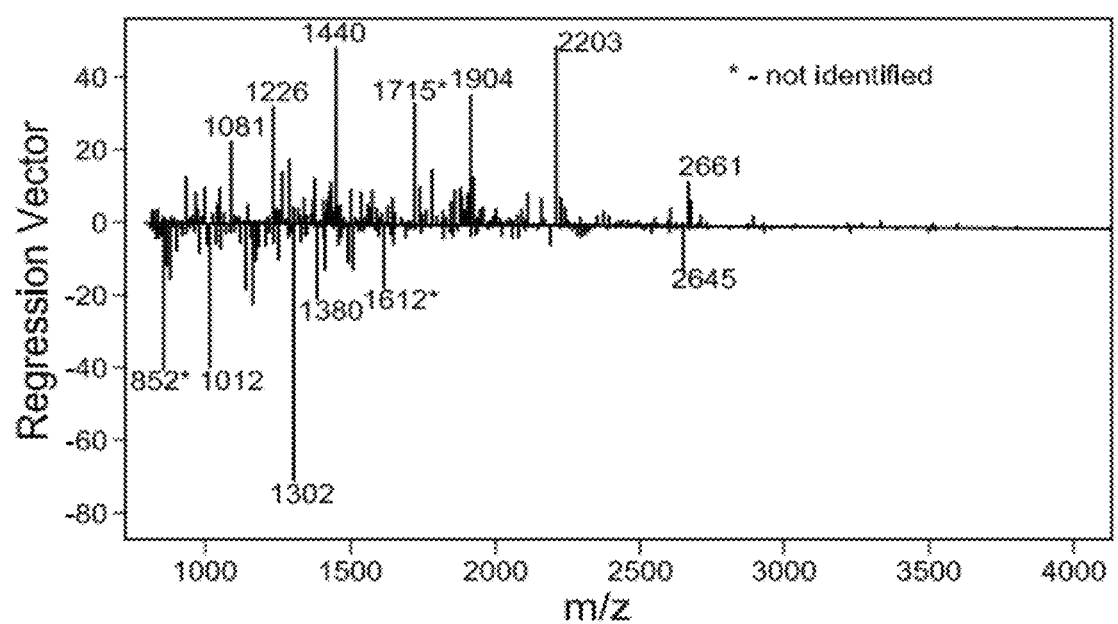
FIG. 4 graphically illustrates the PLS-DA regression vectors (y-axis) of the leave-one-out PLS-DA model that distinguish CAD and control subjects. The x-axis (m/z) represents mass channels of the MALDI-TOF mass spectrum. Positive and negative features on the regression vector indicate an increase and decrease, respectively, of the signals from CAD samples relative to control samples, as described in Example 3.

FIG. 4 graphically illustrates the PLS-DA regression vectors (y-axis) of the leave-one-out PLS-DA model that distinguish CAD and control subjects. The x-axis (m/z) represents mass channels of the MALDI-TOF mass spectrum. Positive and negative features on the regression vector indicate an increase and decrease of the signals from CAD samples (and therefore relative amount of peptide present) relative to control samples. Each mass channel in the regression vector that had significant differences between CAD and normal subjects was called an informative feature.

Channels in the regression vectors with positive values correspond to the peptides (and indirectly to the proteins) with increased relative abundance in CAD samples. Channels with negative values in the regression vector have decreased abundance in CAD samples. As shown in FIG. 4, a subset of 13 informative features were identified with the most significant increase or decrease in CAD subjects as compared to normal control subjects in a full scan mass spectrum that contributed to the ability to differentiate CAD subjects from normal subjects. The peptides associated with these informative features were identified by tandem MS using the MALDI-TOF/TOF analyzer capable of MS and MS/MS analysis interfaced with an off-line capillary liquid chromatograph and coupled with a MALDI plate spotter. As described in International Publication No. WO2006/083853, chromatographic information may be used to more strongly validate that the peptide identified is actually producing the observed peak in the regression vector.

Identification of significant features by Liquid-Chromatography (LC) matrix-assisted laser desorption ionization (MALDI): To identify features that were enriched or depleted in the mass spectra of HDL isolated from CAD subjects, CAD HDL tryptic digests were fractionated by liquid chromatography and the peptide digest was subjected to MS/MS analysis by MALDI-TOF/TOF. A tryptic digest of HDL was injected onto a trap column (NanoTrap C18, LC Packings), washed, and eluted onto an analytical capillary HPLC column (PepMap C18, LC Packings) using an Ultimate 300 HPLC (LC Packings Inc.). Separation was achieved by linear gradient 5-50% B over 40 minutes (A-5% aqueous can, 0.1% TFA, B-80% aqueous can, 0.1% TFA). The eluent from the column was mixed with matrix (CHCA, 5 mg/ml in 70% AcN) containing internal standard peptides and spotted on-line (Shimadzu Accuspot MALDI plate spotter) on a MALDI target plate. Targeted MS/MS analysis of selected peptide ions was based on informative mass features of HDL proteomics fingerprints that were identified in the PLS-DA analysis. Peptides were identified by MASCOT database search (v2.0, Matrix Science) against the human SwissProt protein database with the following parameters; trypsin cleavage with up to two missed cleavages, methionine oxidation variable modification, precursor tolerance 15 ppm, and fragment ion tolerance 0.2 Da. Peptide matches were only accepted if the MASCOT probability based Mowse score identified the peptide with a very high score indicating a match to the database with >99% confidence.

Results:

It was determined that the relative abundance of $HDL_2$ apolipoproteins was altered in CAD subjects compared to the controls.

One group of informative features arose from proteins in the $HDL_2$ fraction that were differentially abundant in CAD and control subjects. As shown in FIG. 4, informative features with positive regression vector values were observed at channels 1081, 1226, 1440, 1715*, 1904, 2203, and 2661 m/z in the CAD subjects relative to the control subjects, indicating that the peptides (and therefore proteins) represented by these regression vectors at these channels were more abundant in CAD subjects.

As further shown in FIG. 4, informative features with negative regression vector values were observed at channels 852*, 1012, 1302, 1380, 1612, and 2645 m/z in the CAD subjects relative to the control subjects, indicating that the peptides (and therefore proteins) represented by these regression vectors at these channels were reduced in CAD subjects as compared to normal control subjects.

TABLE 2 provides a set of informative biomarkers corresponding to features from FIG. 4 that were identified using the targeted LC-MALDI-TOF/TOF approach.

TABLE 2

BIOMARKERS IDENTIFIED AS PROGNOSTIC AND/OR DIAGNOSTIC INDICATORS OF CAD

| Protein | Refseq ID Numbers | SEQ ID NO: |
|---|---|---|
| apoA-I | NP_000030.1 | SEQ ID NO: 1 |
| apoA-II | NP_001634 | SEQ ID NO: 2 |
| apoB-100 | NP_000375 | SEQ ID NO: 3 |
| Lp(a) | NP_005568.1 | SEQ ID NO: 4 |
| apoC-I | NP_001636.1 | SEQ ID NO: 5 |
| apoC-III | NP_000031.1 | SEQ ID NO: 6 |
| SAA4 (serum amyloid A4-confirm) | NP_006503 | SEQ ID NO: 7 |
| apoE | NP_000032 | SEQ ID NO: 8 |

Targeted tandem MS analysis was carried out to identify the peptides corresponding to the informative features shown in FIG. 4. The results are shown in TABLE 3.

TABLE 3

PEPTIDES IDENTIFIED AS INFORMATIVE FOR CAD

| m/z | Magnitude in Regression Vector | Peptide | Protein | start-stop | SEQ ID NO |
|---|---|---|---|---|---|
| 861.5088 | -11.679 | ITLPDFR | apoB-100 | 2706-2712 | 9 |
| 999.5271 | -5.9951 | SVGFHLPSR | apoB-100 | 1325-1333 | 10 |
| 1012.6055 | -39.9366 | AKPALEDLR | apoA-I | 231-239 | 11 |
| 1013.5781 | -21.0822 | AKPALEDLR-I | apoA-I | 231-239 | 11 |
| 1014.5921 | -5.15 | AKPALEDLR-II | apoA-I | 231-239 | 11 |
| 1031.5333 | -5.700 | LSPLGEEMR | apoA-I | 165-172 | 12 |
| 1032.524 | -3.785 | LSPLGEEMR-I | apoA-I | 165-173 | 12 |
| 1033.5571 | 5.470 | LSPLGEEMR-II | apoA-I | 165-173 | 14 |
| 1033.5571 | 5.470 | LQAEAFQAR | apoE | 270-278 | 13 |
| 1047.4997 | -6.987 | LSPLGEEMoxR | apoA-I | 165-173 | 12 |
| 1048.5057 | -3.295 | LSPLGEEMoxR-I | apoA-I | 165-173 | 12 |
| 1049.5128 | -1.862 | LSPLGEEMoxR-II | apoA-I | 165-173 | 12 |
| 1081.6043 | 22.482 | LAAYLMLMR | apoB-100 | 559-567 | 15 |
| 1141.6155 | 2.912 | HINIDQFVR | apoB-100 | 2101-2109 | 16 |
| 1156.6456 | -3.813 | SKEQLTPLIK | apoA-II | 68-77 | 17 |
| 1156.6456 | -3.813 | SPAFTDLHLR | apoB-100 | 3980-3989 | 18 |
| 1157.6638 | -22.261 | LEALKENGGAR | apoA-I | 202-212 | 19 |
| 1157.6638 | -22.261 | SKEQLTPLIK-I | apoA-II | 68-77 | 17 |
| 1158.6367 | -15.025 | LEALKENGGAR-I | apoA-I | 202-212 | 19 |
| 1158.6367 | -15.025 | SKEQLTPLIK-II | apoA-II | 68-77 | 17 |
| 1159.6567 | -5.85 | LEALKENGGAR-II | apoA-I | 202-212 | 19 |
| 1159.6567 | -5.85 | SKEQLTPLIK-III | apoA-II | 68-77 | 17 |
| 1160.6312 | -0.846 | LEALKENGGAR-III | apoA-I | 202-212 | 19 |
| 1160.6312 | -0.846 | SKEQLTPLIK-IV | apoA-II | 68-77 | 17 |
| 1166.5888 | -8.57 | FRETLEDTR | apoB-100 | 2512-2520 | 20 |
| 1167.5691 | -5.47 | FRETLEDTR-I | apoB-100 | 2512-2520 | 20 |
| 1168.597 | -1.685 | FRETLEDTR-II | apoB-100 | 2512-2520 | 20 |
| 1169.579 | -10.437 | SLDEHYHIR | apoB-100 | 2211-2219 | 21 |
| 1170.6086 | -7.161 | SLDEHYHIR | apoB-100 | 2211-2219 | 21 |
| 1171.5924 | -1.733 | SLDEHYHIR | apoB-100 | 2211-2219 | 21 |
| 1178.6429 | -6.301 | VLVDHFGYTK | apoB-100 | 733-742 | 22 |
| 1179.6334 | -5.424 | VLVDHFGYTK-I | apoB-100 | 733-742 | 22 |
| 1199.6662 | -6.224 | VKSPELQAEAK | apoA-II | 52-62 | 23 |
| 1200.6743 | -4.688 | VKSPELQAEAK-I | apoA-II | 52-62 | 23 |
| 1201.6352 | -4.73 | VKSPELQAEAK-II | apoA-II | 52-62 | 23 |
| 1201.6352 | -4.73 | LTISEQNIQR | apoB-100 | 335-344 | 24 |
| 1202.645 | -2.364 | VKSPELQAEAK-III | apoA-II | 52-62 | 23 |

TABLE 3-continued

PEPTIDES IDENTIFIED AS INFORMATIVE FOR CAD

| m/z | Magnitude in Regression Vector | Peptide | Protein | start-stop | SEQ ID NO |
|---|---|---|---|---|---|
| 1202.645 | −2.364 | LTISEQNIQR-I | apoB-100 | 335-344 | 24 |
| 1226.547 | 31.827 | DEPPQSPWDR | apoA-I | 25-34 | 25 |
| 1227.5777 | 22.165 | DEPPQSPWDR-I | apoA-I | 25-34 | 25 |
| 1283.6171 | 17.33 | WQEEMELYR | apoA-I | 132-140 | 26 |
| 1284.6444 | 13.139 | WQEEMELYR-I | apoA-I | 132-140 | 26 |
| 1285.6211 | 4.945 | WQEEMELYR-II | apoA-I | 132-140 | 26 |
| 1286.5985 | −1.058 | WQEEMELYR-III | apoA-I | 132-140 | 26 |
| 1299.5808 | 4.112 | WQEEMoxELYR | apoA-I | 132-140 | 26 |
| 1300.5688 | 4.532 | WQEEMoxELYR-I | apoA-I | 132-140 | 26 |
| 1301.6617 | −16.664 | THLAPYSDELR | apoA-I | 185-195 | 27 |
| 1302.6514 | −82.138 | THLAPYSDELR-I | apoA-I | 185-195 | 27 |
| 1302.6514 | −82.138 | LSPLGEEMRDR | apoA-I | 165-175 | 28 |
| 1303.6417 | −50.00 | THLAPYSDELR-II | apoA-I | 185-195 | 27 |
| 1303.6417 | −50.00 | LSPLGEEMRDR-I | apoA-I | 165-175 | 28 |
| 1304.685 | −25.542 | KGNVATEISTER | apoB-100 | 196-207 | 29 |
| 1305.6769 | −7.513 | KGNVATEISTER-I | apoB-100 | 196-207 | 29 |
| 1306.6696 | −0.949 | KGNVATEISTER-II | apoB-100 | 196-207 | 29 |
| 1318.6407 | 2.632 | LSPLGEEMoxRDR | apoA-I | 165-175 | 28 |
| 1319.6432 | 1.355 | LSPLGEEMoxRDR-I | apoA-I | 165-175 | 28 |
| 1380.7137 | −20.692 | VQPYLDDFQKK | apoA-I | 121-131 | 30 |
| 1381.7081 | −15.84 | VQPYLDDFQKK | apoA-I | 121-131 | 30 |
| 1400.6834 | 6.728 | DYVSQFEGSALGK | apoA-I | 52-64 | 31 |
| 1401.6922 | 4.3536 | DYVSQFEGSALGK-I | apoA-I | 52-64 | 31 |
| 1402.7018 | −2.083 | DYVSQFEGSALGK-II | apoA-I | 52-64 | 31 |
| 1403.7121 | −4.059 | DYVSQFEGSALGK-III | apoA-I | 52-64 | 31 |
| 1404.7231 | −2.216 | DYVSQFEGSALGK-IIII | apoA-I | 52-64 | 31 |
| 1410.748 | −6.002 | FQFPGKPGIYTR | apoB-100 | 4202-4213 | 32 |
| 1411.7077 | −12.606 | KWQEEMELYR | apoA-I | 131-140 | 33 |
| 1412.7244 | −1.039 | KWQEEMELYR-I | apoA-I | 131-140 | 33 |
| 1412.7244 | −1.039 | DPDRFRPDGLPK | SAA4 | 117-128 | 34 |
| 1413.6854 | −1.114 | KWQEEMELYR-II | apoA-I | 131-14- | 33 |
| 1413.6854 | −1.114 | DPDRFRPDGLPK-I | SAA4 | 117-128 | 34 |
| 1414.7036 | 0.290 | KWQEEMELYR-III | apoA-I | 131-140 | 33 |
| 1414.7036 | 0.290 | DPDRFRPDGLPK-II | SAA4 | 117-128 | 34 |
| 1415.7225 | 0.7011 | KWQEEMELYR-IV | apoA-I | 131-140 | 33 |
| 1415.7225 | 0.70 | DPDRFRPDGLPK-III | SAA4 | 117-128 | 34 |
| 1427.6644 | 11.458 | KWQEEMoxELYR | apoA-I | 131-140 | 33 |
| 1428.6927 | 9.069 | KWQEEMoxELYR-I | apoA-I | 131-140 | 33 |
| 1429.6645 | 5.938 | KWQEEMoxELYR-II | apoA-I | 131-140 | 33 |
| 1440.6864 | 48.538 | NPDAVAAPYCYTR | Lp(a) | 79-91 | 35 |
| 1441.6664 | 35.366 | NPDAVAAPYCYTR-I | Lp(a) | 79-91 | 35 |
| 1442.7047 | 16.693 | NPDAVAAPYCYTR-II | Lp(a) | 79-91 | 35 |
| 1488.7235 | −10.607 | MREWFSETFQK | apoC-I | 64-74 | 36 |
| 1489.7361 | −8.862 | MREWFSETFQK-I | apoC-I | 64-74 | 36 |
| 1490.6898 | −3.125 | MREWFSETFQK-II | apoC-I | 64-74 | 36 |
| 1504.7079 | −12.493 | MoxREWFSETFQK | apoC-I | 64-74 | 36 |
| 1505.7314 | −12.066 | MoxREWFSETFQK-I | apoC-I | 64-74 | 36 |
| 1506.6954 | −5.215 | MoxREWFSETFQK-II | apoC-I | 64-74 | 36 |
| 1568.8737 | 9.352 | LAARLEALKENGGAR | apoA-I | 198-212 | 37 |
| 1569.8781 | 6.904 | LAARLEALKENGGAR-I | apoA-I | 198-212 | 37 |
| 1585.8456 | 4.483 | THLAPYSDELRQR | apoA-I | 185-197 | 38 |
| 1586.8608 | 0.9348 | THLAPYSDELRQR-I | apoA-I | 185-197 | 38 |
| 1612.7768 | −17.535 | LLDNWDSVTSTFSK | apoA-I | 70-83 | 39 |
| 1716.8928 | 6.669 | DALSSVQESQVAQQAR | apoC-III | 45-60 | 40 |
| 1717.8545 | 3.025 | DALSSVQESQVAQQAR-I | apoC-III | 45-60 | 40 |
| 1718.8855 | −0.99 | DALSSVQESQVAQQAR-II | apoC-III | 45-60 | 40 |
| 1723.9809 | 2.583 | QKVEPLRAELQEGAR | apoA-I | 141-155 | 41 |
| 1723.9809 | 2.583 | IVQILPWEQNEQVK | apoB-100 | 577-590 | 42 |
| 1724.9466 | 1.7167 | QKVEPLRAELQEGAR-I | apoA-I | 141-155 | 41 |
| 1724.9466 | 1.7167 | IVQILPWEQNEQVK-I | apoB-100 | 577-590 | 42 |
| 1725.9818 | 1.707 | QKVEPLRAELQEGAR-II | apoA-I | 141-155 | 41 |
| 1725.9818 | 1.707 | IVQILPWEQNEQVK-II | apoB-100 | 577-590 | 42 |
| 1775.9145 | 15.536 | NLQNNAEWVYQGAIR | apoB-100 | 4107-4121 | 43 |
| 1776.9092 | 12.946 | NLQNNAEWVYQGAIR-I | apoB-100 | 4107-4121 | 43 |
| 1777.9046 | 11.265 | NLQNNAEWVYQGAIR-II | apoB-100 | 4107-4121 | 43 |
| 1904.9087 | 34.681 | TPEYYPNAGLIMNYCR | Lp(a) | 177-192 | 44 |
| 1905.8995 | 35.544 | TPEYYPNAGLIMNYCR-I | Lp(a) | 177-192 | 44 |
| 1906.8908 | 24.997 | SEAEDASLLSFMQGYMK | apoC-III | 21-37 | 45 |
| 1906.8908 | 24.997 | TPEYYPNAGLIMNYCR-II | Lp(a) | 177-192 | 44 |
| 1907.8826 | 12.840 | SEAEDASLLSFMQGYMK-I | apoC-III | 21-37 | 45 |
| 1907.8826 | 12.840 | TPEYYPNAGLIMNYCR-III | Lp(a) | 177-192 | 44 |
| 1922.8989 | 7.340 | SEAEDASLLSFMoxQGYMK | apoC-III | 21-37 | 45 |
| 2202.1435 | 41.389 | LREQLGPVTQEFWDNLEK | apoA-I | 84-101 | 46 |
| 2203.2007 | 49.396 | LREQLGPVTQEFWDNLEK-I | apoA-I | 84-101 | 46 |

TABLE 3-continued

PEPTIDES IDENTIFIED AS INFORMATIVE FOR CAD

| m/z | Magnitude in Regression Vector | Peptide | Protein | start-stop | SEQ ID NO |
|---|---|---|---|---|---|
| 2204.1703 | 35.316 | LREQLGPVTQEFWDNLEK-II | apoA-I | 84-101 | 46 |
| 2205.1404 | 16.202 | LREQLGPVTQEFWDNLEK-III | apoA-I | 84-101 | 46 |
| 2206.1991 | 6.574 | LREQLGPVTQEFWDNLEK-IIII | apoA-I | 84-101 | 46 |
| 2645.4139 | -7.042 | VQPYLDDFQKKWQEEMELYR | apoA-I | 121-140 | 47 |
| 2646.3664 | -12.328 | VQPYLDDFQKKWQEEMELYR-I | apoA-I | 121-140 | 47 |
| 2647.4251 | -9.890 | VQPYLDDFQKKWQEEMELYR-II | apoA-I | 121-140 | 47 |
| 2648.3783 | -5.448 | VQPYLDDFQKKWQEEMELYR-III | apoA-I | 121-140 | 47 |
| 2661.3337 | 8.767 | VQPYLDDFQKKWQEEMoxELYR | apoA-I | 121-140 | 47 |
| 2662.3985 | 12.259 | VQPYLDDFQKKWQEEMoxELYR-I | apoA-I | 121-140 | 47 |
| 2663.3571 | 9.880 | VQPYLDDFQKKWQEEMoxELYR-II | apoA-I | 121-140 | 47 |
| 2664.4226 | 5.8323 | VQPYLDDFQKKWQEEMoxELYR-III | apoA-I | 121-140 | 47 |

The m/z values are peaks that were obtained for the markers using mass spectrometry system using the methods described herein.

As shown in TABLE 3, a marker may be represented at multiple m/z points in a spectrum. This can be due to the fact that multiple isotopes (represented in TABLE 3 as "I, II, III, IIII") were observed, and/or that multiple charge states of the marker were observed, or that multiple isoforms of the marker were observed, for example, a post-translational modification such as oxidation. These multiple representations of a particular marker can be analyzed individually or grouped together. An example of how multiple representations of a marker may be grouped is that the intensities for the multiple peaks can be summed.

As shown below in TABLE 4 and TABLE 5, targeted tandem MS analysis identified the peptides corresponding to ten of the 13 informative features shown in FIG. 4 (i.e., most significant features that contributed to the PLS-DA model).

TABLE 4

INFORMATIVE FEATURES REPRESENTING INCREASED PROTEIN/PEPTIDE LEVELS IN CAD SUBJECTS AS COMPARED TO NORMAL SUBJECTS

| Channel m/z | Magnitude in Regression Vector | Protein corresponding to identified peptides | Protein Residues | Peptide Sequence | SEQ ID NO |
|---|---|---|---|---|---|
| 1081.6043 | +22.482 | apo-B100 | 559-567 | LAAYLMLMR | 15 |
| 1226.547 | +31.83 | apo-AI | 25-34 | DEPPQSPWDR | 25 |
| 1227.5777 | +22.165 | apo-AI | 25-34 | DEPPQSPWDR-I | 25 |
| 1440.6864 | +48.538 | Lp(a) | 79-91 | NPDAVAAPYCYTR | 35 |
| 1441.6664 | +35.366 | Lp(a) | 79-91 | NPDAVAAPYCYTR-I | 35 |
| 1442.7047 | +16.693 | Lp(a) | 79-91 | NPDAVAAPYCYTR-II | 35 |
| 1904.9087 | +34.681 | Lp(a) | 177-192 | TPEYYPNAGLIMNYCR | 44 |
| 1905.8995 | +35.544 | Lp(a) | 177-192 | TPEYYPNAGLIMNYCR-I | 44 |
| 1906.8908 | +24.997 | Lp(a) | 177-192 | TPEYYPNAGLIMNYCR-II | 44 |
| 1907.8826 | +12.840 | Lp(a) | 177-192 | TPEYYPNAGLIMNYCR-III | 44 |
| 1906.8908 | +24.997 | apoC-III | 21-37 | SEAEDASLLSFMQGYMK | 45 |
| 1907.8826 | +12.840 | apoC-III | 21-37 | SEAEDASLLSFMQGYMK-I | 45 |
| 1922.8989 | +7.340 | apoC-III | 21-37 | SEAEDASLLSFMoxQGYMK | 45 |
| 2202.1435 | +41.39 | apoA-I | 84-101 | LREQLGPVTQEFWDNLEK | 46 |
| 2203.2007 | +49.39 | apoA-I | 84-101 | LREQLGPVTQEFWDNLEK-I | 46 |
| 2204.1703 | +35.32 | apoA-I | 84-101 | LREQLGPVTQEFWDNLEK-II | 46 |
| 2205.1404 | +16.202 | apoA-I | 84-101 | LREQLGPVTQEFWDNLEK-III | 46 |
| 2206.1991 | +6.574 | apoA-I | 84-101 | LREQLGPVTQEFWDNLEK-IIII | 46 |
| 2661.3337 | +8.767 | apoA-I (Met112ox) | 121-140 | VQPYLDDFQKKWQEEM(Ox)ELYR | 47 |
| 2662.3985 | +12.259 | apoA-I (Met 112ox) | 121-140 | VQPYLDDFQKKWQEEM(Ox)ELYR-I | 47 |
| 2663.3571 | +9.880 | apoA-I (Met112ox) | 121-140 | VQPYLDDFQKKWQEEM(Ox)ELYR-II | 47 |
| 2664.4226 | +5.8323 | apoA-I (met112ox) | 121-140 | VQPYLDDFQKKWQEEM(Ox)ELYR-III | 47 |

Figure 5A:
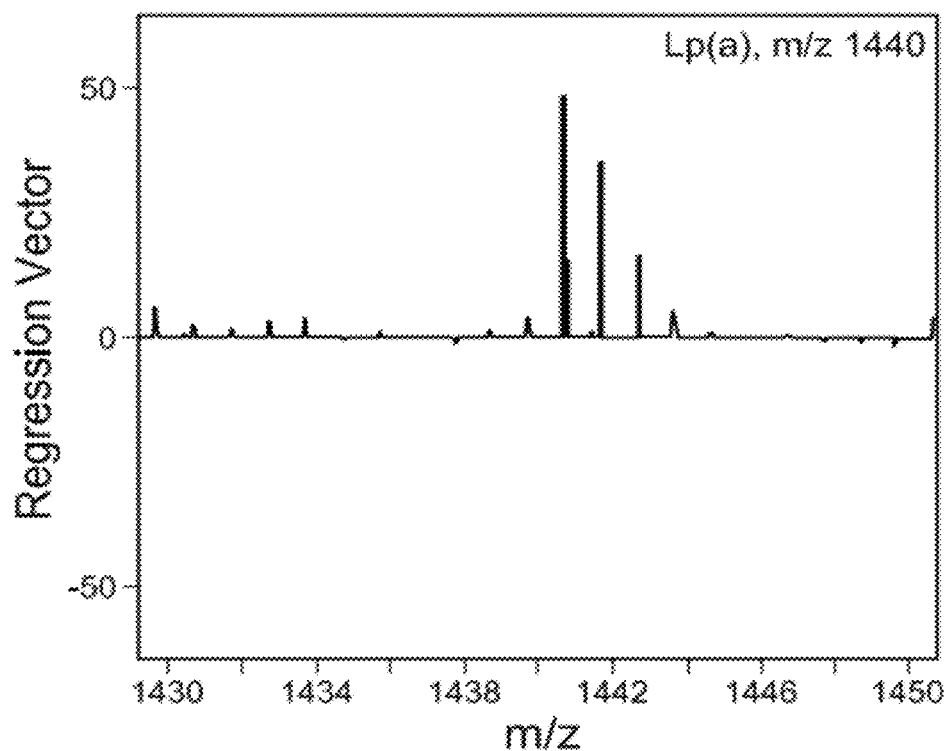
FIG. 5A graphically illustrates the strong positive feature in the PLS-DA regression vector at m/z 1440.68 identified by LC-MALDI-TOF/TOF MS/MS as corresponding to peptides derived from Lp(a), as described in Example 3.
Figure 5B:
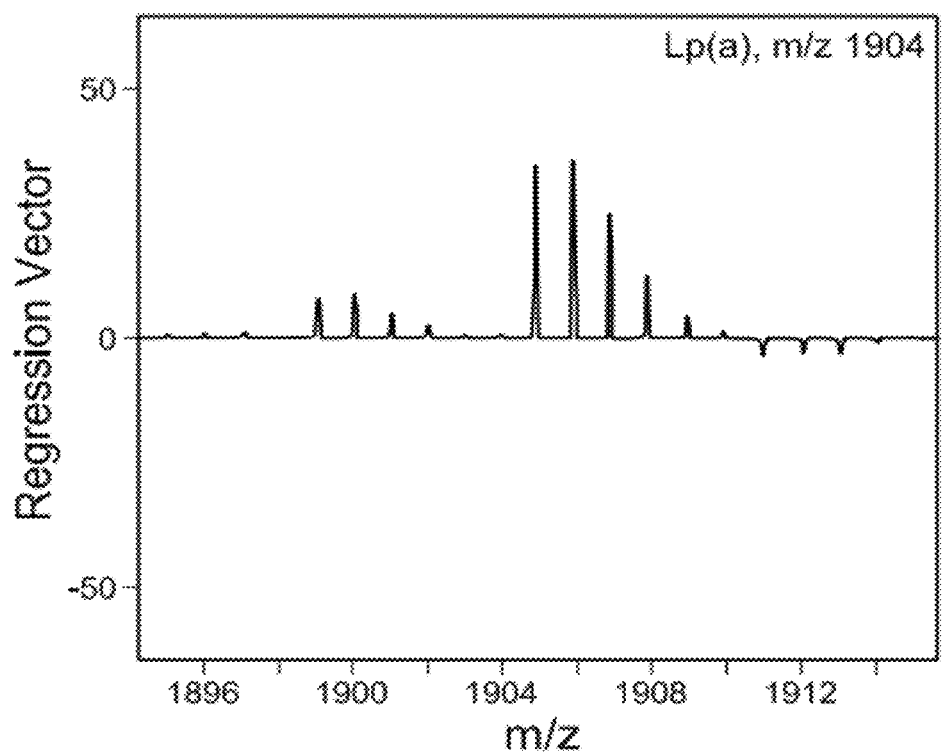
FIG. 5B graphically illustrates the strong positive feature in the PLS-DA regression vector at m/z 1904.91 identified by LC-MALDI-TOF/TOF MS/MS as corresponding to peptides derived from Lp(a), as described in Example 3.
Figure 5C:
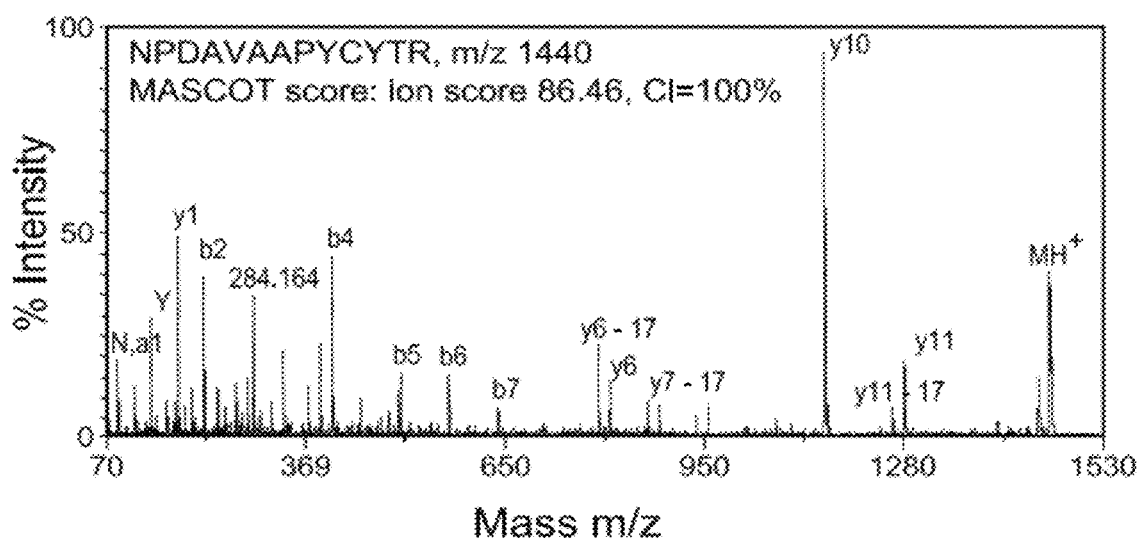
FIG. 5C illustrates the results of the MASCOT database search of the MS/MS spectrum of the peptide of m/z 1440.68 that identified Lp(a) with a high confidence level (CI100%), as described in Example 3.

As shown above in TABLE 4, identification of the tryptic peptides associated with the positive regression vector values shown in FIG. 4 revealed that, surprisingly, two peptides identified at m/z 1440 to 1442 (SEQ ID NO: 35) and m/z 1904 to 1906 (SEQ ID 44) derived from apolipoprotein(a) (Lp(a)) were increased in $HDL_2$ of CAD subjects, as compared to normal subjects. FIG. 5A graphically illustrates the strong positive informative feature in the PLS-DA regression vector at m/z 1440. As shown in FIG. 5C, the positive informative feature at m/z 1440 was identified by LC-MALDI-TOF/TOF MS/MS as corresponding to the peptide NPDAVAAPY-CYTR (SEQ ID NO:35) which corresponds to amino acids 79-91 of Lp(a) (SEQ ID NO:4), with a MASCOT ion score of 86.46 (CI=100%). As shown in FIG. 5B, another strong positive informative feature in the PLS-DA regression vector at m/z 1904 was identified as corresponding to the peptide TPEYYPNAGLIMNYCR (SEQ ID NO:44), which corresponds to amino acids 177-192 of Lp(a) (SEQ ID NO:4).

As further shown in TABLE 4, tryptic peptides identified at m/z 1906-1922 (SEQ ID NO: 45) derived from apoC-III (SEQ ID NO:6) were increased in $HDL_2$ of CAD subjects, as compared to normal subjects.

Taken together, these results demonstrate that pattern recognition profiling performed on $HDL_2$ isolated from CAD and control subjects show altered patterns of apoproteins present in the $HDL_2$ fractions which fall into two classes: (1) increased levels of peptides/proteins in CAD subjects as compared to normal controls; or (2) decreased levels of peptides/proteins in CAD subjects as compared to normal controls.

The observation that levels of Lp(a) were found to be increased in CAD subjects in comparison to normal controls was a surprising result because Lp(a) has been shown to be associated with small dense low density lipoproteins (LDLs), and its association with HDLs in general, and $HDL_2$ in particular, has not been previously shown. Thus, these results demonstrate that co-isolation of Lp(a) with $HDL_2$ subfraction permits pattern recognition analysis of the $HDL_2$ subfraction in the prediction, diagnosis, and prognosis of CAD subjects.

It was also observed that levels of apoC-III peptides were found to be elevated in CAD subjects, whereas those of apoC-I were decreased. In this regard, although not wishing to be bound by theory, it is noted that apoC-III inhibits lipoprotein lipase and the hepatic uptake of triglyceride-rich lipoproteins, which might promote an increase in atherogenic

TABLE 5

INFORMATIVE FEATURES REPRESENTING DECREASED PROTEIN/PEPTIDE LEVELS IN CAD SUBJECTS AS COMPARED TO NORMAL SUBJECTS

| Channel m/z | Magnitude in Regression Vector | Protein corresponding to Identified Peptides | Protein Residues | Peptide sequence | SEQ ID NO: |
|---|---|---|---|---|---|
| 1012.6055 | -39.93 | apoA-I | 231-239 | AKPALEDLR | 11 |
| 1013.5781 | -21.082 | apoA-I | 231-239 | AKPALEDLR-I | 11 |
| 1014.5921 | -5.15 | apoA-I | 231-239 | AKPALEDLR-II | 11 |
| 1157.6638 | -22.261 | apoA-I | 202-212 | LEALKENGGAR | 19 |
| 1158.6367 | -15.025 | apoA-I | 202-212 | LEALKENGGAR-I | 19 |
| 1159.6567 | -5.85 | apoA-I | 202-212 | LEALKENGGAR-II | 19 |
| 1160.6312 | -0.846 | apoA-I | 202-212 | LEALKENGGAR-III | 19 |
| 1301.6617 | -16.664 | apoA-I | 185-195 | THLAPYSDELR | 27 |
| 1302.6514 | -82.138 | apoA-I | 185-195 | THLAPYSDELR-I | 27 |
| 1303.6417 | -50.00 | apoA-I | 185-195 | THLAPYSDELR-II | 27 |
| 1302.6514 | -82.138 | apoA-I | 165-175 | LSPLGEEMRDR | 28 |
| 1303.6417 | -50.00 | apoA-I | 165-175 | LSPLGEEMRDR-I | 28 |
| 1380.7137 | -20.69 | apoA-I | 121-131 | VQPYLDDFQKK | 30 |
| 1381.7081 | -15.84 | apoA-I | 121-131 | VQPYLDDFQKK-I | 30 |
| 1488.7235 | -10.607 | apoC-I | 64-74 | MREWFSETFQK | 36 |
| 1489.7361 | -8.862 | apoC-I | 64-74 | MREWFSETFQK-I | 36 |
| 1490.6898 | -3.125 | apoC-I | 64-74 | MREWFSETFQK-II | 36 |
| 1504.7079 | -12.493 | apoC-I | 64-74 | MoxREWFSETFQK | 36 |
| 1505.7314 | -12.066 | apoC-I | 64-74 | MoxREWFSETFQK-I | 36 |
| 1506.6954 | -5.215 | apoC-I | 64-74 | MoxREWFSETFQK-II | 36 |
| 1612.7768 | -17.53 | apoA-I | 70-83 | LLDNWDSVTSTFSK | 39 |
| 2645.4139 | -7.042 | apoA-I | 121-140 | VQPYLDDFQKKWQEEMELYR | 47 |
| 2646.3664 | -12.328 | apoA-I | 121-140 | VQPYLDDFQKKWQEEMELYR-I | 47 |
| 2647.4251 | -9.89 | apoA-I | 121-140 | VQPYLDDFQKKWQEEMELYR-II | 47 |
| 2648.3783 | -5.448 | apoA-I | 121-140 | VQPYLDDFQKKWQEEMELYR-III | 47 |

As shown above in TABLE 5, identification of the tryptic peptides associated with the negative regression vector values shown in FIG. 4 revealed several peptides from apoA-I and a peptide from apoC-I were decreased in $HDL_2$ of CAD subjects compared to that of control subjects. The peptides derived from apoA-I (SEQ ID NO:1) that were identified as decreased in CAD subjects included SEQ ID NO:11, SEQ ID NO:19, SEQ ID NO:27, SEQ ID NO:28, SEQ ID NO:30, SEQ ID NO:39 and SEQ ID NO:47, as shown in TABLE 5.

The negative regression vector at m/z 1504-1506 was identified as corresponding to the peptide MREWFSETFQK (SEQ ID NO: 36) which corresponds to amino acids 64-74 of ApoC-I (SEQ ID NO: 5).

triglyceride-rich lipoproteins (see Ooi, E. M., et al., Clin Sci (Lond) 114:611-624, 2008. It is further noted that ApoC-I inhibits cholesterol ester transfer protein (CETP) (see Shachter, N. S., et al., Curr Opin Lipidol 12:297-304 (2001); Sparks, D. L., et al., J. Lipid Res 30:1491-1498, 1989. Thus, it is believed that alterations in apoC-I and apoC-III levels are likely contribute to lipid remodeling and the formation of pro-atherogenic HDL particles.

Therefore it is demonstrated that simultaneous profiling of these biomarkers in subjects using pattern recognition analysis may be used to aid in the diagnosis and prognosis of cardiovascular diseases in mammalian subjects.

Example 4

This example demonstrates that subjects may be successfully classified as CAD or control subjects based on the oxidation status of their $HDL_2$ using PLS-DA based pattern recognition proteomic profiling.

Methods:

Sample preparation and analysis: $HDL_2$ fractions were isolated from subjects, and samples from each individual subject were subjected to MALDI-TOF/TOF MS and PLS-DA analyses, as described in Example 2. Subjects were classified as either CAD or normal control subjects by pattern recognition proteomic profiling of $HDL_2$ proteins using PLS-DA. The PLS-DA models were characterized by regression vectors as described in Example 3. The PLS-DA model regression vector analysis is centered on post-translationally modified peptides derived from apoA-I, the major protein in $HDL_2$.

Results:

In addition to the first two groups of informative features (increased or decreased peptide levels in CAD subjects as compared to normal subjects) as described in Example 2, a third group of informative features in the PLS-DA model was identified that centered on post-translationally modified peptides derived from apoA-I (SEQ ID NO:1), the major protein in HDL. MS/MS analysis confirmed the presence of these peptide sequences in the $HDL_2$ fraction and demonstrated that the methionine 112 residue had been converted to methionine sulfoxide (Met(O)).

Figure 6A:
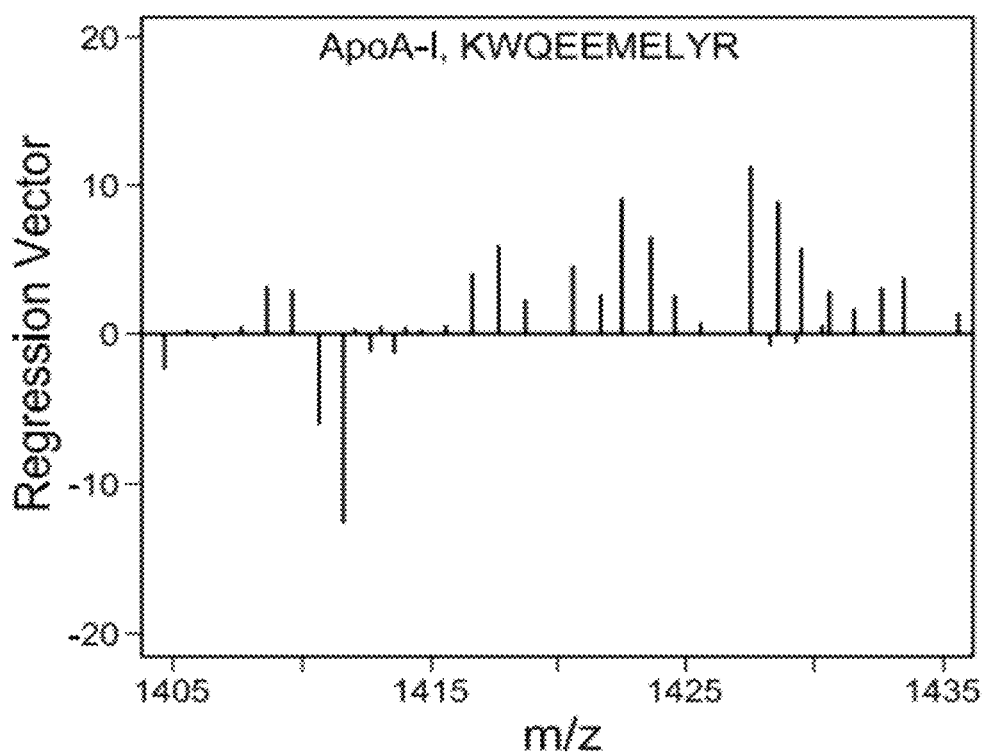

As shown in FIGS. 6A-D and summarized below in TABLE 6, this third group of informative features included both native peptides KWQEEMELYR (SEQ ID NO:33) and VQPYLDDFQKKWQEEMELYR (SEQ ID NO: 47) and the corresponding oxidized peptides that contained methionine 112 (Met112). FIG. 6A graphically illustrates the negative regression vector at m/z 1411.7077 and the positive regression vector at m/z 1427.6644 which were identified as corresponding to the native form of the apoA-I peptide KWQEEMELYR (SEQ ID NO: 33), and the Met112 oxidized form KWQEEM(O)ELYR of SEQ ID NO:33, respectively, as shown in FIG. 6C (MASCOT ion score of 84.8, CI=100%).

Figure 6B:
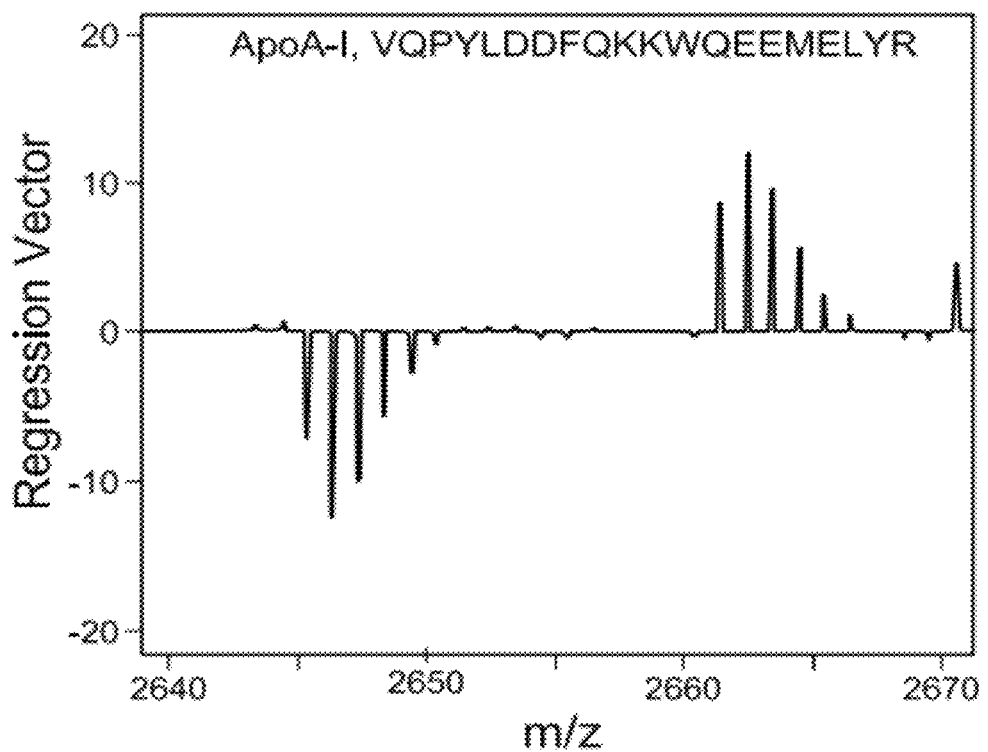

FIG. 6B graphically illustrates the negative regression vector at m/z 2646.3664 and the positive regression vector at m/z 2662.3985 which were identified as corresponding to the native form of the apoA-I peptide VQPYLDDFQKKWQEEMELYR (SEQ ID NO:47), and the Met112 oxidized form VQPYLDDFQKKWQEEM(O)ELYR of SEQ ID NO:47, respectively, as shown in FIG. 6D (MASCOT ion score of 42.6, CI=99.96%).

Strikingly, as shown in FIG. 6 and summarized above in TABLE 6, the signals for the Met 112 oxidized (Met112(O)) apoA-I peptides (SEQ ID NO:33 and SEQ ID NO:47) were found to be increased in CAD subjects as compared to normal control subjects, while the levels of the corresponding native Met112 peptides (SEQ ID NO:33 and SEQ ID NO:47) were found to be decreased in CAD subjects as compared to normal control subjects.

It is noted however, that no difference in relative levels of other methionine containing native and oxidized peptides, such as those derived from apoC-I, were observed between normal controls and CAD subjects was observed in this analysis (data not shown), suggesting that the difference in levels of oxygenated Met112 did not result from ex vivo oxidation.

While not wishing to be bound by theory, oxidation has been proposed as one mechanism for generating dysfunctional HDL resulting in decreased reverse cholesterol transport, thereby disrupting normal cholesterol homeostasis. Lipid hydroperoxides and reactive intermediates produced by Myeloperoxidase (MPO) oxidize apoA-I. It has been shown that oxidation of methionine residues impairs apoA-I's ability to promote cholesterol efflux by the ABCA1 pathway (Shao, B., et al., *J Biol Chem* 281(14):9001-9004 (2006) and to activate LCAT, two key steps in removing cholesterol from lipid-laden macrophages. apoA-I co-localizes with HOCl oxidation adducts in human atherosclerotic tissues. MPO-produced HOCl is known to modify HDL in vivo. Antibodies specific for apoA-I and HOCl-modified proteins immunostained coronary arteries obtained from patients undergoing cardiac transplantation (O'Brien et al., *Circulation* 98:519-527, 1998). apoA-I co-localized with epitopes recognized by HOP-I antibody, which is specific for proteins oxidized by HOCl (Hazell et al., *J. Clin. Invest.* 97:1535-1544, 1996) in the intima of atherosclerotic lesions. The co-localization of HOCl-modified proteins with apoA-I suggests that HOCl oxidizes specific proteins in the human artery wall.

Oxidized HDLs are also present in the circulation of CVD patients, (International Publication No. WO2006/014628). Circulating HDL from cardiovascular patients has 8-times higher 3-chlorotyrosine than normal subjects. Levels of chlorinated HDL are elevated in the blood of humans suffering from clinically significant atherosclerosis. In addition, MPO-produced $H_2O_2$ is also capable of oxidizing methionines of apoA-I associated with $HDL_3$ (International Publication No. WO2006/014628). These $HDL_3$ subfractions are selectively enriched with oxidized amino acids.

Collectively, these observations support the conclusion that $HDL_2$ from control and CAD subjects differ in their protein cargoes and levels of oxidized methionine residues.

TABLE 6

INFORMATIVE FEATURES REPRESENTING POSTTRANSLATIONALLY MODIFIED PEPTIDES IN CAD SUBJECTS AS COMPARED TO NORMAL SUBJECTS

| Channel m/z | Magnitude in Regression Vector | Protein/ peptide location | Modification | Peptide Sequence | SEQ ID |
|---|---|---|---|---|---|
| 1411.7077 | -12.606 | apoA-I (131-140) | native | KWQEEMELYR | 33 |
| 1427.6644 | +11.458 | apoA-I (131-140) | oxidized M112 (MetOx) | KWQEEM(O)ELYR | 33 |
| 2646.3664 | -12.328 | apoA-I (121-140) | native | VQPYLDDFQKKWQEEMELYR-I | 47 |
| 2662.3985 | +12.259 | apoA-I (121-140) | oxidized M112 (MetOx) | VQPYLDDFQKKWQEEM(O)ELYR-I | 47 |

Because pattern recognition analysis makes no assumptions about the origins of the differential signals seen in the regression vectors for each sample, it provides a powerful tool for identifying post-translationally modified peptides that would be very difficult to identify using classic proteomic approaches. The results demonstrated in this example indicate that oxidized methionines (Met(O)) in apoA-I are detectable by pattern recognition profiling of an $HDL_2$ subfraction. Since oxidation of methionine residues impairs apoA-I's ability to promote cholesterol efflux by the ABCA1 pathway (Shao, B., et al., "Myeloperoxidase impairs ABCA1-dependent cholesterol efflux through methionine oxidation and site-specific tyrosine chlorination of apolipoprotein A-I," *J. Biol. Chem.* 281:9001-4, 2006) and to activate Lecithin:Cholesterol Acyltransferase (LCAT) (Shao, B., et al., "Methionine oxidation impairs reverse cholesterol transport by apolipoprotein A-I," *Proc. Natl. Acad. Sci.* 2008, In press), oxidized apoA-I likely acts as a mediator of CAD, and serves as a useful biomarker for CAD. Thus, a subject may be evaluated for the presence of oxidized apoA-I (SEQ ID NO:1) to determine the risk, diagnosis, prognosis of CAD in the subject and/or to measure the efficacy of treatment of a subject suffering from CAD.

Example 5

This example demonstrates that the conformational structure of apoA-I in $HDL_2$ subfractions is altered in CAD subjects as compared to the conformation structure of apoA-I in $HDL_2$ subfractions of normal control subjects.

Rationale:

The structural conformation of apoA-I has been suggested to influence its ability to transfer cholesterol ester from $HDL_2$ particles to scavenger receptor BI as part of reverse cholesterol transport and cholesterol ester clearance in the liver (de Beer, M. C., et al., *J. of Lipid Res* 42:309-313, February 2001). Contact between the N-terminal fold and the C-terminal domain of apoA-I has been suggested to stabilize the lipid-bound conformation of the protein. Since methionines in apoA-I are oxidized in CAD subjects, as demonstrated in Example 4, an experiment was carried out to determine if such post-translational modifications lead to local changes in the structural conformation of apoA-I. Alterations in a protein's local structure is said to affect susceptibility of the protein to proteolytic digestion, which in turn can affect the apparent abundance of peptides assessed by MS.

Methods:

Sample preparation and analysis: $HDL_2$ fractions were isolated from subjects and treated with trypsin as disclosed in Example 1. The samples from each individual subject were subjected to MALDI-TOF/TOF MS, as described in Example 2. Subjects were classified as either CAD or normal subjects by pattern recognition proteomic profiling of $HDL_2$ proteins using PLS-DA. The PLS-DA models were characterized by regression vectors as described in Example 3. The PLS-DA model regression vector analysis is centered on apoA-I peptides of $HDL_2$. The differential signals reflecting the relative abundance of the trypsinized peptides was measured.

Results:

In addition to the three groups of informative features (increased or decreased peptide levels in CAD subjects as compared to normal subjects) as described in Example 2, and post-translationally modified peptides derived from apoA-I as described in Example 3, a fourth group of informative features in the PLS-DA model was identified based on the altered structural conformation of apoA-I present in the $HDL_2$ subfraction of CAD subjects in comparison to the structural conformation of apoA-I present in the $HDL_2$ subjection of normal subjects.

Informative features corresponding to tryptic peptides derived from the N-terminal and C-terminal regions of apoA-I (SEQ ID NO:1) were identified. FIG. 7 graphically illustrates the regression vector values (y-axis) for the amino acid sequence of apoA-I (x-axis).

It was determined that two tryptic apoA-I peptides originating from N-terminal regions of the mature protein (residues 1-10: DEPPQSPWDR (SEQ ID NO:48) and residues 60-77, LREQLGPVTQEFWDNLEK (SEQ ID NO:49) were significantly increased in CAD subjects as compared to normal controls, while one C-terminal region peptide (residues 207-215, AKPALEDLR (SEQ ID NO:50) was significantly decreased as compared to normal controls, as shown in FIG. 7. Also, a tryptic peptide (peptide 46-59: LLDNWDSVT-STFSK (SEQ ID NO:52) was apparently decreased in abundance. These observations suggest that tryptic digests of apoA-I in HDL isolated from control and CAD subjects give different patterns of peptides, perhaps because of conformational differences of the apoA-I in the two different classes of subjects. Indeed, although the above-referenced N-terminal peptides (SEQ ID NO:48 and SEQ ID NO:49) and C-terminal peptides (SEQ ID NO:49) are distant in apoA-I sequence, when mapped to the double-belt model of the lipid-associated apoA-I (Davidson, W. S., et al., *J. Biol. Chem.* 282(31): 22249-22253 (2007)) or spherical HDL particle apoA-I model (Davidson W. S. PNAS 2008, in press), the peptides displaying significant changes in CAD subjects were found to be in close proximity (data not shown).

Additionally, it was determined that the peptides (residues 97-107, VQPYLDDFQKK SEQ ID NO: 51) proximal to Met112 was significantly decreased in the CAD samples (FIG. 7), as is the peptide containing Met112, SEQ ID NO:33.

It was recently proposed that contact between the globular N-terminal fold and the C-terminal fold of apoA-I stabilizes the lipid-bound conformation of the protein. It is important to note that alterations in a proteins' local structure can effect susceptibility to proteolytic digestion, which in turn can affect the apparent abundance of peptides in a MS analysis. As demonstrated in this example, the differential levels of N-terminal and C-terminal apoA-I peptides indicates that the secondary and/or tertiary conformations at the N and C-termini of apoA-I differ in the $HDL_2$ of CAD subjects as compared to normal control subjects. Further in this regard, as described in Example 4 and summarized in TABLE 6, it was also determined that levels of apoA-I peptides containing Met(O)112 were elevated in the $HDL_2$ of CAD subjects concomitantly with a decrease in Met112 peptides in the CAD subjects. The peptides directly adjacent to the peptides containing Met112 also displayed significant changes in CAD subjects as compared to normal controls. While not wishing to be bound by theory, these observations suggest that oxidation of methionine residues in apoA-I is increased in CAD subjects and such oxidation may lead to local changes in the conformation of the apoA-I protein which can be detected by tryptic digestion followed by analysis by mass spectrometry.

The results described in this example demonstrate that the altered conformation of apoA-I at its N- and C-termini is detectable using PLS-DA-based pattern recognition profiling. Changes in relative abundance of certain tryptic peptides demonstrate that apoA-I exists in altered secondary and/or tertiary conformation in $HDL_2$ subfractions of CAD subjects compared to control subjects. Thus, dysfunctionality of $HDL_2$ of CAD subjects likely results from changes in the proteome profile and conformation of the associated $HDL_2$ proteins. These results demonstrate that pattern recognition profiling using tryptic peptides of $HDL_2$ subfractions from subjects can be used to determine the conformation status of apoA-I in order to classify subjects as normal or CAD patients.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of screening a mammalian subject to determine if the subject is at risk to develop, or is suffering from, cardiovascular disease, the method comprising detecting a measurable feature of at least two biomarkers in an HDL subfraction, or in a complex containing apoA-I or apoA-II isolated from a biological sample obtained from the subject, wherein the at least two biomarkers are selected from the group consisting of apoA-I, apoA-II, apoB-100, Lp(a), apoC-I, and apoC-III, combinations or portions and/or derivatives thereof, and comparing the measurable features of the at least two biomarkers from the biological sample to a reference standard, wherein a difference in the measurable features of the at least two biomarkers from the biological sample and the reference standard is indicative of the presence or risk of cardiovascular disease in the subject.

2. The method of claim 1, wherein the HDL subfraction of the biological sample is the HDL2 subfraction.

3. The method of claim 1, wherein the biological sample is selected from the group consisting of a blood sample, a serum sample, a plasma sample, a tissue sample, a bodily fluid sample, and a urine sample.

4. The method of claim 1, wherein at least one of the measurable features indicative of the presence or risk of cardiovascular disease comprises an increased amount of at least one of the biomarkers in the HDL subfraction or in the complex containing apoA-I or apoA-II isolated from the biological sample selected from the group consisting of apoA-I, apoB-100, apoC-III and Lp(a), or portions and/or derivatives thereof, in comparison to the reference standard.

5. The method of claim 4, wherein the biomarker is apoA-I, or a portion or derivative thereof.

6. The method of claim 4, wherein the biomarker is apoC-III or a portion or derivative thereof.

7. The method of claim 4, wherein the biomarker is Lp(a) or a portion or derivative thereof.

8. The method of claim 1, wherein at least one of the measurable features indicative of the presence or risk of cardiovascular disease comprises a decreased amount of at least one of the biomarkers in the HDL subfraction or in the complex containing apoA-I or apoA-II isolated from the biological sample selected from the group consisting of apoA-I and apoC-I, or portions and/or derivatives thereof, in comparison to the reference standard.

9. The method of claim 8, wherein the biomarker is apoA-I, or a portion or derivative thereof.

10. The method of claim 8, wherein the biomarker is apoC-I, or a portion or derivative thereof.

11. The method of claim 1, wherein at least one of the measurable features indicative of the presence or risk of cardiovascular disease comprises a post-translational modification of a peptide derived from apoA-I in the HDL subfraction or complex isolated from the biological sample, in comparison to the reference standard.

12. The method of claim 11, wherein the post-translational modification of apoA-I is oxidation of at least one Methionine residue.

13. The method of claim 1, wherein at least one of the measurable features indicative of the presence or risk of cardiovascular disease comprises an altered structural conformation of apoA-I in the HDL subfraction of the biological sample, in comparison to a reference standard.

14. The method of claim 1, wherein the measurable features of the at least two biomarkers from the biological sample are determined using mass spectrometry analysis.

15. The method of claim 14, wherein the mass spectrometry analysis is performed on a tryptic digestion of the HDL subfraction or complex isolated from the biological sample.

16. The method of claim 14, wherein the mass spectrometry analysis is carried out with a matrix-assisted laser desorption ionization (MALDI) mass spectrometer or LCMS.

17. The method of claim 1, wherein the cardiovascular disease is the predisposition to myocardial infarction, atherosclerosis, coronary artery disease, peripheral artery disease, heart failure, or stroke.

18. The method of claim 1, wherein the measurable features of the at least two biomarkers in the HDL subfraction or complex isolated from the biological sample are detected using at least one antibody specific to each of the at least one of the two biomarkers.

* * * * *

SEQUENCE LISTING

<160> NUMBER OF SEQ ID NOS: 52

<210> SEQ ID NO 1
<211> LENGTH: 267
<212> TYPE: PRT
<213> ORGANISM: Homo sapiens

<400> SEQUENCE: 1

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 2
<211> LENGTH: 100
<212> TYPE: PRT
<213> ORGANISM: Homo sapiens

<400> SEQUENCE: 2

Met Lys Leu Leu Ala Ala Thr Val Leu Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
        35                  40                  45

```
Met Glu Lys Val Lys Ser Pro Glu Leu Gln Ala Glu Ala Lys Ser Tyr
    50              55                  60
Phe Glu Lys Ser Lys Glu Gln Leu Thr Pro Leu Ile Lys Lys Ala Gly
 65              70                  75                  80
Thr Glu Leu Val Asn Phe Leu Ser Tyr Phe Val Glu Leu Gly Thr Gln
                 85                  90                  95
Pro Ala Thr Gln
            100

<210> SEQ ID NO 3
<211> LENGTH: 4563
<212> TYPE: PRT
<213> ORGANISM: Homo sapiens

<400> SEQUENCE: 3

Met Asp Pro Pro Arg Pro Ala Leu Leu Ala Leu Leu Ala Leu Pro Ala
 1               5                  10                  15
Leu Leu Leu Leu Leu Ala Gly Ala Arg Ala Glu Glu Glu Met Leu
                 20                  25                  30
Glu Asn Val Ser Leu Val Cys Pro Lys Asp Ala Thr Arg Phe Lys His
                 35                  40                  45
Leu Arg Lys Tyr Thr Tyr Asn Tyr Glu Ala Glu Ser Ser Ser Gly Val
    50              55                  60
Pro Gly Thr Ala Asp Ser Arg Ser Ala Thr Arg Ile Asn Cys Lys Val
 65              70                  75                  80
Glu Leu Glu Val Pro Gln Leu Cys Ser Phe Ile Leu Lys Thr Ser Gln
                 85                  90                  95
Cys Thr Leu Lys Glu Val Tyr Gly Phe Asn Pro Glu Gly Lys Ala Leu
                100                 105                 110
Leu Lys Lys Thr Lys Asn Ser Glu Glu Phe Ala Ala Ala Met Ser Arg
                115                 120                 125
Tyr Glu Leu Lys Leu Ala Ile Pro Glu Gly Lys Gln Val Phe Leu Tyr
    130             135                 140
Pro Glu Lys Asp Glu Pro Thr Tyr Ile Leu Asn Ile Lys Arg Gly Ile
145                 150                 155                 160
Ile Ser Ala Leu Leu Val Pro Pro Glu Thr Glu Glu Ala Lys Gln Val
                165                 170                 175
Leu Phe Leu Asp Thr Val Tyr Gly Asn Cys Ser Thr His Phe Thr Val
                180                 185                 190
Lys Thr Arg Lys Gly Asn Val Ala Thr Glu Ile Ser Thr Glu Arg Asp
    195                 200                 205
Leu Gly Gln Cys Asp Arg Phe Lys Pro Ile Arg Thr Gly Ile Ser Pro
    210             215                 220
Leu Ala Leu Ile Lys Gly Met Thr Arg Pro Leu Ser Thr Leu Ile Ser
225                 230                 235                 240
Ser Ser Gln Ser Cys Gln Tyr Thr Leu Asp Ala Lys Arg Lys His Val
                245                 250                 255
Ala Glu Ala Ile Cys Lys Glu Gln His Leu Phe Leu Pro Phe Ser Tyr
                260                 265                 270
Lys Asn Lys Tyr Gly Met Val Ala Gln Val Thr Gln Thr Leu Lys Leu
                275                 280                 285
Glu Asp Thr Pro Lys Ile Asn Ser Arg Phe Phe Gly Glu Gly Thr Lys
    290                 295                 300
Lys Met Gly Leu Ala Phe Glu Ser Thr Lys Ser Thr Ser Pro Pro Lys
305                 310                 315                 320
```

-continued

```
Gln Ala Glu Ala Val Leu Lys Thr Leu Gln Glu Leu Lys Lys Leu Thr
                325                 330                 335

Ile Ser Glu Gln Asn Ile Gln Arg Ala Asn Leu Phe Asn Lys Leu Val
                340                 345                 350

Thr Glu Leu Arg Gly Leu Ser Asp Glu Ala Val Thr Ser Leu Leu Pro
                355                 360                 365

Gln Leu Ile Glu Val Ser Ser Pro Ile Thr Leu Gln Ala Leu Val Gln
            370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
                420                 425                 430

Ala Arg Asp Gln Arg Ser Arg Ala Thr Leu Tyr Ala Leu Ser His Ala
            435                 440                 445

Val Asn Asn Tyr His Lys Thr Asn Pro Thr Gly Thr Gln Glu Leu Leu
450                 455                 460

Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
                485                 490                 495

Gln Thr Met Glu Gln Leu Thr Pro Glu Leu Lys Ser Ser Ile Leu Lys
            500                 505                 510

Cys Val Gln Ser Thr Lys Pro Ser Leu Met Ile Gln Lys Ala Ala Ile
            515                 520                 525

Gln Ala Leu Arg Lys Met Glu Pro Lys Asp Lys Asp Gln Glu Val Leu
            530                 535                 540

Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                565                 570                 575

Ile Val Gln Ile Leu Pro Trp Glu Gln Asn Glu Gln Val Lys Asn Phe
            580                 585                 590

Val Ala Ser His Ile Ala Asn Ile Leu Asn Ser Glu Glu Leu Asp Ile
            595                 600                 605

Gln Asp Leu Lys Lys Leu Val Lys Glu Ala Leu Lys Glu Ser Gln Leu
            610                 615                 620

Pro Thr Val Met Asp Phe Arg Lys Phe Ser Arg Asn Tyr Gln Leu Tyr
625                 630                 635                 640

Lys Ser Val Ser Leu Pro Ser Leu Asp Pro Ala Ser Ala Lys Ile Glu
                645                 650                 655

Gly Asn Leu Ile Phe Asp Pro Asn Asn Tyr Leu Pro Lys Glu Ser Met
            660                 665                 670

Leu Lys Thr Thr Leu Thr Ala Phe Gly Phe Ala Ser Ala Asp Leu Ile
            675                 680                 685

Glu Ile Gly Leu Glu Gly Lys Gly Phe Glu Pro Thr Leu Glu Ala Leu
            690                 695                 700

Phe Gly Lys Gln Gly Phe Phe Pro Asp Ser Val Asn Lys Ala Leu Tyr
705                 710                 715                 720

Trp Val Asn Gly Gln Val Pro Asp Gly Val Ser Lys Val Leu Val Asp
                725                 730                 735

His Phe Gly Tyr Thr Lys Asp Asp Lys His Glu Gln Asp Met Val Asn
                740                 745                 750
```

```
Gly Ile Met Leu Ser Val Glu Lys Leu Ile Lys Asp Leu Lys Ser Lys
            755                 760                 765

Glu Val Pro Glu Ala Arg Ala Tyr Leu Arg Ile Leu Gly Glu Glu Leu
            770                 775                 780

Gly Phe Ala Ser Leu His Asp Leu Gln Leu Leu Gly Lys Leu Leu Leu
785                 790                 795                 800

Met Gly Ala Arg Thr Leu Gln Gly Ile Pro Gln Met Ile Gly Glu Val
                    805                 810                 815

Ile Arg Lys Gly Ser Lys Asn Asp Phe Phe Leu His Tyr Ile Phe Met
                820                 825                 830

Glu Asn Ala Phe Glu Leu Pro Thr Gly Ala Gly Leu Gln Leu Gln Ile
            835                 840                 845

Ser Ser Ser Gly Val Ile Ala Pro Gly Ala Lys Ala Gly Val Lys Leu
        850                 855                 860

Glu Val Ala Asn Met Gln Ala Glu Leu Val Ala Lys Pro Ser Val Ser
865                 870                 875                 880

Val Glu Phe Val Thr Asn Met Gly Ile Ile Pro Asp Phe Ala Arg
                    885                 890                 895

Ser Gly Val Gln Met Asn Thr Asn Phe Phe His Glu Ser Gly Leu Glu
                900                 905                 910

Ala His Val Ala Leu Lys Ala Gly Lys Leu Lys Phe Ile Ile Pro Ser
            915                 920                 925

Pro Lys Arg Pro Val Lys Leu Leu Ser Gly Gly Asn Thr Leu His Leu
        930                 935                 940

Val Ser Thr Thr Lys Thr Glu Val Ile Pro Pro Leu Ile Glu Asn Arg
945                 950                 955                 960

Gln Ser Trp Ser Val Cys Lys Gln Val Phe Pro Gly Leu Asn Tyr Cys
                    965                 970                 975

Thr Ser Gly Ala Tyr Ser Asn Ala Ser Ser Thr Asp Ser Ala Ser Tyr
                980                 985                 990

Tyr Pro Leu Thr Gly Asp Thr Arg Leu Glu Leu Glu Leu Arg Pro Thr
            995                 1000                1005

Gly Glu Ile Glu Gln Tyr Ser Val Ser Ala Thr Tyr Glu Leu Gln
        1010                1015                1020

Arg Glu Asp Arg Ala Leu Val Asp Thr Leu Lys Phe Val Thr Gln
        1025                1030                1035

Ala Glu Gly Ala Lys Gln Thr Glu Ala Thr Met Thr Phe Lys Tyr
        1040                1045                1050

Asn Arg Gln Ser Met Thr Leu Ser Ser Glu Val Gln Ile Pro Asp
        1055                1060                1065

Phe Asp Val Asp Leu Gly Thr Ile Leu Arg Val Asn Asp Glu Ser
        1070                1075                1080

Thr Glu Gly Lys Thr Ser Tyr Arg Leu Thr Leu Asp Ile Gln Asn
        1085                1090                1095

Lys Lys Ile Thr Glu Val Ala Leu Met Gly His Leu Ser Cys Asp
        1100                1105                1110

Thr Lys Glu Glu Arg Lys Ile Lys Gly Val Ile Ser Ile Pro Arg
        1115                1120                1125

Leu Gln Ala Glu Ala Arg Ser Glu Ile Leu Ala His Trp Ser Pro
        1130                1135                1140

Ala Lys Leu Leu Leu Gln Met Asp Ser Ser Ala Thr Ala Tyr Gly
        1145                1150                1155

Ser Thr Val Ser Lys Arg Val Ala Trp His Tyr Asp Glu Glu Lys
```

-continued

```
              1160                1165                1170

Ile  Glu  Phe  Glu  Trp  Asn  Thr  Gly  Thr  Asn  Val  Asp  Thr  Lys  Lys
1175                     1180                     1185

Met  Thr  Ser  Asn  Phe  Pro  Val  Asp  Leu  Ser  Asp  Tyr  Pro  Lys  Ser
1190                     1195                     1200

Leu  His  Met  Tyr  Ala  Asn  Arg  Leu  Leu  Asp  His  Arg  Val  Pro  Gln
1205                     1210                     1215

Thr  Asp  Met  Thr  Phe  Arg  His  Val  Gly  Ser  Lys  Leu  Ile  Val  Ala
1220                     1225                     1230

Met  Ser  Ser  Trp  Leu  Gln  Lys  Ala  Ser  Gly  Ser  Leu  Pro  Tyr  Thr
1235                     1240                     1245

Gln  Thr  Leu  Gln  Asp  His  Leu  Asn  Ser  Leu  Lys  Glu  Phe  Asn  Leu
1250                     1255                     1260

Gln  Asn  Met  Gly  Leu  Pro  Asp  Phe  His  Ile  Pro  Glu  Asn  Leu  Phe
1265                     1270                     1275

Leu  Lys  Ser  Asp  Gly  Arg  Val  Lys  Tyr  Thr  Leu  Asn  Lys  Asn  Ser
1280                     1285                     1290

Leu  Lys  Ile  Glu  Ile  Pro  Leu  Pro  Phe  Gly  Gly  Lys  Ser  Ser  Arg
1295                     1300                     1305

Asp  Leu  Lys  Met  Leu  Glu  Thr  Val  Arg  Thr  Pro  Ala  Leu  His  Phe
1310                     1315                     1320

Lys  Ser  Val  Gly  Phe  His  Leu  Pro  Ser  Arg  Glu  Phe  Gln  Val  Pro
1325                     1330                     1335

Thr  Phe  Thr  Ile  Pro  Lys  Leu  Tyr  Gln  Leu  Gln  Val  Pro  Leu  Leu
1340                     1345                     1350

Gly  Val  Leu  Asp  Leu  Ser  Thr  Asn  Val  Tyr  Ser  Asn  Leu  Tyr  Asn
1355                     1360                     1365

Trp  Ser  Ala  Ser  Tyr  Ser  Gly  Gly  Asn  Thr  Ser  Thr  Asp  His  Phe
1370                     1375                     1380

Ser  Leu  Arg  Ala  Arg  Tyr  His  Met  Lys  Ala  Asp  Ser  Val  Val  Asp
1385                     1390                     1395

Leu  Leu  Ser  Tyr  Asn  Val  Gln  Gly  Ser  Gly  Glu  Thr  Thr  Tyr  Asp
1400                     1405                     1410

His  Lys  Asn  Thr  Phe  Thr  Leu  Ser  Cys  Asp  Gly  Ser  Leu  Arg  His
1415                     1420                     1425

Lys  Phe  Leu  Asp  Ser  Asn  Ile  Lys  Phe  Ser  His  Val  Glu  Lys  Leu
1430                     1435                     1440

Gly  Asn  Asn  Pro  Val  Ser  Lys  Gly  Leu  Leu  Ile  Phe  Asp  Ala  Ser
1445                     1450                     1455

Ser  Ser  Trp  Gly  Pro  Gln  Met  Ser  Ala  Ser  Val  His  Leu  Asp  Ser
1460                     1465                     1470

Lys  Lys  Lys  Gln  His  Leu  Phe  Val  Lys  Glu  Val  Lys  Ile  Asp  Gly
1475                     1480                     1485

Gln  Phe  Arg  Val  Ser  Ser  Phe  Tyr  Ala  Lys  Gly  Thr  Tyr  Gly  Leu
1490                     1495                     1500

Ser  Cys  Gln  Arg  Asp  Pro  Asn  Thr  Gly  Arg  Leu  Asn  Gly  Glu  Ser
1505                     1510                     1515

Asn  Leu  Arg  Phe  Asn  Ser  Ser  Tyr  Leu  Gln  Gly  Thr  Asn  Gln  Ile
1520                     1525                     1530

Thr  Gly  Arg  Tyr  Glu  Asp  Gly  Thr  Leu  Ser  Leu  Thr  Ser  Thr  Ser
1535                     1540                     1545

Asp  Leu  Gln  Ser  Gly  Ile  Ile  Lys  Asn  Thr  Ala  Ser  Leu  Lys  Tyr
1550                     1555                     1560
```

-continued

```
Glu Asn Tyr Glu Leu Thr Leu Lys Ser Asp Thr Asn Gly Lys Tyr
1565                1570                1575

Lys Asn Phe Ala Thr Ser Asn Lys Met Asp Met Thr Phe Ser Lys
1580                1585                1590

Gln Asn Ala Leu Leu Arg Ser Glu Tyr Gln Ala Asp Tyr Glu Ser
1595                1600                1605

Leu Arg Phe Phe Ser Leu Leu Ser Gly Ser Leu Asn Ser His Gly
1610                1615                1620

Leu Glu Leu Asn Ala Asp Ile Leu Gly Thr Asp Lys Ile Asn Ser
1625                1630                1635

Gly Ala His Lys Ala Thr Leu Arg Ile Gly Gln Asp Gly Ile Ser
1640                1645                1650

Thr Ser Ala Thr Thr Asn Leu Lys Cys Ser Leu Leu Val Leu Glu
1655                1660                1665

Asn Glu Leu Asn Ala Glu Leu Gly Leu Ser Gly Ala Ser Met Lys
1670                1675                1680

Leu Thr Thr Asn Gly Arg Phe Arg Glu His Asn Ala Lys Phe Ser
1685                1690                1695

Leu Asp Gly Lys Ala Ala Leu Thr Glu Leu Ser Leu Gly Ser Ala
1700                1705                1710

Tyr Gln Ala Met Ile Leu Gly Val Asp Ser Lys Asn Ile Phe Asn
1715                1720                1725

Phe Lys Val Ser Gln Glu Gly Leu Lys Leu Ser Asn Asp Met Met
1730                1735                1740

Gly Ser Tyr Ala Glu Met Lys Phe Asp His Thr Asn Ser Leu Asn
1745                1750                1755

Ile Ala Gly Leu Ser Leu Asp Phe Ser Ser Lys Leu Asp Asn Ile
1760                1765                1770

Tyr Ser Ser Asp Lys Phe Tyr Lys Gln Thr Val Asn Leu Gln Leu
1775                1780                1785

Gln Pro Tyr Ser Leu Val Thr Thr Leu Asn Ser Asp Leu Lys Tyr
1790                1795                1800

Asn Ala Leu Asp Leu Thr Asn Asn Gly Lys Leu Arg Leu Glu Pro
1805                1810                1815

Leu Lys Leu His Val Ala Gly Asn Leu Lys Gly Ala Tyr Gln Asn
1820                1825                1830

Asn Glu Ile Lys His Ile Tyr Ala Ile Ser Ser Ala Ala Leu Ser
1835                1840                1845

Ala Ser Tyr Lys Ala Asp Thr Val Ala Lys Val Gln Gly Val Glu
1850                1855                1860

Phe Ser His Arg Leu Asn Thr Asp Ile Ala Gly Leu Ala Ser Ala
1865                1870                1875

Ile Asp Met Ser Thr Asn Tyr Asn Ser Asp Ser Leu His Phe Ser
1880                1885                1890

Asn Val Phe Arg Ser Val Met Ala Pro Phe Thr Met Thr Ile Asp
1895                1900                1905

Ala His Thr Asn Gly Asn Gly Lys Leu Ala Leu Trp Gly Glu His
1910                1915                1920

Thr Gly Gln Leu Tyr Ser Lys Phe Leu Leu Lys Ala Glu Pro Leu
1925                1930                1935

Ala Phe Thr Phe Ser His Asp Tyr Lys Gly Ser Thr Ser His His
1940                1945                1950

Leu Val Ser Arg Lys Ser Ile Ser Ala Ala Leu Glu His Lys Val
1955                1960                1965
```

Ser Ala Leu Leu Thr Pro Ala Glu Gln Thr Gly Thr Trp Lys Leu
    1970            1975                1980

Lys Thr Gln Phe Asn Asn Asn Glu Tyr Ser Gln Asp Leu Asp Ala
1985                1990                1995

Tyr Asn Thr Lys Asp Lys Ile Gly Val Glu Leu Thr Gly Arg Thr
    2000                2005                2010

Leu Ala Asp Leu Thr Leu Leu Asp Ser Pro Ile Lys Val Pro Leu
    2015                2020                2025

Leu Leu Ser Glu Pro Ile Asn Ile Ile Asp Ala Leu Glu Met Arg
    2030                2035                2040

Asp Ala Val Glu Lys Pro Gln Glu Phe Thr Ile Val Ala Phe Val
    2045                2050                2055

Lys Tyr Asp Lys Asn Gln Asp Val His Ser Ile Asn Leu Pro Phe
    2060                2065                2070

Phe Glu Thr Leu Gln Glu Tyr Phe Glu Arg Asn Arg Gln Thr Ile
    2075                2080                2085

Ile Val Val Leu Glu Asn Val Gln Arg Asn Leu Lys His Ile Asn
    2090                2095                2100

Ile Asp Gln Phe Val Arg Lys Tyr Arg Ala Ala Leu Gly Lys Leu
    2105                2110                2115

Pro Gln Gln Ala Asn Asp Tyr Leu Asn Ser Phe Asn Trp Glu Arg
    2120                2125                2130

Gln Val Ser His Ala Lys Glu Lys Leu Thr Ala Leu Thr Lys Lys
    2135                2140                2145

Tyr Arg Ile Thr Glu Asn Asp Ile Gln Ile Ala Leu Asp Asp Ala
    2150                2155                2160

Lys Ile Asn Phe Asn Glu Lys Leu Ser Gln Leu Gln Thr Tyr Met
    2165                2170                2175

Ile Gln Phe Asp Gln Tyr Ile Lys Asp Ser Tyr Asp Leu His Asp
    2180                2185                2190

Leu Lys Ile Ala Ile Ala Asn Ile Ile Asp Glu Ile Ile Glu Lys
    2195                2200                2205

Leu Lys Ser Leu Asp Glu His Tyr His Ile Arg Val Asn Leu Val
    2210                2215                2220

Lys Thr Ile His Asp Leu His Leu Phe Ile Glu Asn Ile Asp Phe
    2225                2230                2235

Asn Lys Ser Gly Ser Ser Thr Ala Ser Trp Ile Gln Asn Val Asp
    2240                2245                2250

Thr Lys Tyr Gln Ile Arg Ile Gln Ile Gln Glu Lys Leu Gln Gln
    2255                2260                2265

Leu Lys Arg His Ile Gln Asn Ile Asp Ile Gln His Leu Ala Gly
    2270                2275                2280

Lys Leu Lys Gln His Ile Glu Ala Ile Asp Val Arg Val Leu Leu
    2285                2290                2295

Asp Gln Leu Gly Thr Thr Ile Ser Phe Glu Arg Ile Asn Asp Val
    2300                2305                2310

Leu Glu His Val Lys His Phe Val Ile Asn Leu Ile Gly Asp Phe
    2315                2320                2325

Glu Val Ala Glu Lys Ile Asn Ala Phe Arg Ala Lys Val His Glu
    2330                2335                2340

Leu Ile Glu Arg Tyr Glu Val Asp Gln Gln Ile Gln Val Leu Met
    2345                2350                2355

Asp Lys Leu Val Glu Leu Ala His Gln Tyr Lys Leu Lys Glu Thr

|  |  |  | 2360 |  |  |  | 2365 |  |  |  | 2370 |  |  |
|---|---|---|---|---|---|---|---|---|---|---|---|---|---|
| Ile | Gln | Lys | Leu | Ser | Asn | Val | Leu | Gln | Gln | Val | Lys | Ile | Lys | Asp |
|  |  |  | 2375 |  |  |  | 2380 |  |  |  | 2385 |  |  |
| Tyr | Phe | Glu | Lys | Leu | Val | Gly | Phe | Ile | Asp | Asp | Ala | Val | Lys | Lys |
|  |  |  | 2390 |  |  |  | 2395 |  |  |  | 2400 |  |  |
| Leu | Asn | Glu | Leu | Ser | Phe | Lys | Thr | Phe | Ile | Glu | Asp | Val | Asn | Lys |
|  |  |  | 2405 |  |  |  | 2410 |  |  |  | 2415 |  |  |
| Phe | Leu | Asp | Met | Leu | Ile | Lys | Lys | Leu | Lys | Ser | Phe | Asp | Tyr | His |
|  |  |  | 2420 |  |  |  | 2425 |  |  |  | 2430 |  |  |
| Gln | Phe | Val | Asp | Glu | Thr | Asn | Asp | Lys | Ile | Arg | Glu | Val | Thr | Gln |
|  |  |  | 2435 |  |  |  | 2440 |  |  |  | 2445 |  |  |
| Arg | Leu | Asn | Gly | Glu | Ile | Gln | Ala | Leu | Glu | Leu | Pro | Gln | Lys | Ala |
|  |  |  | 2450 |  |  |  | 2455 |  |  |  | 2460 |  |  |
| Glu | Ala | Leu | Lys | Leu | Phe | Leu | Glu | Glu | Thr | Lys | Ala | Thr | Val | Ala |
|  |  |  | 2465 |  |  |  | 2470 |  |  |  | 2475 |  |  |
| Val | Tyr | Leu | Glu | Ser | Leu | Gln | Asp | Thr | Lys | Ile | Thr | Leu | Ile | Ile |
|  |  |  | 2480 |  |  |  | 2485 |  |  |  | 2490 |  |  |
| Asn | Trp | Leu | Gln | Glu | Ala | Leu | Ser | Ser | Ala | Ser | Leu | Ala | His | Met |
|  |  |  | 2495 |  |  |  | 2500 |  |  |  | 2505 |  |  |
| Lys | Ala | Lys | Phe | Arg | Glu | Thr | Leu | Glu | Asp | Thr | Arg | Asp | Arg | Met |
|  |  |  | 2510 |  |  |  | 2515 |  |  |  | 2520 |  |  |
| Tyr | Gln | Met | Asp | Ile | Gln | Gln | Glu | Leu | Gln | Arg | Tyr | Leu | Ser | Leu |
|  |  |  | 2525 |  |  |  | 2530 |  |  |  | 2535 |  |  |
| Val | Gly | Gln | Val | Tyr | Ser | Thr | Leu | Val | Thr | Tyr | Ile | Ser | Asp | Trp |
|  |  |  | 2540 |  |  |  | 2545 |  |  |  | 2550 |  |  |
| Trp | Thr | Leu | Ala | Ala | Lys | Asn | Leu | Thr | Asp | Phe | Ala | Glu | Gln | Tyr |
|  |  |  | 2555 |  |  |  | 2560 |  |  |  | 2565 |  |  |
| Ser | Ile | Gln | Asp | Trp | Ala | Lys | Arg | Met | Lys | Ala | Leu | Val | Glu | Gln |
|  |  |  | 2570 |  |  |  | 2575 |  |  |  | 2580 |  |  |
| Gly | Phe | Thr | Val | Pro | Glu | Ile | Lys | Thr | Ile | Leu | Gly | Thr | Met | Pro |
|  |  |  | 2585 |  |  |  | 2590 |  |  |  | 2595 |  |  |
| Ala | Phe | Glu | Val | Ser | Leu | Gln | Ala | Leu | Gln | Lys | Ala | Thr | Phe | Gln |
|  |  |  | 2600 |  |  |  | 2605 |  |  |  | 2610 |  |  |
| Thr | Pro | Asp | Phe | Ile | Val | Pro | Leu | Thr | Asp | Leu | Arg | Ile | Pro | Ser |
|  |  |  | 2615 |  |  |  | 2620 |  |  |  | 2625 |  |  |
| Val | Gln | Ile | Asn | Phe | Lys | Asp | Leu | Lys | Asn | Ile | Lys | Ile | Pro | Ser |
|  |  |  | 2630 |  |  |  | 2635 |  |  |  | 2640 |  |  |
| Arg | Phe | Ser | Thr | Pro | Glu | Phe | Thr | Ile | Leu | Asn | Thr | Phe | His | Ile |
|  |  |  | 2645 |  |  |  | 2650 |  |  |  | 2655 |  |  |
| Pro | Ser | Phe | Thr | Ile | Asp | Phe | Val | Glu | Met | Lys | Val | Lys | Ile | Ile |
|  |  |  | 2660 |  |  |  | 2665 |  |  |  | 2670 |  |  |
| Arg | Thr | Ile | Asp | Gln | Met | Leu | Asn | Ser | Glu | Leu | Gln | Trp | Pro | Val |
|  |  |  | 2675 |  |  |  | 2680 |  |  |  | 2685 |  |  |
| Pro | Asp | Ile | Tyr | Leu | Arg | Asp | Leu | Lys | Val | Glu | Asp | Ile | Pro | Leu |
|  |  |  | 2690 |  |  |  | 2695 |  |  |  | 2700 |  |  |
| Ala | Arg | Ile | Thr | Leu | Pro | Asp | Phe | Arg | Leu | Pro | Glu | Ile | Ala | Ile |
|  |  |  | 2705 |  |  |  | 2710 |  |  |  | 2715 |  |  |
| Pro | Glu | Phe | Ile | Ile | Pro | Thr | Leu | Asn | Leu | Asn | Asp | Phe | Gln | Val |
|  |  |  | 2720 |  |  |  | 2725 |  |  |  | 2730 |  |  |
| Pro | Asp | Leu | His | Ile | Pro | Glu | Phe | Gln | Leu | Pro | His | Ile | Ser | His |
|  |  |  | 2735 |  |  |  | 2740 |  |  |  | 2745 |  |  |
| Thr | Ile | Glu | Val | Pro | Thr | Phe | Gly | Lys | Leu | Tyr | Ser | Ile | Leu | Lys |
|  |  |  | 2750 |  |  |  | 2755 |  |  |  | 2760 |  |  |

-continued

```
Ile Gln Ser Pro Leu Phe Thr Leu Asp Ala Asn Ala Asp Ile Gly
2765                2770                2775
Asn Gly Thr Thr Ser Ala Asn Glu Ala Gly Ile Ala Ala Ser Ile
2780                2785                2790
Thr Ala Lys Gly Glu Ser Lys Leu Glu Val Leu Asn Phe Asp Phe
2795                2800                2805
Gln Ala Asn Ala Gln Leu Ser Asn Pro Lys Ile Asn Pro Leu Ala
2810                2815                2820
Leu Lys Glu Ser Val Lys Phe Ser Ser Lys Tyr Leu Arg Thr Glu
2825                2830                2835
His Gly Ser Glu Met Leu Phe Phe Gly Asn Ala Ile Glu Gly Lys
2840                2845                2850
Ser Asn Thr Val Ala Ser Leu His Thr Glu Lys Asn Thr Leu Glu
2855                2860                2865
Leu Ser Asn Gly Val Ile Val Lys Ile Asn Asn Gln Leu Thr Leu
2870                2875                2880
Asp Ser Asn Thr Lys Tyr Phe His Lys Leu Asn Ile Pro Lys Leu
2885                2890                2895
Asp Phe Ser Ser Gln Ala Asp Leu Arg Asn Glu Ile Lys Thr Leu
2900                2905                2910
Leu Lys Ala Gly His Ile Ala Trp Thr Ser Ser Gly Lys Gly Ser
2915                2920                2925
Trp Lys Trp Ala Cys Pro Arg Phe Ser Asp Glu Gly Thr His Glu
2930                2935                2940
Ser Gln Ile Ser Phe Thr Ile Glu Gly Pro Leu Thr Ser Phe Gly
2945                2950                2955
Leu Ser Asn Lys Ile Asn Ser Lys His Leu Arg Val Asn Gln Asn
2960                2965                2970
Leu Val Tyr Glu Ser Gly Ser Leu Asn Phe Ser Lys Leu Glu Ile
2975                2980                2985
Gln Ser Gln Val Asp Ser Gln His Val Gly His Ser Val Leu Thr
2990                2995                3000
Ala Lys Gly Met Ala Leu Phe Gly Glu Gly Lys Ala Glu Phe Thr
3005                3010                3015
Gly Arg His Asp Ala His Leu Asn Gly Lys Val Ile Gly Thr Leu
3020                3025                3030
Lys Asn Ser Leu Phe Phe Ser Ala Gln Pro Phe Glu Ile Thr Ala
3035                3040                3045
Ser Thr Asn Asn Glu Gly Asn Leu Lys Val Arg Phe Pro Leu Arg
3050                3055                3060
Leu Thr Gly Lys Ile Asp Phe Leu Asn Asn Tyr Ala Leu Phe Leu
3065                3070                3075
Ser Pro Ser Ala Gln Gln Ser Trp Gln Val Ser Ala Arg Phe
3080                3085                3090
Asn Gln Tyr Lys Tyr Asn Gln Asn Phe Ser Ala Gly Asn Asn Glu
3095                3100                3105
Asn Ile Met Glu Ala His Val Gly Ile Asn Gly Glu Ala Asn Leu
3110                3115                3120
Asp Phe Leu Asn Ile Pro Leu Thr Ile Pro Glu Met Arg Leu Pro
3125                3130                3135
Tyr Thr Ile Ile Thr Thr Pro Pro Leu Lys Asp Phe Ser Leu Trp
3140                3145                3150
Glu Lys Thr Gly Leu Lys Glu Phe Leu Lys Thr Thr Lys Gln Ser
3155                3160                3165
```

```
Phe Asp Leu Ser Val Lys Ala Gln Tyr Lys Lys Asn Lys His Arg
    3170            3175                3180

His Ser Ile Thr Asn Pro Leu Ala Val Leu Cys Glu Phe Ile Ser
    3185            3190                3195

Gln Ser Ile Lys Ser Phe Asp Arg His Phe Glu Lys Asn Arg Asn
    3200            3205                3210

Asn Ala Leu Asp Phe Val Thr Lys Ser Tyr Asn Glu Thr Lys Ile
    3215            3220                3225

Lys Phe Asp Lys Tyr Lys Ala Glu Lys Ser His Asp Glu Leu Pro
    3230            3235                3240

Arg Thr Phe Gln Ile Pro Gly Tyr Thr Val Pro Val Val Asn Val
    3245            3250                3255

Glu Val Ser Pro Phe Thr Ile Glu Met Ser Ala Phe Gly Tyr Val
    3260            3265                3270

Phe Pro Lys Ala Val Ser Met Pro Ser Phe Ser Ile Leu Gly Ser
    3275            3280                3285

Asp Val Arg Val Pro Ser Tyr Thr Leu Ile Leu Pro Ser Leu Glu
    3290            3295                3300

Leu Pro Val Leu His Val Pro Arg Asn Leu Lys Leu Ser Leu Pro
    3305            3310                3315

Asp Phe Lys Glu Leu Cys Thr Ile Ser His Ile Phe Ile Pro Ala
    3320            3325                3330

Met Gly Asn Ile Thr Tyr Asp Phe Ser Phe Lys Ser Ser Val Ile
    3335            3340                3345

Thr Leu Asn Thr Asn Ala Glu Leu Phe Asn Gln Ser Asp Ile Val
    3350            3355                3360

Ala His Leu Leu Ser Ser Ser Ser Val Ile Asp Ala Leu Gln
    3365            3370                3375

Tyr Lys Leu Glu Gly Thr Thr Arg Leu Thr Arg Lys Arg Gly Leu
    3380            3385                3390

Lys Leu Ala Thr Ala Leu Ser Leu Ser Asn Lys Phe Val Glu Gly
    3395            3400                3405

Ser His Asn Ser Thr Val Ser Leu Thr Thr Lys Asn Met Glu Val
    3410            3415                3420

Ser Val Ala Thr Thr Lys Ala Gln Ile Pro Ile Leu Arg Met
    3425            3430                3435

Asn Phe Lys Gln Glu Leu Asn Gly Asn Thr Lys Ser Lys Pro Thr
    3440            3445                3450

Val Ser Ser Ser Met Glu Phe Lys Tyr Asp Phe Asn Ser Ser Met
    3455            3460                3465

Leu Tyr Ser Thr Ala Lys Gly Ala Val Asp His Lys Leu Ser Leu
    3470            3475                3480

Glu Ser Leu Thr Ser Tyr Phe Ser Ile Glu Ser Ser Thr Lys Gly
    3485            3490                3495

Asp Val Lys Gly Ser Val Leu Ser Arg Glu Tyr Ser Gly Thr Ile
    3500            3505                3510

Ala Ser Glu Ala Asn Thr Tyr Leu Asn Ser Lys Ser Thr Arg Ser
    3515            3520                3525

Ser Val Lys Leu Gln Gly Thr Ser Lys Ile Asp Asp Ile Trp Asn
    3530            3535                3540

Leu Glu Val Lys Glu Asn Phe Ala Gly Glu Ala Thr Leu Gln Arg
    3545            3550                3555

Ile Tyr Ser Leu Trp Glu His Ser Thr Lys Asn His Leu Gln Leu
```

```
                    3560                3565                 3570

Glu Gly Leu Phe Phe Thr Asn Gly Glu His Thr Ser Lys Ala Thr
3575                3580                3585

Leu Glu Leu Ser Pro Trp Gln Met Ser Ala Leu Val Gln Val His
3590                3595                3600

Ala Ser Gln Pro Ser Ser Phe His Asp Phe Pro Asp Leu Gly Gln
3605                3610                3615

Glu Val Ala Leu Asn Ala Asn Thr Lys Asn Gln Lys Ile Arg Trp
3620                3625                3630

Lys Asn Glu Val Arg Ile His Ser Gly Ser Phe Gln Ser Gln Val
3635                3640                3645

Glu Leu Ser Asn Asp Gln Glu Lys Ala His Leu Asp Ile Ala Gly
3650                3655                3660

Ser Leu Glu Gly His Leu Arg Phe Leu Lys Asn Ile Ile Leu Pro
3665                3670                3675

Val Tyr Asp Lys Ser Leu Trp Asp Phe Leu Lys Leu Asp Val Thr
3680                3685                3690

Thr Ser Ile Gly Arg Arg Gln His Leu Arg Val Ser Thr Ala Phe
3695                3700                3705

Val Tyr Thr Lys Asn Pro Asn Gly Tyr Ser Phe Ser Ile Pro Val
3710                3715                3720

Lys Val Leu Ala Asp Lys Phe Ile Ile Pro Gly Leu Lys Leu Asn
3725                3730                3735

Asp Leu Asn Ser Val Leu Val Met Pro Thr Phe His Val Pro Phe
3740                3745                3750

Thr Asp Leu Gln Val Pro Ser Cys Lys Leu Asp Phe Arg Glu Ile
3755                3760                3765

Gln Ile Tyr Lys Lys Leu Arg Thr Ser Ser Phe Ala Leu Asn Leu
3770                3775                3780

Pro Thr Leu Pro Glu Val Lys Phe Pro Glu Val Asp Val Leu Thr
3785                3790                3795

Lys Tyr Ser Gln Pro Glu Asp Ser Leu Ile Pro Phe Phe Glu Ile
3800                3805                3810

Thr Val Pro Glu Ser Gln Leu Thr Val Ser Gln Phe Thr Leu Pro
3815                3820                3825

Lys Ser Val Ser Asp Gly Ile Ala Ala Leu Asp Leu Asn Ala Val
3830                3835                3840

Ala Asn Lys Ile Ala Asp Phe Glu Leu Pro Thr Ile Ile Val Pro
3845                3850                3855

Glu Gln Thr Ile Glu Ile Pro Ser Ile Lys Phe Ser Val Pro Ala
3860                3865                3870

Gly Ile Val Ile Pro Ser Phe Gln Ala Leu Thr Ala Arg Phe Glu
3875                3880                3885

Val Asp Ser Pro Val Tyr Asn Ala Thr Trp Ser Ala Ser Leu Lys
3890                3895                3900

Asn Lys Ala Asp Tyr Val Glu Thr Val Leu Asp Ser Thr Cys Ser
3905                3910                3915

Ser Thr Val Gln Phe Leu Glu Tyr Glu Leu Asn Val Leu Gly Thr
3920                3925                3930

His Lys Ile Glu Asp Gly Thr Leu Ala Ser Lys Thr Lys Gly Thr
3935                3940                3945

Phe Ala His Arg Asp Phe Ser Ala Glu Tyr Glu Glu Asp Gly Lys
3950                3955                3960
```

```
Tyr Glu Gly Leu Gln Glu Trp Glu Gly Lys Ala His Leu Asn Ile
    3965                3970                3975

Lys Ser Pro Ala Phe Thr Asp Leu His Leu Arg Tyr Gln Lys Asp
    3980                3985                3990

Lys Lys Gly Ile Ser Thr Ser Ala Ala Ser Pro Ala Val Gly Thr
    3995                4000                4005

Val Gly Met Asp Met Asp Glu Asp Asp Phe Ser Lys Trp Asn
    4010                4015                4020

Phe Tyr Tyr Ser Pro Gln Ser Ser Pro Asp Lys Lys Leu Thr Ile
    4025                4030                4035

Phe Lys Thr Glu Leu Arg Val Arg Glu Ser Asp Glu Thr Gln
    4040                4045                4050

Ile Lys Val Asn Trp Glu Glu Glu Ala Ala Ser Gly Leu Leu Thr
    4055                4060                4065

Ser Leu Lys Asp Asn Val Pro Lys Ala Thr Gly Val Leu Tyr Asp
    4070                4075                4080

Tyr Val Asn Lys Tyr His Trp Glu His Thr Gly Leu Thr Leu Arg
    4085                4090                4095

Glu Val Ser Ser Lys Leu Arg Arg Asn Leu Gln Asn Asn Ala Glu
    4100                4105                4110

Trp Val Tyr Gln Gly Ala Ile Arg Gln Ile Asp Asp Ile Asp Val
    4115                4120                4125

Arg Phe Gln Lys Ala Ala Ser Gly Thr Thr Gly Thr Tyr Gln Glu
    4130                4135                4140

Trp Lys Asp Lys Ala Gln Asn Leu Tyr Gln Glu Leu Leu Thr Gln
    4145                4150                4155

Glu Gly Gln Ala Ser Phe Gln Gly Leu Lys Asp Asn Val Phe Asp
    4160                4165                4170

Gly Leu Val Arg Val Thr Gln Glu Phe His Met Lys Val Lys His
    4175                4180                4185

Leu Ile Asp Ser Leu Ile Asp Phe Leu Asn Phe Pro Arg Phe Gln
    4190                4195                4200

Phe Pro Gly Lys Pro Gly Ile Tyr Thr Arg Glu Glu Leu Cys Thr
    4205                4210                4215

Met Phe Ile Arg Glu Val Gly Thr Val Leu Ser Gln Val Tyr Ser
    4220                4225                4230

Lys Val His Asn Gly Ser Glu Ile Leu Phe Ser Tyr Phe Gln Asp
    4235                4240                4245

Leu Val Ile Thr Leu Pro Phe Glu Leu Arg Lys His Lys Leu Ile
    4250                4255                4260

Asp Val Ile Ser Met Tyr Arg Glu Leu Leu Lys Asp Leu Ser Lys
    4265                4270                4275

Glu Ala Gln Glu Val Phe Lys Ala Ile Gln Ser Leu Lys Thr Thr
    4280                4285                4290

Glu Val Leu Arg Asn Leu Gln Asp Leu Leu Gln Phe Ile Phe Gln
    4295                4300                4305

Leu Ile Glu Asp Asn Ile Lys Gln Leu Lys Glu Met Lys Phe Thr
    4310                4315                4320

Tyr Leu Ile Asn Tyr Ile Gln Asp Glu Ile Asn Thr Ile Phe Ser
    4325                4330                4335

Asp Tyr Ile Pro Tyr Val Phe Lys Leu Leu Lys Glu Asn Leu Cys
    4340                4345                4350

Leu Asn Leu His Lys Phe Asn Glu Phe Ile Gln Asn Glu Leu Gln
    4355                4360                4365
```

-continued

```
Glu Ala Ser Gln Glu Leu Gln Gln Ile His Gln Tyr Ile Met Ala
    4370            4375                4380

Leu Arg Glu Glu Tyr Phe Asp Pro Ser Ile Val Gly Trp Thr Val
    4385            4390                4395

Lys Tyr Tyr Glu Leu Glu Lys Ile Val Ser Leu Ile Lys Asn
    4400            4405                4410

Leu Leu Val Ala Leu Lys Asp Phe His Ser Glu Tyr Ile Val Ser
    4415            4420                4425

Ala Ser Asn Phe Thr Ser Gln Leu Ser Ser Gln Val Glu Gln Phe
    4430            4435                4440

Leu His Arg Asn Ile Gln Glu Tyr Leu Ser Ile Leu Thr Asp Pro
    4445            4450                4455

Asp Gly Lys Gly Lys Glu Lys Ile Ala Glu Leu Ser Ala Thr Ala
    4460            4465                4470

Gln Glu Ile Ile Lys Ser Gln Ala Ile Ala Thr Lys Lys Ile Ile
    4475            4480                4485

Ser Asp Tyr His Gln Gln Phe Arg Tyr Lys Leu Gln Asp Phe Ser
    4490            4495                4500

Asp Gln Leu Ser Asp Tyr Tyr Glu Lys Phe Ile Ala Glu Ser Lys
    4505            4510                4515

Arg Leu Ile Asp Leu Ser Ile Gln Asn Tyr His Thr Phe Leu Ile
    4520            4525                4530

Tyr Ile Thr Glu Leu Leu Lys Lys Leu Gln Ser Thr Thr Val Met
    4535            4540                4545

Asn Pro Tyr Met Lys Leu Ala Pro Gly Glu Leu Thr Ile Ile Leu
    4550            4555                4560

<210> SEQ ID NO 4
<211> LENGTH: 2040
<212> TYPE: PRT
<213> ORGANISM: Homo sapiens

<400> SEQUENCE: 4

Met Glu His Lys Glu Val Val Leu Leu Leu Leu Phe Leu Lys Ser
1               5                   10                  15

Ala Ala Pro Glu Gln Ser His Val Val Gln Asp Cys Tyr His Gly Asp
                20                  25                  30

Gly Gln Ser Tyr Arg Gly Thr Tyr Ser Thr Thr Val Thr Gly Arg Thr
                35                  40                  45

Cys Gln Ala Trp Ser Ser Met Thr Pro His Gln His Asn Arg Thr Thr
    50                  55                  60

Glu Asn Tyr Pro Asn Ala Gly Leu Ile Met Asn Tyr Cys Arg Asn Pro
65                  70                  75                  80

Asp Ala Val Ala Ala Pro Tyr Cys Tyr Thr Arg Asp Pro Gly Val Arg
                85                  90                  95

Trp Glu Tyr Cys Asn Leu Thr Gln Cys Ser Asp Ala Glu Gly Thr Ala
                100                 105                 110

Val Ala Pro Pro Thr Val Thr Pro Val Pro Ser Leu Glu Ala Pro Ser
                115                 120                 125

Glu Gln Ala Pro Thr Glu Gln Arg Pro Gly Val Gln Glu Cys Tyr His
                130                 135                 140

Gly Asn Gly Gln Ser Tyr Arg Gly Thr Tyr Ser Thr Thr Val Thr Gly
145                 150                 155                 160

Arg Thr Cys Gln Ala Trp Ser Ser Met Thr Pro His Ser His Ser Arg
                165                 170                 175
```

```
Thr Pro Glu Tyr Tyr Pro Asn Ala Gly Leu Ile Met Asn Tyr Cys Arg
            180                 185                 190

Asn Pro Asp Ala Val Ala Ala Pro Tyr Cys Tyr Thr Arg Asp Pro Gly
            195                 200                 205

Val Arg Trp Glu Tyr Cys Asn Leu Thr Gln Cys Ser Asp Ala Glu Gly
210                 215                 220

Thr Ala Val Ala Pro Pro Thr Val Thr Pro Val Pro Ser Leu Glu Ala
225                 230                 235                 240

Pro Ser Glu Gln Ala Pro Thr Glu Gln Arg Pro Gly Val Gln Glu Cys
            245                 250                 255

Tyr His Gly Asn Gly Gln Ser Tyr Arg Gly Thr Tyr Ser Thr Thr Val
            260                 265                 270

Thr Gly Arg Thr Cys Gln Ala Trp Ser Ser Met Thr Pro His Ser His
            275                 280                 285

Ser Arg Thr Pro Glu Tyr Tyr Pro Asn Ala Gly Leu Ile Met Asn Tyr
            290                 295                 300

Cys Arg Asn Pro Asp Ala Val Ala Ala Pro Tyr Cys Tyr Thr Arg Asp
305                 310                 315                 320

Pro Gly Val Arg Trp Glu Tyr Cys Asn Leu Thr Gln Cys Ser Asp Ala
            325                 330                 335

Glu Gly Thr Ala Val Ala Pro Pro Thr Val Thr Pro Val Pro Ser Leu
            340                 345                 350

Glu Ala Pro Ser Glu Gln Ala Pro Thr Glu Gln Arg Pro Gly Val Gln
            355                 360                 365

Glu Cys Tyr His Gly Asn Gly Gln Ser Tyr Arg Gly Thr Tyr Ser Thr
            370                 375                 380

Thr Val Thr Gly Arg Thr Cys Gln Ala Trp Ser Ser Met Thr Pro His
385                 390                 395                 400

Ser His Ser Arg Thr Pro Glu Tyr Tyr Pro Asn Ala Gly Leu Ile Met
            405                 410                 415

Asn Tyr Cys Arg Asn Pro Asp Ala Val Ala Ala Pro Tyr Cys Tyr Thr
            420                 425                 430

Arg Asp Pro Gly Val Arg Trp Glu Tyr Cys Asn Leu Thr Gln Cys Ser
            435                 440                 445

Asp Ala Glu Gly Thr Ala Val Ala Pro Pro Thr Val Thr Pro Val Pro
450                 455                 460

Ser Leu Glu Ala Pro Ser Glu Gln Ala Pro Thr Glu Gln Arg Pro Gly
465                 470                 475                 480

Val Gln Glu Cys Tyr His Gly Asn Gly Gln Ser Tyr Arg Gly Thr Tyr
            485                 490                 495

Ser Thr Thr Val Thr Gly Arg Thr Cys Gln Ala Trp Ser Ser Met Thr
            500                 505                 510

Pro His Ser His Ser Arg Thr Pro Glu Tyr Tyr Pro Asn Ala Gly Leu
            515                 520                 525

Ile Met Asn Tyr Cys Arg Asn Pro Asp Ala Val Ala Ala Pro Tyr Cys
            530                 535                 540

Tyr Thr Arg Asp Pro Gly Val Arg Trp Glu Tyr Cys Asn Leu Thr Gln
545                 550                 555                 560

Cys Ser Asp Ala Glu Gly Thr Ala Val Ala Pro Pro Thr Val Thr Pro
            565                 570                 575

Val Pro Ser Leu Glu Ala Pro Ser Glu Gln Ala Pro Thr Glu Gln Arg
            580                 585                 590

Pro Gly Val Gln Glu Cys Tyr His Gly Asn Gly Gln Ser Tyr Arg Gly
```

```
            595                 600                 605
Thr Tyr Ser Thr Thr Val Thr Gly Arg Thr Cys Gln Ala Trp Ser Ser
    610                 615                 620

Met Thr Pro His Ser His Ser Arg Thr Pro Glu Tyr Tyr Pro Asn Ala
625                 630                 635                 640

Gly Leu Ile Met Asn Tyr Cys Arg Asn Pro Asp Ala Val Ala Ala Pro
                    645                 650                 655

Tyr Cys Tyr Thr Arg Asp Pro Gly Val Arg Trp Glu Tyr Cys Asn Leu
                660                 665                 670

Thr Gln Cys Ser Asp Ala Glu Gly Thr Ala Val Ala Pro Pro Thr Val
            675                 680                 685

Thr Pro Val Pro Ser Leu Glu Ala Pro Ser Glu Gln Ala Pro Thr Glu
    690                 695                 700

Gln Arg Pro Gly Val Gln Glu Cys Tyr His Gly Asn Gly Gln Ser Tyr
705                 710                 715                 720

Arg Gly Thr Tyr Ser Thr Thr Val Thr Gly Arg Thr Cys Gln Ala Trp
                    725                 730                 735

Ser Ser Met Thr Pro His Ser His Ser Arg Thr Pro Glu Tyr Tyr Pro
                740                 745                 750

Asn Ala Gly Leu Ile Met Asn Tyr Cys Arg Asn Pro Asp Ala Val Ala
            755                 760                 765

Ala Pro Tyr Cys Tyr Thr Arg Asp Pro Gly Val Arg Trp Glu Tyr Cys
    770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                    805                 810                 815

Thr Glu Gln Arg Pro Gly Val Gln Glu Cys Tyr His Gly Asn Gly Gln
                820                 825                 830

Ser Tyr Arg Gly Thr Tyr Ser Thr Thr Val Thr Gly Arg Thr Cys Gln
            835                 840                 845

Ala Trp Ser Ser Met Thr Pro His Ser His Ser Arg Thr Pro Glu Tyr
    850                 855                 860

Tyr Pro Asn Ala Gly Leu Ile Met Asn Tyr Cys Arg Asn Pro Asp Pro
865                 870                 875                 880

Val Ala Ala Pro Tyr Cys Tyr Thr Arg Asp Pro Ser Val Arg Trp Glu
                    885                 890                 895

Tyr Cys Asn Leu Thr Gln Cys Ser Asp Ala Glu Gly Thr Ala Val Ala
                900                 905                 910

Pro Pro Thr Ile Thr Pro Ile Pro Ser Leu Glu Ala Pro Ser Glu Gln
            915                 920                 925

Ala Pro Thr Glu Gln Arg Pro Gly Val Gln Glu Cys Tyr His Gly Asn
    930                 935                 940

Gly Gln Ser Tyr Gln Gly Thr Tyr Phe Ile Thr Val Thr Gly Arg Thr
945                 950                 955                 960

Cys Gln Ala Trp Ser Ser Met Thr Pro His Ser His Ser Arg Thr Pro
                    965                 970                 975

Ala Tyr Tyr Pro Asn Ala Gly Leu Ile Lys Asn Tyr Cys Arg Asn Pro
                980                 985                 990

Asp Pro Val Ala Ala Pro Trp Cys Tyr Thr Thr Asp Pro Ser Val Arg
            995                 1000                1005

Trp Glu Tyr Cys Asn Leu Thr Arg Cys Ser Asp Ala Glu Trp Thr
    1010                1015                1020
```

-continued

```
Ala Phe Val Pro Pro Asn Val Ile Leu Ala Pro Ser Leu Glu Ala
    1025                1030                1035

Phe Phe Glu Gln Ala Leu Thr Glu Glu Thr Pro Gly Val Gln Asp
    1040                1045                1050

Cys Tyr Tyr His Tyr Gly Gln Ser Tyr Arg Gly Thr Tyr Ser Thr
    1055                1060                1065

Thr Val Thr Gly Arg Thr Cys Gln Ala Trp Ser Ser Met Thr Pro
    1070                1075                1080

His Gln His Ser Arg Thr Pro Glu Asn Tyr Pro Asn Ala Gly Leu
    1085                1090                1095

Thr Arg Asn Tyr Cys Arg Asn Pro Asp Ala Glu Ile Arg Pro Trp
    1100                1105                1110

Cys Tyr Thr Met Asp Pro Ser Val Arg Trp Glu Tyr Cys Asn Leu
    1115                1120                1125

Thr Gln Cys Leu Val Thr Glu Ser Ser Val Leu Ala Thr Leu Thr
    1130                1135                1140

Val Val Pro Asp Pro Ser Thr Glu Ala Ser Ser Glu Glu Ala Pro
    1145                1150                1155

Thr Glu Gln Ser Pro Gly Val Gln Asp Cys Tyr His Gly Asp Gly
    1160                1165                1170

Gln Ser Tyr Arg Gly Ser Phe Ser Thr Thr Val Thr Gly Arg Thr
    1175                1180                1185

Cys Gln Ser Trp Ser Ser Met Thr Pro His Trp His Gln Arg Thr
    1190                1195                1200

Thr Glu Tyr Tyr Pro Asn Gly Gly Leu Thr Arg Asn Tyr Cys Arg
    1205                1210                1215

Asn Pro Asp Ala Glu Ile Ser Pro Trp Cys Tyr Thr Met Asp Pro
    1220                1225                1230

Asn Val Arg Trp Glu Tyr Cys Asn Leu Thr Gln Cys Pro Val Thr
    1235                1240                1245

Glu Ser Ser Val Leu Ala Thr Ser Thr Ala Val Ser Glu Gln Ala
    1250                1255                1260

Pro Thr Glu Gln Ser Pro Thr Val Gln Asp Cys Tyr His Gly Asp
    1265                1270                1275

Gly Gln Ser Tyr Arg Gly Ser Phe Ser Thr Thr Val Thr Gly Arg
    1280                1285                1290

Thr Cys Gln Ser Trp Ser Ser Met Thr Pro His Trp His Gln Arg
    1295                1300                1305

Thr Thr Glu Tyr Tyr Pro Asn Gly Gly Leu Thr Arg Asn Tyr Cys
    1310                1315                1320

Arg Asn Pro Asp Ala Glu Ile Arg Pro Trp Cys Tyr Thr Met Asp
    1325                1330                1335

Pro Ser Val Arg Trp Glu Tyr Cys Asn Leu Thr Gln Cys Pro Val
    1340                1345                1350

Met Glu Ser Thr Leu Leu Thr Thr Pro Thr Val Val Pro Val Pro
    1355                1360                1365

Ser Thr Glu Leu Pro Ser Glu Glu Ala Pro Thr Glu Asn Ser Thr
    1370                1375                1380

Gly Val Gln Asp Cys Tyr Arg Gly Asp Gly Gln Ser Tyr Arg Gly
    1385                1390                1395

Thr Leu Ser Thr Thr Ile Thr Gly Arg Thr Cys Gln Ser Trp Ser
    1400                1405                1410

Ser Met Thr Pro His Trp His Arg Arg Ile Pro Leu Tyr Tyr Pro
    1415                1420                1425
```

-continued

```
Asn Ala Gly Leu Thr Arg Asn Tyr Cys Arg Asn Pro Asp Ala Glu
    1430                1435                1440
Ile Arg Pro Trp Cys Tyr Thr Met Asp Pro Ser Val Arg Trp Glu
    1445                1450                1455
Tyr Cys Asn Leu Thr Arg Cys Pro Val Thr Glu Ser Ser Val Leu
    1460                1465                1470
Thr Thr Pro Thr Val Ala Pro Val Pro Ser Thr Glu Ala Pro Ser
    1475                1480                1485
Glu Gln Ala Pro Pro Glu Lys Ser Pro Val Val Gln Asp Cys Tyr
    1490                1495                1500
His Gly Asp Gly Arg Ser Tyr Arg Gly Ile Ser Ser Thr Thr Val
    1505                1510                1515
Thr Gly Arg Thr Cys Gln Ser Trp Ser Ser Met Ile Pro His Trp
    1520                1525                1530
His Gln Arg Thr Pro Glu Asn Tyr Pro Asn Ala Gly Leu Thr Glu
    1535                1540                1545
Asn Tyr Cys Arg Asn Pro Asp Ser Gly Lys Gln Pro Trp Cys Tyr
    1550                1555                1560
Thr Thr Asp Pro Cys Val Arg Trp Glu Tyr Cys Asn Leu Thr Gln
    1565                1570                1575
Cys Ser Glu Thr Glu Ser Gly Val Leu Glu Thr Pro Thr Val Val
    1580                1585                1590
Pro Val Pro Ser Met Glu Ala His Ser Glu Ala Ala Pro Thr Glu
    1595                1600                1605
Gln Thr Pro Val Val Arg Gln Cys Tyr His Gly Asn Gly Gln Ser
    1610                1615                1620
Tyr Arg Gly Thr Phe Ser Thr Thr Val Thr Gly Arg Thr Cys Gln
    1625                1630                1635
Ser Trp Ser Ser Met Thr Pro His Arg His Gln Arg Thr Pro Glu
    1640                1645                1650
Asn Tyr Pro Asn Asp Gly Leu Thr Met Asn Tyr Cys Arg Asn Pro
    1655                1660                1665
Asp Ala Asp Thr Gly Pro Trp Cys Phe Thr Met Asp Pro Ser Ile
    1670                1675                1680
Arg Trp Glu Tyr Cys Asn Leu Thr Arg Cys Ser Asp Thr Glu Gly
    1685                1690                1695
Thr Val Val Ala Pro Pro Thr Val Ile Gln Val Pro Ser Leu Gly
    1700                1705                1710
Pro Pro Ser Glu Gln Asp Cys Met Phe Gly Asn Gly Lys Gly Tyr
    1715                1720                1725
Arg Gly Lys Lys Ala Thr Thr Val Thr Gly Thr Pro Cys Gln Glu
    1730                1735                1740
Trp Ala Ala Gln Glu Pro His Arg His Ser Thr Phe Ile Pro Gly
    1745                1750                1755
Thr Asn Lys Trp Ala Gly Leu Glu Lys Asn Tyr Cys Arg Asn Pro
    1760                1765                1770
Asp Gly Asp Ile Asn Gly Pro Trp Cys Tyr Thr Met Asn Pro Arg
    1775                1780                1785
Lys Leu Phe Asp Tyr Cys Asp Ile Pro Leu Cys Ala Ser Ser Ser
    1790                1795                1800
Phe Asp Cys Gly Lys Pro Gln Val Glu Pro Lys Lys Cys Pro Gly
    1805                1810                1815
Ser Ile Val Gly Gly Cys Val Ala His Pro His Ser Trp Pro Trp
```

-continued

```
                1820                1825                1830

Gln Val Ser Leu Arg Thr Arg Phe Gly Lys His Phe Cys Gly Gly
        1835                1840                1845

Thr Leu Ile Ser Pro Glu Trp Val Leu Thr Ala Ala His Cys Leu
        1850                1855                1860

Lys Lys Ser Ser Arg Pro Ser Ser Tyr Lys Val Ile Leu Gly Ala
        1865                1870                1875

His Gln Glu Val Asn Leu Glu Ser His Val Gln Glu Ile Glu Val
        1880                1885                1890

Ser Arg Leu Phe Leu Glu Pro Thr Gln Ala Asp Ile Ala Leu Leu
        1895                1900                1905

Lys Leu Ser Arg Pro Ala Val Ile Thr Asp Lys Val Met Pro Ala
        1910                1915                1920

Cys Leu Pro Ser Pro Asp Tyr Met Val Thr Ala Arg Thr Glu Cys
        1925                1930                1935

Tyr Ile Thr Gly Trp Gly Glu Thr Gln Gly Thr Phe Gly Thr Gly
        1940                1945                1950

Leu Leu Lys Glu Ala Gln Leu Leu Val Ile Glu Asn Glu Val Cys
        1955                1960                1965

Asn His Tyr Lys Tyr Ile Cys Ala Glu His Leu Ala Arg Gly Thr
        1970                1975                1980

Asp Ser Cys Gln Gly Asp Ser Gly Gly Pro Leu Val Cys Phe Glu
        1985                1990                1995

Lys Asp Lys Tyr Ile Leu Gln Gly Val Thr Ser Trp Gly Leu Gly
        2000                2005                2010

Cys Ala Arg Pro Asn Lys Pro Gly Val Tyr Ala Arg Val Ser Arg
        2015                2020                2025

Phe Val Thr Trp Ile Glu Gly Met Met Arg Asn Asn
        2030                2035                2040

<210> SEQ ID NO 5
<211> LENGTH: 83
<212> TYPE: PRT
<213> ORGANISM: Homo sapiens

<400> SEQUENCE: 5

Met Arg Leu Phe Leu Ser Leu Pro Val Leu Val Val Val Leu Ser Ile
1               5                   10                  15

Val Leu Glu Gly Pro Ala Pro Ala Gln Gly Thr Pro Asp Val Ser Ser
                20                  25                  30

Ala Leu Asp Lys Leu Lys Glu Phe Gly Asn Thr Leu Glu Asp Lys Ala
            35                  40                  45

Arg Glu Leu Ile Ser Arg Ile Lys Gln Ser Glu Leu Ser Ala Lys Met
        50                  55                  60

Arg Glu Trp Phe Ser Glu Thr Phe Gln Lys Val Lys Glu Lys Leu Lys
65                  70                  75                  80

Ile Asp Ser

<210> SEQ ID NO 6
<211> LENGTH: 99
<212> TYPE: PRT
<213> ORGANISM: Homo sapiens

<400> SEQUENCE: 6

Met Gln Pro Arg Val Leu Leu Val Val Ala Leu Leu Ala Leu Leu Ala
1               5                   10                  15
```

-continued

Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Ala Arg Gly Trp Val Thr
    50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala

<210> SEQ ID NO 7
<211> LENGTH: 130
<212> TYPE: PRT
<213> ORGANISM: Homo sapiens

<400> SEQUENCE: 7

Met Arg Leu Phe Thr Gly Ile Val Phe Cys Ser Leu Val Met Gly Val
1               5                   10                  15

Thr Ser Glu Ser Trp Arg Ser Phe Phe Lys Glu Ala Leu Gln Gly Val
            20                  25                  30

Gly Asp Met Gly Arg Ala Tyr Trp Asp Ile Met Ile Ser Asn His Gln
        35                  40                  45

Asn Ser Asn Arg Tyr Leu Tyr Ala Arg Gly Asn Tyr Asp Ala Ala Gln
    50                  55                  60

Arg Gly Pro Gly Gly Val Trp Ala Ala Lys Leu Ile Ser Arg Ser Arg
65                  70                  75                  80

Val Tyr Leu Gln Gly Leu Ile Asp Tyr Tyr Leu Phe Gly Asn Ser Ser
                85                  90                  95

Thr Val Leu Glu Asp Ser Lys Ser Asn Glu Lys Ala Glu Glu Trp Gly
            100                 105                 110

Arg Ser Gly Lys Asp Pro Asp Arg Phe Arg Pro Asp Gly Leu Pro Lys
        115                 120                 125

Lys Tyr
    130

<210> SEQ ID NO 8
<211> LENGTH: 317
<212> TYPE: PRT
<213> ORGANISM: Homo sapiens

<400> SEQUENCE: 8

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
        130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 9
<211> LENGTH: 7
<212> TYPE: PRT
<213> ORGANISM: Homo sapiens

<400> SEQUENCE: 9

Ile Thr Leu Pro Asp Phe Arg
1               5

<210> SEQ ID NO 10
<211> LENGTH: 9
<212> TYPE: PRT
<213> ORGANISM: Homo sapiens

<400> SEQUENCE: 10

Ser Val Gly Phe His Leu Pro Ser Arg
1               5

<210> SEQ ID NO 11
<211> LENGTH: 9
<212> TYPE: PRT
<213> ORGANISM: Homo sapiens

<400> SEQUENCE: 11

Ala Lys Pro Ala Leu Glu Asp Leu Arg
1               5

<210> SEQ ID NO 12
<211> LENGTH: 9
<212> TYPE: PRT
<213> ORGANISM: Homo sapiens
<220> FEATURE:
<221> NAME/KEY: MISC_FEATURE

```
<222> LOCATION: (8)..(8)
<223> OTHER INFORMATION: Wherein Met at position 8 is optionally
      oxidized

<400> SEQUENCE: 12

Leu Ser Pro Leu Gly Glu Glu Met Arg
1               5

<210> SEQ ID NO 13
<211> LENGTH: 9
<212> TYPE: PRT
<213> ORGANISM: Homo sapiens

<400> SEQUENCE: 13

Leu Gln Ala Glu Ala Phe Gln Ala Arg
1               5

<210> SEQ ID NO 14
<211> LENGTH: 9
<212> TYPE: PRT
<213> ORGANISM: Homo sapiens

<400> SEQUENCE: 14

Leu Ser Pro Leu Gly Glu Glu Met Arg
1               5

<210> SEQ ID NO 15
<211> LENGTH: 9
<212> TYPE: PRT
<213> ORGANISM: Homo sapiens

<400> SEQUENCE: 15

Leu Ala Ala Tyr Leu Met Leu Met Arg
1               5

<210> SEQ ID NO 16
<211> LENGTH: 9
<212> TYPE: PRT
<213> ORGANISM: Homo sapiens

<400> SEQUENCE: 16

His Ile Asn Ile Asp Gln Phe Val Arg
1               5

<210> SEQ ID NO 17
<211> LENGTH: 10
<212> TYPE: PRT
<213> ORGANISM: Homo sapiens

<400> SEQUENCE: 17

Ser Lys Glu Gln Leu Thr Pro Leu Ile Lys
1               5                   10

<210> SEQ ID NO 18
<211> LENGTH: 10
<212> TYPE: PRT
<213> ORGANISM: Homo sapiens

<400> SEQUENCE: 18

Ser Pro Ala Phe Thr Asp Leu His Leu Arg
1               5                   10

<210> SEQ ID NO 19
<211> LENGTH: 11
<212> TYPE: PRT
<213> ORGANISM: Homo sapiens
```

```
<400> SEQUENCE: 19

Leu Glu Ala Leu Lys Glu Asn Gly Gly Ala Arg
1               5                   10

<210> SEQ ID NO 20
<211> LENGTH: 9
<212> TYPE: PRT
<213> ORGANISM: Homo sapiens

<400> SEQUENCE: 20

Phe Arg Glu Thr Leu Glu Asp Thr Arg
1               5

<210> SEQ ID NO 21
<211> LENGTH: 9
<212> TYPE: PRT
<213> ORGANISM: Homo sapiens

<400> SEQUENCE: 21

Ser Leu Asp Glu His Tyr His Ile Arg
1               5

<210> SEQ ID NO 22
<211> LENGTH: 10
<212> TYPE: PRT
<213> ORGANISM: Homo sapiens

<400> SEQUENCE: 22

Val Leu Val Asp His Phe Gly Tyr Thr Lys
1               5                   10

<210> SEQ ID NO 23
<211> LENGTH: 11
<212> TYPE: PRT
<213> ORGANISM: Homo sapiens

<400> SEQUENCE: 23

Val Lys Ser Pro Glu Leu Gln Ala Glu Ala Lys
1               5                   10

<210> SEQ ID NO 24
<211> LENGTH: 10
<212> TYPE: PRT
<213> ORGANISM: Homo sapiens

<400> SEQUENCE: 24

Leu Thr Ile Ser Glu Gln Asn Ile Gln Arg
1               5                   10

<210> SEQ ID NO 25
<211> LENGTH: 10
<212> TYPE: PRT
<213> ORGANISM: Homo sapiens

<400> SEQUENCE: 25

Asp Glu Pro Pro Gln Ser Pro Trp Asp Arg
1               5                   10

<210> SEQ ID NO 26
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
```

<223> OTHER INFORMATION: Wherein Met at position 5 is optionally
      oxidized

<400> SEQUENCE: 26

Trp Gln Glu Glu Met Glu Leu Tyr Arg
1               5

<210> SEQ ID NO 27
<211> LENGTH: 11
<212> TYPE: PRT
<213> ORGANISM: Homo sapiens

<400> SEQUENCE: 27

Thr His Leu Ala Pro Tyr Ser Asp Glu Leu Arg
1               5                   10

<210> SEQ ID NO 28
<211> LENGTH: 11
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Wherein Met at position 8 is optionally
      oxidized

<400> SEQUENCE: 28

Leu Ser Pro Leu Gly Glu Glu Met Arg Asp Arg
1               5                   10

<210> SEQ ID NO 29
<211> LENGTH: 12
<212> TYPE: PRT
<213> ORGANISM: Homo sapiens

<400> SEQUENCE: 29

Lys Gly Asn Val Ala Thr Glu Ile Ser Thr Glu Arg
1               5                   10

<210> SEQ ID NO 30
<211> LENGTH: 11
<212> TYPE: PRT
<213> ORGANISM: Homo sapiens

<400> SEQUENCE: 30

Val Gln Pro Tyr Leu Asp Asp Phe Gln Lys Lys
1               5                   10

<210> SEQ ID NO 31
<211> LENGTH: 13
<212> TYPE: PRT
<213> ORGANISM: Homo sapiens

<400> SEQUENCE: 31

Asp Tyr Val Ser Gln Phe Glu Gly Ser Ala Leu Gly Lys
1               5                   10

<210> SEQ ID NO 32
<211> LENGTH: 12
<212> TYPE: PRT
<213> ORGANISM: Homo sapiens

<400> SEQUENCE: 32

Phe Gln Phe Pro Gly Lys Pro Gly Ile Tyr Thr Arg
1               5                   10

```
<210> SEQ ID NO 33
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Wherein Met at position 6 is optionally
      oxidized

<400> SEQUENCE: 33

Lys Trp Gln Glu Glu Met Glu Leu Tyr Arg
1               5                   10

<210> SEQ ID NO 34
<211> LENGTH: 12
<212> TYPE: PRT
<213> ORGANISM: Homo sapiens

<400> SEQUENCE: 34

Asp Pro Asp Arg Phe Arg Pro Asp Gly Leu Pro Lys
1               5                   10

<210> SEQ ID NO 35
<211> LENGTH: 13
<212> TYPE: PRT
<213> ORGANISM: Homo sapiens

<400> SEQUENCE: 35

Asn Pro Asp Ala Val Ala Ala Pro Tyr Cys Tyr Thr Arg
1               5                   10

<210> SEQ ID NO 36
<211> LENGTH: 11
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Wherein Met at position 1 is optionally
      oxidized

<400> SEQUENCE: 36

Met Arg Glu Trp Phe Ser Glu Thr Phe Gln Lys
1               5                   10

<210> SEQ ID NO 37
<211> LENGTH: 15
<212> TYPE: PRT
<213> ORGANISM: Homo sapiens

<400> SEQUENCE: 37

Leu Ala Ala Arg Leu Glu Ala Leu Lys Glu Asn Gly Gly Ala Arg
1               5                   10                  15

<210> SEQ ID NO 38
<211> LENGTH: 13
<212> TYPE: PRT
<213> ORGANISM: Homo sapiens

<400> SEQUENCE: 38

Thr His Leu Ala Pro Tyr Ser Asp Glu Leu Arg Gln Arg
1               5                   10

<210> SEQ ID NO 39
<211> LENGTH: 14
<212> TYPE: PRT
<213> ORGANISM: Homo sapiens
```

<400> SEQUENCE: 39

Leu Leu Asp Asn Trp Asp Ser Val Thr Ser Thr Phe Ser Lys
1               5                   10

<210> SEQ ID NO 40
<211> LENGTH: 16
<212> TYPE: PRT
<213> ORGANISM: Homo sapiens

<400> SEQUENCE: 40

Asp Ala Leu Ser Ser Val Gln Glu Ser Gln Val Ala Gln Gln Ala Arg
1               5                   10                  15

<210> SEQ ID NO 41
<211> LENGTH: 15
<212> TYPE: PRT
<213> ORGANISM: Homo sapiens

<400> SEQUENCE: 41

Gln Lys Val Glu Pro Leu Arg Ala Glu Leu Gln Glu Gly Ala Arg
1               5                   10                  15

<210> SEQ ID NO 42
<211> LENGTH: 14
<212> TYPE: PRT
<213> ORGANISM: Homo sapiens

<400> SEQUENCE: 42

Ile Val Gln Ile Leu Pro Trp Glu Gln Asn Glu Gln Val Lys
1               5                   10

<210> SEQ ID NO 43
<211> LENGTH: 15
<212> TYPE: PRT
<213> ORGANISM: Homo sapiens

<400> SEQUENCE: 43

Asn Leu Gln Asn Asn Ala Glu Trp Val Tyr Gln Gly Ala Ile Arg
1               5                   10                  15

<210> SEQ ID NO 44
<211> LENGTH: 16
<212> TYPE: PRT
<213> ORGANISM: Homo sapiens

<400> SEQUENCE: 44

Thr Pro Glu Tyr Tyr Pro Asn Ala Gly Leu Ile Met Asn Tyr Cys Arg
1               5                   10                  15

<210> SEQ ID NO 45
<211> LENGTH: 17
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: Wherein Met at position 12 is optionally
      oxidized

<400> SEQUENCE: 45

Ser Glu Ala Glu Asp Ala Ser Leu Leu Ser Phe Met Gln Gly Tyr Met
1               5                   10                  15
Lys

```
<210> SEQ ID NO 46
<211> LENGTH: 18
<212> TYPE: PRT
<213> ORGANISM: Homo sapiens

<400> SEQUENCE: 46

Leu Arg Glu Gln Leu Gly Pro Val Thr Gln Glu Phe Trp Asp Asn Leu
1               5                   10                  15

Glu Lys

<210> SEQ ID NO 47
<211> LENGTH: 20
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: Wherein Met at position 16 is optionally
      oxidized

<400> SEQUENCE: 47

Val Gln Pro Tyr Leu Asp Asp Phe Gln Lys Lys Trp Gln Glu Glu Met
1               5                   10                  15

Glu Leu Tyr Arg
            20

<210> SEQ ID NO 48
<211> LENGTH: 10
<212> TYPE: PRT
<213> ORGANISM: Homo sapiens

<400> SEQUENCE: 48

Asp Glu Pro Pro Gln Ser Pro Trp Asp Arg
1               5                   10

<210> SEQ ID NO 49
<211> LENGTH: 18
<212> TYPE: PRT
<213> ORGANISM: Homo sapiens

<400> SEQUENCE: 49

Leu Arg Glu Gln Leu Gly Pro Val Thr Gln Glu Phe Trp Asp Asn Leu
1               5                   10                  15

Glu Lys

<210> SEQ ID NO 50
<211> LENGTH: 9
<212> TYPE: PRT
<213> ORGANISM: Homo sapiens

<400> SEQUENCE: 50

Ala Lys Pro Ala Leu Glu Asp Leu Arg
1               5

<210> SEQ ID NO 51
<211> LENGTH: 11
<212> TYPE: PRT
<213> ORGANISM: Homo sapiens

<400> SEQUENCE: 51

Val Gln Pro Tyr Leu Asp Asp Phe Gln Lys Lys
1               5                   10

<210> SEQ ID NO 52
<211> LENGTH: 14
```

```
<212> TYPE: PRT
<213> ORGANISM: Homo sapiens

<400> SEQUENCE: 52

Leu Leu Asp Asn Trp Asp Ser Val Thr Ser Thr Phe Ser Lys
1               5                   10
```